(12) United States Patent
Janardhan

(10) Patent No.: US 9,034,007 B2
(45) Date of Patent: May 19, 2015

(54) DISTAL EMBOLIC PROTECTION DEVICES WITH A VARIABLE THICKNESS MICROGUIDEWIRE AND METHODS FOR THEIR USE

(75) Inventor: Vikram Janardhan, Sacramento, CA (US)

(73) Assignee: Insera Therapeutics, Inc., Sacramento, CA (US)

( * ) Notice: Subject to any disclaimer, the term of this patent is extended or adjusted under 35 U.S.C. 154(b) by 264 days.

(21) Appl. No.: 11/859,272

(22) Filed: Sep. 21, 2007

(65) Prior Publication Data
US 2009/0082800 A1   Mar. 26, 2009

(51) Int. Cl.
*A61M 29/00* (2006.01)
*A61F 2/01* (2006.01)
(Continued)

(52) U.S. Cl.
CPC . *A61F 2/013* (2013.01); *A61F 2/95* (2013.01); *A61F 2002/018* (2013.01); *A61M 25/09* (2013.01); *A61F 2230/0006* (2013.01); *A61F 2230/008* (2013.01)

(58) Field of Classification Search
CPC ... A61F 2/962; A61F 2/95; A61F 2002/9522; A61F 2/01; A61F 2002/011; A61M 2025/0042; A61M 2025/09075; A61M 2025/09133; A61M 25/0043; A61M 25/0045
USPC .......... 606/200, 114, 108; 604/104; 623/1.11, 623/1.12; 600/585, 434–435
See application file for complete search history.

(56) References Cited

U.S. PATENT DOCUMENTS

| | | | |
|---|---|---|---|
| 3,378,282 | A | 4/1968 | Demler, Sr. |
| 3,381,114 | A | 4/1968 | Nakanuma |

(Continued)

FOREIGN PATENT DOCUMENTS

| | | |
|---|---|---|
| EP | 0 521 595 | 1/1993 |
| EP | 1 676 545 | 7/2006 |

(Continued)

OTHER PUBLICATIONS

International Search Report dated Nov. 28, 2008 (PCT/ISA/220 & PCT/ISA/210) (Three (3) pages).

(Continued)

*Primary Examiner* — Darwin Erezo
*Assistant Examiner* — Sidharth Kapoor
(74) *Attorney, Agent, or Firm* — Knobbe Martens Olson & Bear, LLP

(57) ABSTRACT

A distal embolic protection device for dedicated use in cerebral arterial blood vessels is described. The distal embolic protection device comprises a variable-thickness microguidewire and a collapsible filtering device mounted on the microguidewire over two mobile attachment points so that in its collapsed configuration, the thickness of the microguidewire and the filtering device at this region is less than or equal to 0.017 inch (0.432 mm) in thickness to be able to pass through existing conventional microcatheters. The mobile attachment points allow for rotatory and longitudinal mobility of the microguidewire while the filtering device is stable thereby decreasing the risk of trauma to the fragile cerebral arterial blood vessels. Preferably, the filtering device comprises an expansion assembly, e.g., a plurality of struts attached to a filter membrane that are in a folded position which self expand to the desired dimensions within the cerebral blood vessels. Also described are methods of using the distal embolic protection devices of this invention.

41 Claims, 37 Drawing Sheets

(51) Int. Cl.
　　　A61F 2/95　　　(2013.01)
　　　A61M 25/09　　(2006.01)

(56) References Cited

U.S. PATENT DOCUMENTS

| | | | |
|---|---|---|---|
| 3,596,545 A | 8/1971 | Eisenhardt |
| 3,790,744 A | 2/1974 | Bowen |
| 4,030,503 A | 6/1977 | Clark, III |
| 4,334,535 A | 6/1982 | Wilson et al. |
| 4,560,378 A | 12/1985 | Weiland |
| 4,585,436 A | 4/1986 | Davis et al. |
| 4,778,559 A | 10/1988 | McNeilly |
| 4,964,320 A | 10/1990 | Lee, Jr. |
| 4,984,581 A | 1/1991 | Stice |
| 4,989,606 A | 2/1991 | Gehrich et al. |
| 5,073,694 A | 12/1991 | Tessier et al. |
| 5,108,419 A | 4/1992 | Reger et al. |
| 5,160,342 A | 11/1992 | Reger et al. |
| 5,171,383 A | 12/1992 | Sagae et al. |
| 5,195,408 A | 3/1993 | Niehaus |
| 5,211,183 A | 5/1993 | Wilson |
| 5,234,451 A | 8/1993 | Osypka |
| 5,265,622 A | 11/1993 | Barbere |
| 5,324,276 A | 6/1994 | Rosenberg |
| 5,370,609 A | 12/1994 | Drasler et al. |
| 5,378,234 A | 1/1995 | Hammerslag et al. |
| 5,383,387 A | 1/1995 | Chesterfield et al. |
| 5,398,568 A | 3/1995 | Worrell et al. |
| 5,423,849 A | 6/1995 | Engelson et al. |
| 5,449,372 A | 9/1995 | Schmaltz et al. |
| 5,484,409 A | 1/1996 | Atkinson et al. |
| 5,522,822 A | 6/1996 | Phelps et al. |
| 5,537,696 A | 7/1996 | Chartier |
| 5,562,641 A | 10/1996 | Flomenblit et al. |
| 5,573,520 A | 11/1996 | Schwartz |
| 5,578,074 A | 11/1996 | Mirigian |
| 5,624,508 A | 4/1997 | Flomenblit et al. |
| 5,645,558 A | 7/1997 | Horton |
| 5,690,120 A | 11/1997 | Jacobsen |
| 5,695,506 A | 12/1997 | Pike et al. |
| 5,695,507 A | 12/1997 | Auth et al. |
| 5,697,899 A | 12/1997 | Hillman et al. |
| 5,725,570 A | 3/1998 | Heath |
| 5,725,572 A | 3/1998 | Lam et al. |
| 5,733,400 A | 3/1998 | Gore et al. |
| 5,741,429 A | 4/1998 | Donadio, III et al. |
| 5,766,219 A | 6/1998 | Horton |
| 5,780,807 A | 7/1998 | Saunders |
| 5,788,558 A | 8/1998 | Klein |
| 5,836,066 A | 11/1998 | Ingram |
| 5,843,051 A | 12/1998 | Adams et al. |
| 5,843,117 A | 12/1998 | Alt et al. |
| 5,849,037 A | 12/1998 | Frid |
| 5,865,816 A | 2/1999 | Quinn |
| 5,868,708 A | 2/1999 | Hart et al. |
| 5,876,568 A | 3/1999 | Kindersley |
| 5,879,499 A | 3/1999 | Corvi |
| 5,882,444 A | 3/1999 | Flomenblit et al. |
| 5,895,398 A | 4/1999 | Wensel et al. |
| 5,895,407 A | 4/1999 | Jayaraman |
| 5,897,567 A | 4/1999 | Ressemann et al. |
| 5,911,731 A | 6/1999 | Pham et al. |
| 5,941,869 A | 8/1999 | Patterson et al. |
| 5,944,701 A | 8/1999 | Dubrul |
| 5,951,599 A | 9/1999 | McCrory |
| 5,972,019 A | 10/1999 | Engelson et al. |
| 5,994,667 A | 11/1999 | Merdan et al. |
| 5,996,929 A | 12/1999 | Mazodier et al. |
| 6,019,778 A | 2/2000 | Wilson et al. |
| 6,027,863 A | 2/2000 | Donadio, III |
| 6,030,406 A | 2/2000 | Davis et al. |
| 6,030,586 A | 2/2000 | Kuan |
| 6,066,149 A | 5/2000 | Samson et al. |
| 6,080,170 A | 6/2000 | Nash et al. |
| 6,090,118 A | 7/2000 | McGuckin, Jr. |
| 6,102,890 A | 8/2000 | Stivland et al. |
| 6,102,933 A | 8/2000 | Lee et al. |
| 6,107,004 A | 8/2000 | Donadio, III |
| 6,114,653 A | 9/2000 | Gustafson |
| 6,146,370 A | 11/2000 | Barbut |
| 6,146,396 A | 11/2000 | Konya et al. |
| 6,149,682 A | 11/2000 | Frid |
| 6,165,199 A | 12/2000 | Barbut |
| 6,165,292 A | 12/2000 | Abrams et al. |
| 6,168,622 B1 | 1/2001 | Mazzocchi |
| 6,174,330 B1 | 1/2001 | Stinson |
| 6,203,561 B1 | 3/2001 | Ramee et al. |
| 6,227,436 B1 | 5/2001 | Nishikawa et al. |
| 6,237,460 B1 | 5/2001 | Frid |
| 6,241,691 B1 | 6/2001 | Ferrera et al. |
| 6,254,633 B1 | 7/2001 | Pinchuk et al. |
| 6,258,115 B1 | 7/2001 | Dubrul |
| 6,262,390 B1 | 7/2001 | Goland |
| 6,290,721 B1 | 9/2001 | Heath |
| 6,346,117 B1 | 2/2002 | Greenhalgh |
| 6,348,063 B1 | 2/2002 | Yassour et al. |
| 6,350,271 B1 | 2/2002 | Kurz et al. |
| 6,369,355 B1 | 4/2002 | Saunders |
| 6,375,668 B1 | 4/2002 | Gifford et al. |
| 6,383,204 B1 | 5/2002 | Ferrera |
| 6,383,205 B1 | 5/2002 | Samson et al. |
| 6,391,044 B1 | 5/2002 | Yadav et al. |
| 6,395,014 B1 | 5/2002 | Macoviak et al. |
| 6,428,558 B1 | 8/2002 | Jones et al. |
| 6,447,531 B1 | 9/2002 | Amplatz |
| 6,482,217 B1 | 11/2002 | Pintor et al. |
| 6,506,204 B2 | 1/2003 | Mazzocchi |
| 6,511,492 B1 | 1/2003 | Rosenbluth et al. |
| 6,511,504 B1 | 1/2003 | Lau et al. |
| 6,514,273 B1 | 2/2003 | Voss et al. |
| 6,517,888 B1 | 2/2003 | Weber |
| 6,521,865 B1 | 2/2003 | Jones et al. |
| 6,530,935 B2 | 3/2003 | Wensel et al. |
| 6,530,939 B1 | 3/2003 | Hopkins et al. |
| 6,540,722 B1 | 4/2003 | Boyle et al. |
| 6,544,276 B1 | 4/2003 | Azizi |
| 6,544,279 B1 | 4/2003 | Hopkins et al. |
| 6,554,848 B2 | 4/2003 | Boylan et al. |
| 6,563,080 B2 | 5/2003 | Shapovalov et al. |
| 6,569,183 B1 | 5/2003 | Kim et al. |
| 6,585,755 B2 | 7/2003 | Jackson et al. |
| 6,589,263 B1 | 7/2003 | Hopkins et al. |
| 6,589,265 B1 | 7/2003 | Palmer et al. |
| 6,602,264 B1 | 8/2003 | McGuckin, Jr. |
| 6,605,111 B2 | 8/2003 | Bose et al. |
| 6,610,077 B1 | 8/2003 | Hancock et al. |
| 6,612,012 B2 | 9/2003 | Mitelberg et al. |
| 6,626,936 B2 | 9/2003 | Stinson |
| 6,635,070 B2 | 10/2003 | Leeflang et al. |
| 6,652,576 B1 | 11/2003 | Stalker |
| 6,666,882 B1 | 12/2003 | Bose et al. |
| 6,669,721 B1 | 12/2003 | Bose et al. |
| 6,673,089 B1 | 1/2004 | Yassour et al. |
| 6,679,893 B1 | 1/2004 | Tran |
| 6,682,546 B2 | 1/2004 | Amplatz |
| 6,689,986 B2 | 2/2004 | Patel et al. |
| 6,692,504 B2 | 2/2004 | Kurz et al. |
| 6,695,813 B1 * | 2/2004 | Boyle et al. .................. 604/106 |
| 6,696,666 B2 | 2/2004 | Merdan et al. |
| 6,696,667 B1 | 2/2004 | Flanagan |
| 6,710,285 B2 | 3/2004 | Brown et al. |
| 6,719,934 B2 | 4/2004 | Stinson |
| 6,740,112 B2 | 5/2004 | Yodfat et al. |
| 6,749,560 B1 | 6/2004 | Konstorum et al. |
| 6,749,619 B2 | 6/2004 | Ouriel et al. |
| 6,773,448 B2 * | 8/2004 | Kusleika et al. ............. 606/200 |
| 6,777,647 B1 | 8/2004 | Messal et al. |
| 6,818,063 B1 | 11/2004 | Kerrigan |
| 6,837,901 B2 | 1/2005 | Rabkin et al. |
| 6,840,950 B2 * | 1/2005 | Stanford et al. ............. 606/200 |
| 6,844,603 B2 | 1/2005 | Georgakos et al. |
| 6,849,081 B2 | 2/2005 | Sepetka et al. |
| 6,855,153 B2 | 2/2005 | Saadat |
| 6,855,909 B2 | 2/2005 | Patel et al. |

(56) References Cited

U.S. PATENT DOCUMENTS

| | | |
|---|---|---|
| 6,861,615 B2 | 3/2005 | Wojcik et al. |
| 6,862,794 B2 | 3/2005 | Hopkins |
| 6,867,389 B2 | 3/2005 | Shapovalov et al. |
| 6,920,677 B2 | 7/2005 | Dolan et al. |
| 6,927,359 B2 | 8/2005 | Kleine et al. |
| 6,953,472 B2 | 10/2005 | Palmer et al. |
| 6,964,670 B1 | 11/2005 | Shah et al. |
| 6,977,355 B2 | 12/2005 | Duley et al. |
| 7,004,954 B1 | 2/2006 | Voss et al. |
| 7,018,401 B1 | 3/2006 | Hyodoh et al. |
| 7,029,494 B2 | 4/2006 | Soun et al. |
| 7,038,334 B2 | 5/2006 | Botos et al. |
| 7,093,416 B2 | 8/2006 | Johnson et al. |
| 7,093,527 B2 | 8/2006 | Rapaport et al. |
| 7,105,003 B2 | 9/2006 | Hiltebrandt |
| 7,128,073 B1 | 10/2006 | van der Burg et al. |
| 7,128,752 B2 | 10/2006 | Bales |
| 7,131,986 B2 * | 11/2006 | Sirhan et al. .............. 606/194 |
| 7,135,039 B2 | 11/2006 | De Scheerder et al. |
| 7,152,605 B2 | 12/2006 | Khairkhahan et al. |
| 7,172,614 B2 | 2/2007 | Boyle et al. |
| 7,179,273 B1 | 2/2007 | Palmer et al. |
| 7,211,109 B2 | 5/2007 | Thompson |
| 7,252,680 B2 | 8/2007 | Freitag |
| 7,306,618 B2 | 12/2007 | Demond et al. |
| 7,306,624 B2 | 12/2007 | Yodfat et al. |
| 7,344,546 B2 | 3/2008 | Wulfman et al. |
| 7,374,564 B2 | 5/2008 | Brown |
| 7,381,198 B2 | 6/2008 | Noriega et al. |
| 7,462,192 B2 | 12/2008 | Norton et al. |
| 7,476,034 B2 | 1/2009 | Shedlov et al. |
| 7,572,290 B2 | 8/2009 | Yodfat et al. |
| 7,582,101 B2 | 9/2009 | Jones et al. |
| 7,588,597 B2 | 9/2009 | Frid |
| 7,618,434 B2 | 11/2009 | Santra et al. |
| 7,621,870 B2 | 11/2009 | Berrada et al. |
| 7,622,070 B2 | 11/2009 | Atladottir et al. |
| 7,651,514 B2 | 1/2010 | Salahieh et al. |
| 7,669,799 B2 | 3/2010 | Elzey et al. |
| 7,735,493 B2 | 6/2010 | van der Burg et al. |
| 7,763,011 B2 | 7/2010 | Ortiz et al. |
| 7,780,646 B2 | 8/2010 | Farnholtz |
| 7,786,406 B2 | 8/2010 | Flanagan |
| 7,828,790 B2 | 11/2010 | Griffin |
| 7,837,726 B2 | 11/2010 | Von Oepen et al. |
| 7,857,844 B2 | 12/2010 | Norton et al. |
| 7,875,050 B2 | 1/2011 | Samson et al. |
| 7,879,062 B2 | 2/2011 | Galdonik et al. |
| 7,892,188 B2 | 2/2011 | Walker et al. |
| 7,922,732 B2 | 4/2011 | Mazzocchi et al. |
| 7,942,925 B2 | 5/2011 | Yodfat et al. |
| 7,955,345 B2 | 6/2011 | Kucharczyk et al. |
| 7,955,449 B2 | 6/2011 | Prokoshkin et al. |
| 7,971,333 B2 | 7/2011 | Gale et al. |
| 7,989,042 B2 * | 8/2011 | Obara et al. .............. 428/36.9 |
| 8,003,157 B2 | 8/2011 | Andreacchi et al. |
| 8,043,326 B2 | 10/2011 | Hancock et al. |
| 8,044,322 B2 | 10/2011 | Merdan |
| 8,052,640 B2 | 11/2011 | Fiorella et al. |
| 8,088,140 B2 | 1/2012 | Ferrera et al. |
| 8,092,483 B2 | 1/2012 | Galdonik et al. |
| 8,092,486 B2 | 1/2012 | Berrada et al. |
| 8,092,508 B2 | 1/2012 | Leynov et al. |
| 8,142,456 B2 | 3/2012 | Rosqueta et al. |
| 8,147,534 B2 | 4/2012 | Berez et al. |
| 8,152,833 B2 | 4/2012 | Zaver et al. |
| 8,157,833 B2 | 4/2012 | Au et al. |
| 8,192,484 B2 | 6/2012 | Frid |
| 8,217,303 B2 | 7/2012 | Baxter et al. |
| 8,236,042 B2 | 8/2012 | Berez et al. |
| 8,257,421 B2 | 9/2012 | Berez et al. |
| 8,261,648 B1 | 9/2012 | Marchand et al. |
| 8,267,985 B2 | 9/2012 | Garcia et al. |
| 8,267,986 B2 | 9/2012 | Berez et al. |
| 8,273,101 B2 | 9/2012 | Garcia et al. |
| 8,278,593 B2 | 10/2012 | Bialas et al. |
| 8,308,712 B2 | 11/2012 | Provost et al. |
| RE43,882 E | 12/2012 | Hopkins et al. |
| 8,333,796 B2 | 12/2012 | Tompkins et al. |
| 8,333,897 B2 | 12/2012 | Bialas et al. |
| 8,361,095 B2 | 1/2013 | Osborne |
| 8,361,138 B2 | 1/2013 | Adams |
| 8,394,119 B2 | 3/2013 | Zaver et al. |
| 8,398,670 B2 | 3/2013 | Amplatz et al. |
| 8,398,701 B2 | 3/2013 | Berez et al. |
| 8,409,114 B2 | 4/2013 | Parins |
| 8,409,267 B2 | 4/2013 | Berez et al. |
| 8,409,269 B2 | 4/2013 | Berez et al. |
| 8,409,270 B2 | 4/2013 | Clerc et al. |
| 8,419,658 B2 | 4/2013 | Eskuri |
| 8,419,787 B2 | 4/2013 | Yodfat et al. |
| 8,444,668 B2 | 5/2013 | Jones et al. |
| 8,500,788 B2 | 8/2013 | Berez et al. |
| 8,529,614 B2 | 9/2013 | Berez et al. |
| 8,617,234 B2 | 12/2013 | Garcia et al. |
| 8,623,067 B2 | 1/2014 | Berez et al. |
| 8,623,071 B2 | 1/2014 | Lundkvist et al. |
| 8,628,564 B2 | 1/2014 | Berez et al. |
| 8,679,150 B1 | 3/2014 | Janardhan et al. |
| 8,690,907 B1 | 4/2014 | Janardhan et al. |
| 8,715,314 B1 | 5/2014 | Janardhan et al. |
| 8,715,315 B1 | 5/2014 | Janardhan et al. |
| 8,715,316 B1 | 5/2014 | Janardhan et al. |
| 8,715,317 B1 | 5/2014 | Janardhan et al. |
| 8,721,676 B1 | 5/2014 | Janardhan et al. |
| 8,721,677 B1 | 5/2014 | Janardhan et al. |
| 8,728,116 B1 | 5/2014 | Janardhan et al. |
| 8,728,117 B1 | 5/2014 | Janardhan et al. |
| 8,733,618 B1 | 5/2014 | Janardhan et al. |
| 8,735,777 B1 | 5/2014 | Janardhan et al. |
| 8,747,432 B1 | 6/2014 | Janardhan et al. |
| 8,753,371 B1 | 6/2014 | Janardhan et al. |
| 8,828,045 B1 | 9/2014 | Janardhan et al. |
| 8,845,678 B1 | 9/2014 | Janardhan et al. |
| 8,845,679 B1 | 9/2014 | Janardhan et al. |
| 8,852,227 B1 | 10/2014 | Janardhan et al. |
| 8,859,934 B1 | 10/2014 | Janardhan et al. |
| 8,863,631 B1 | 10/2014 | Janardhan et al. |
| 8,866,049 B1 | 10/2014 | Janardhan et al. |
| 8,869,670 B1 | 10/2014 | Janardhan et al. |
| 8,870,901 B1 | 10/2014 | Janardhan et al. |
| 8,870,910 B1 | 10/2014 | Janardhan et al. |
| 8,872,068 B1 | 10/2014 | Janardhan et al. |
| 8,874,434 B2 | 10/2014 | Collobert et al. |
| 8,882,797 B2 | 11/2014 | Janardhan et al. |
| 8,895,891 B2 | 11/2014 | Janardhan et al. |
| 8,904,914 B2 | 12/2014 | Janardhan et al. |
| 2001/0031980 A1 | 10/2001 | Wensel et al. |
| 2002/0010487 A1 | 1/2002 | Evans et al. |
| 2002/0052638 A1 | 5/2002 | Zadno-Azizi |
| 2002/0082558 A1 | 6/2002 | Samson et al. |
| 2002/0091355 A1 | 7/2002 | Hayden |
| 2002/0099436 A1 | 7/2002 | Thornton et al. |
| 2002/0111648 A1 | 8/2002 | Kusleika et al. |
| 2002/0133111 A1 | 9/2002 | Shadduck |
| 2002/0143349 A1 | 10/2002 | Gifford, III et al. |
| 2002/0188314 A1 | 12/2002 | Anderson et al. |
| 2002/0194670 A1 | 12/2002 | Hashemi |
| 2002/0198550 A1 | 12/2002 | Nash et al. |
| 2002/0198589 A1 | 12/2002 | Leong |
| 2003/0065356 A1 | 4/2003 | Tsugita et al. |
| 2003/0097094 A1 | 5/2003 | Ouriel et al. |
| 2003/0097710 A1 | 5/2003 | Adrian |
| 2003/0100945 A1 | 5/2003 | Yodfat et al. |
| 2003/0114919 A1 | 6/2003 | McQuiston et al. |
| 2003/0135265 A1 | 7/2003 | Stinson |
| 2003/0176884 A1 | 9/2003 | Berrada et al. |
| 2003/0225448 A1 | 12/2003 | Gerberding |
| 2003/0226833 A1 | 12/2003 | Shapovalov et al. |
| 2004/0004061 A1 | 1/2004 | Merdan |
| 2004/0004063 A1 | 1/2004 | Merdan |
| 2004/0024416 A1 | 2/2004 | Yodfat et al. |
| 2004/0044391 A1 | 3/2004 | Porter |
| 2004/0073293 A1 | 4/2004 | Thompson |

(56) References Cited

U.S. PATENT DOCUMENTS

| | | |
|---|---|---|
| 2004/0073300 A1 | 4/2004 | Chouinard et al. |
| 2004/0088037 A1 | 5/2004 | Machreiner et al. |
| 2004/0093015 A1 | 5/2004 | Ogle |
| 2004/0098023 A1 | 5/2004 | Lee et al. |
| 2004/0098033 A1 | 5/2004 | Leeflang et al. |
| 2004/0118902 A1 | 6/2004 | Adams |
| 2004/0167613 A1 | 8/2004 | Yodfat et al. |
| 2004/0168298 A1 | 9/2004 | Dolan et al. |
| 2004/0193140 A1 | 9/2004 | Griffin et al. |
| 2004/0204737 A1 | 10/2004 | Boismier et al. |
| 2004/0220610 A1 | 11/2004 | Kreidler et al. |
| 2004/0225186 A1 | 11/2004 | Horne, Jr. et al. |
| 2004/0236412 A1 | 11/2004 | Brar et al. |
| 2005/0015110 A1 | 1/2005 | Fogarty et al. |
| 2005/0021075 A1 | 1/2005 | Bonnette et al. |
| 2005/0050624 A1 | 3/2005 | Pangramuyen |
| 2005/0120471 A1 | 6/2005 | Lim |
| 2005/0124969 A1 | 6/2005 | Fitzgerald et al. |
| 2005/0131522 A1 | 6/2005 | Stinson et al. |
| 2005/0133486 A1 | 6/2005 | Baker et al. |
| 2005/0149108 A1 | 7/2005 | Cox |
| 2005/0192624 A1 | 9/2005 | Mazzocchi et al. |
| 2005/0203553 A1 | 9/2005 | Maschke |
| 2005/0228417 A1 | 10/2005 | Teitelbaum et al. |
| 2005/0234474 A1 | 10/2005 | DeMello et al. |
| 2005/0236911 A1 | 10/2005 | Botos et al. |
| 2005/0251200 A1 | 11/2005 | Porter |
| 2005/0256563 A1 | 11/2005 | Clerc et al. |
| 2005/0267510 A1 | 12/2005 | Razack |
| 2005/0277975 A1 | 12/2005 | Saadat et al. |
| 2005/0283186 A1 | 12/2005 | Berrada et al. |
| 2006/0004346 A1 | 1/2006 | Begg |
| 2006/0009799 A1 | 1/2006 | Kleshinski et al. |
| 2006/0020286 A1 | 1/2006 | Niermann |
| 2006/0030878 A1 | 2/2006 | Anderson et al. |
| 2006/0047286 A1 | 3/2006 | West |
| 2006/0070516 A1 | 4/2006 | McCullagh et al. |
| 2006/0100687 A1 | 5/2006 | Fahey et al. |
| 2006/0116712 A1 | 6/2006 | Sepetka et al. |
| 2006/0116713 A1 | 6/2006 | Sepetka et al. |
| 2006/0136043 A1 | 6/2006 | Cully et al. |
| 2006/0161198 A1 | 7/2006 | Sakai et al. |
| 2006/0161253 A1 | 7/2006 | Lesh |
| 2006/0206196 A1 | 9/2006 | Porter |
| 2006/0206200 A1 | 9/2006 | Garcia et al. |
| 2006/0229638 A1 | 10/2006 | Abrams et al. |
| 2006/0229645 A1 | 10/2006 | Bonnette et al. |
| 2006/0241739 A1 | 10/2006 | Besselink et al. |
| 2006/0264904 A1 | 11/2006 | Kerby et al. |
| 2006/0276887 A1 | 12/2006 | Brady et al. |
| 2007/0016233 A1 | 1/2007 | Ferrera et al. |
| 2007/0027522 A1 | 2/2007 | Chang et al. |
| 2007/0060880 A1 | 3/2007 | Gregorich et al. |
| 2007/0060942 A2 | 3/2007 | Zadno-Azizi |
| 2007/0112381 A1 | 5/2007 | Figulla et al. |
| 2007/0118165 A1 | 5/2007 | DeMello et al. |
| 2007/0135833 A1 | 6/2007 | Talpade et al. |
| 2007/0142903 A1 | 6/2007 | Dave |
| 2007/0168019 A1 | 7/2007 | Amplatz et al. |
| 2007/0173921 A1 | 7/2007 | Wholey et al. |
| 2007/0185500 A1 | 8/2007 | Martin et al. |
| 2007/0185501 A1 | 8/2007 | Martin et al. |
| 2007/0197103 A1 | 8/2007 | Martin et al. |
| 2007/0198029 A1 | 8/2007 | Martin et al. |
| 2007/0198030 A1 | 8/2007 | Martin et al. |
| 2007/0225749 A1 | 9/2007 | Martin et al. |
| 2007/0228023 A1 | 10/2007 | Kleine et al. |
| 2007/0233174 A1 | 10/2007 | Hocking et al. |
| 2007/0265656 A1 | 11/2007 | Amplatz et al. |
| 2007/0288054 A1 | 12/2007 | Tanaka et al. |
| 2008/0027356 A1 | 1/2008 | Chen et al. |
| 2008/0033475 A1 | 2/2008 | Meng |
| 2008/0065008 A1 | 3/2008 | Barbut et al. |
| 2008/0077119 A1 | 3/2008 | Snyder et al. |
| 2008/0097393 A1 | 4/2008 | Chen |
| 2008/0097395 A1 | 4/2008 | Adams et al. |
| 2008/0097398 A1 | 4/2008 | Mitelberg et al. |
| 2008/0107641 A1 | 5/2008 | Kuebler |
| 2008/0195230 A1 | 8/2008 | Quijano et al. |
| 2008/0221601 A1 | 9/2008 | Huynh et al. |
| 2008/0228209 A1 | 9/2008 | DeMello et al. |
| 2008/0234722 A1 | 9/2008 | Bonnette et al. |
| 2008/0262487 A1 | 10/2008 | Wensel et al. |
| 2008/0269774 A1 | 10/2008 | Garcia et al. |
| 2008/0275464 A1 | 11/2008 | Abrams et al. |
| 2008/0294181 A1 | 11/2008 | Wensel et al. |
| 2008/0296274 A1 | 12/2008 | Bialas et al. |
| 2008/0300673 A1 | 12/2008 | Clerc et al. |
| 2008/0306499 A1 | 12/2008 | Katoh et al. |
| 2008/0312681 A1 | 12/2008 | Ansel et al. |
| 2009/0036833 A1 | 2/2009 | Parins |
| 2009/0043283 A1 | 2/2009 | Turnlund et al. |
| 2009/0062841 A1 | 3/2009 | Amplatz et al. |
| 2009/0076540 A1 | 3/2009 | Marks et al. |
| 2009/0082800 A1 | 3/2009 | Janardhan |
| 2009/0099647 A1 | 4/2009 | Glimsdale et al. |
| 2009/0105737 A1 | 4/2009 | Fulkerson et al. |
| 2009/0105753 A1 | 4/2009 | Greenhalgh et al. |
| 2009/0112251 A1 | 4/2009 | Qian et al. |
| 2009/0125097 A1 | 5/2009 | Bruszewski et al. |
| 2009/0157048 A1 | 6/2009 | Sutermeister et al. |
| 2009/0172935 A1 | 7/2009 | Anderson et al. |
| 2009/0188269 A1 | 7/2009 | Attarwala et al. |
| 2009/0198269 A1 | 8/2009 | Hannes et al. |
| 2009/0208385 A1 | 8/2009 | Howorth et al. |
| 2009/0221995 A1 | 9/2009 | Harlan |
| 2009/0248071 A1 | 10/2009 | Saint et al. |
| 2009/0264985 A1 | 10/2009 | Bruszewski |
| 2009/0275974 A1 | 11/2009 | Marchand et al. |
| 2009/0287120 A1 | 11/2009 | Ferren et al. |
| 2009/0297582 A1 | 12/2009 | Meyer et al. |
| 2009/0306702 A1 | 12/2009 | Miloslavski et al. |
| 2009/0306762 A1 | 12/2009 | McCullagh et al. |
| 2009/0312834 A1 | 12/2009 | Wood et al. |
| 2009/0318892 A1 | 12/2009 | Aboytes et al. |
| 2010/0010622 A1 | 1/2010 | Lowe et al. |
| 2010/0023034 A1 | 1/2010 | Linder et al. |
| 2010/0023105 A1 | 1/2010 | Levy et al. |
| 2010/0030256 A1 | 2/2010 | Dubrul et al. |
| 2010/0049240 A1 | 2/2010 | Papp |
| 2010/0069882 A1 | 3/2010 | Jennings et al. |
| 2010/0069948 A1 | 3/2010 | Veznedaroglu et al. |
| 2010/0114017 A1 | 5/2010 | Lenker et al. |
| 2010/0131000 A1 | 5/2010 | DeMello et al. |
| 2010/0152834 A1 | 6/2010 | Hannes et al. |
| 2010/0191319 A1 | 7/2010 | Lilburn et al. |
| 2010/0193485 A1 | 8/2010 | Anukhin et al. |
| 2010/0217276 A1 | 8/2010 | Garrison et al. |
| 2010/0217303 A1 | 8/2010 | Goodwin |
| 2010/0230391 A1 | 9/2010 | Baxter et al. |
| 2010/0262221 A1 | 10/2010 | Schafer et al. |
| 2010/0280592 A1 | 11/2010 | Shin et al. |
| 2010/0318097 A1 | 12/2010 | Ferrera et al. |
| 2011/0036820 A1 | 2/2011 | Merdan |
| 2011/0046719 A1 | 2/2011 | Frid |
| 2011/0056350 A1 | 3/2011 | Gale et al. |
| 2011/0060359 A1 | 3/2011 | Hannes et al. |
| 2011/0060400 A1 | 3/2011 | Oepen et al. |
| 2011/0077620 A1 | 3/2011 | deBeer |
| 2011/0082493 A1 | 4/2011 | Samson et al. |
| 2011/0087147 A1 | 4/2011 | Garrison et al. |
| 2011/0125132 A1 | 5/2011 | Krolik et al. |
| 2011/0125181 A1 | 5/2011 | Brady et al. |
| 2011/0152993 A1 | 6/2011 | Marchand et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0190797 A1 | 8/2011 | Fulkerson et al. |
| 2011/0190868 A1 | 8/2011 | Ducke et al. |
| 2011/0203446 A1 | 8/2011 | Dow et al. |
| 2011/0208227 A1 | 8/2011 | Becking |
| 2011/0210108 A1 | 9/2011 | Bialas et al. |
| 2011/0213403 A1 | 9/2011 | Aboytes |
| 2011/0238041 A1 | 9/2011 | Lim et al. |

(56) References Cited

U.S. PATENT DOCUMENTS

| | | |
|---|---|---|
| 2011/0265943 A1 | 11/2011 | Rosqueta et al. |
| 2011/0283871 A1 | 11/2011 | Adams |
| 2011/0295359 A1 | 12/2011 | Clerc et al. |
| 2011/0307072 A1 | 12/2011 | Anderson et al. |
| 2012/0022579 A1 | 1/2012 | Fulton |
| 2012/0029616 A1 | 2/2012 | Guerriero et al. |
| 2012/0055614 A1 | 3/2012 | Hancock et al. |
| 2012/0057813 A1 | 3/2012 | Von Oepen |
| 2012/0065660 A1 | 3/2012 | Ferrera et al. |
| 2012/0083824 A1 | 4/2012 | Berrada et al. |
| 2012/0116443 A1 | 5/2012 | Ferrera et al. |
| 2012/0158124 A1 | 6/2012 | Zaver et al. |
| 2012/0164157 A1 | 6/2012 | Kuebler |
| 2012/0179192 A1 | 7/2012 | Fogarty et al. |
| 2012/0197283 A1 | 8/2012 | Marchand et al. |
| 2012/0209312 A1 | 8/2012 | Aggerholm et al. |
| 2012/0231414 A1 | 9/2012 | Johnson |
| 2012/0232655 A1 | 9/2012 | Lorrison et al. |
| 2012/0239066 A1 | 9/2012 | Levine et al. |
| 2012/0239074 A1 | 9/2012 | Aboytes et al. |
| 2012/0245517 A1 | 9/2012 | Tegels |
| 2012/0259404 A1 | 10/2012 | Tieu et al. |
| 2012/0265238 A1 | 10/2012 | Hopkins et al. |
| 2012/0271337 A1 | 10/2012 | Figulla et al. |
| 2012/0271403 A1 | 10/2012 | Gries |
| 2012/0273467 A1 | 11/2012 | Baxter et al. |
| 2012/0277850 A1 | 11/2012 | Bertini |
| 2012/0283768 A1 | 11/2012 | Cox et al. |
| 2012/0290067 A1 | 11/2012 | Cam et al. |
| 2012/0316598 A1 | 12/2012 | Becking et al. |
| 2012/0330347 A1 | 12/2012 | Becking et al. |
| 2013/0030460 A1 | 1/2013 | Marks et al. |
| 2013/0060323 A1 | 3/2013 | McHugo |
| 2013/0066357 A1 | 3/2013 | Aboytes et al. |
| 2013/0085515 A1 | 4/2013 | To et al. |
| 2013/0096587 A1 | 4/2013 | Smith et al. |
| 2013/0138136 A1 | 5/2013 | Beckham et al. |
| 2013/0167960 A1 | 7/2013 | Pethe et al. |
| 2013/0220610 A1 | 8/2013 | Mosing et al. |
| 2013/0240096 A1 | 9/2013 | Browne et al. |
| 2013/0261656 A1 | 10/2013 | Lorenzo |
| 2013/0327469 A1 | 12/2013 | Pingleton et al. |
| 2014/0128905 A1 | 5/2014 | Molaei |
| 2014/0155908 A1 | 6/2014 | Rosenbluth et al. |
| 2014/0324091 A1 | 10/2014 | Rosenbluth et al. |
| 2015/0028005 A1 | 1/2015 | Janardhan et al. |
| 2015/0032121 A1 | 1/2015 | Janardhan et al. |
| 2015/0032146 A1 | 1/2015 | Janardhan et al. |
| 2015/0032147 A1 | 1/2015 | Janardhan et al. |

FOREIGN PATENT DOCUMENTS

| | | |
|---|---|---|
| EP | 1 904 217 | 3/2013 |
| GB | 667071 | 2/1952 |
| WO | WO 2004/093738 | 11/2004 |
| WO | WO 2007/011353 | 1/2007 |

OTHER PUBLICATIONS

C. Sarti et al., International Trends in Mortality From Stroke, 1968 to 1994, http://stroke.ahajournals.org/, Apr. 20, 2000, pp. 1588-1601, 2000 American Heart Association, Inc.

H. Adams et al., Guidelines for the Early Management of Patients with Ischemic Stroke —A Scientific Statement from the Stroke Council of the American Stroke Association, http://stroke.ahajournals.org/, pp. 1056-1083, 2003 American Heart Association, Inc.

M. Rymer et al. Organizing regional networks to increase acute stroke intervention, Neurological Research, 2005, vol. 27, Supplement 1 pp. 59-516, 2005 W.S. Maney & Son Ltd.

A. Furlan et al., Intra-arterial Prourokinase for Acute Ischemic Stroke, The PROCT II Study: A Randomized Controlled Trial, JAMA, Dec. 1, 1999, vol. 282, No. 21, pp. 2003-2011, 1999 American Medical Association.

J. Yadav, Carotid stenting in high-risk patients: Design and rationale of the Sapphire trial, Cleveland Clinic Journal of Medicine, vol. 71, Supplement 1, Jan. 2004, pp. S45-S46.

A. Bose, a Novel, Self-Expanding, Nitinol Stent in Medically Refractory Intracranial Atherosclerotic Stenoses, The Wingspan Study, http://stroke.ahajournals.org/, pp. 1531-1537, 2007 American Heart Association, Inc.

Adams et al., "Guidelines for the Early Management of Patients with Ischemic Stroke —2005 Guidelines Update —A Scientific Statement from the Stroke Council of the American Stroke Association," Stroke, 2005, vol. 36, pp. 916-923.

Alligator Retrieval Device Product Brochure, 2009.

Braley et al., "Advancements in Braided Materials Technology," 46th Int'l Sample Symposium, May 2001, pp. 2445-2454.

U.S. Appl. No. 60/980,736, filed Oct. 17, 2007.
U.S. Appl. No. 61/044,392, filed Apr. 11, 2008.
U.S. Appl. No. 61/015,154, filed Dec. 19, 2007.
U.S. Appl. No. 60/989,422, filed Nov. 20, 2007.
U.S. Appl. No. 61/019,506, filed Jan. 7, 2008.
U.S. Appl. No. 60/987,384, filed Nov. 12, 2007.
U.S. Appl. No. 61/129,823, filed Jul. 22, 2008.
U.S. Appl. No. 61/202,612, filed Mar. 18, 2009.

"Retrieve—Don't Guess," Alligator™ Retrieval Device, Chestnut Medical Technologies, Inc.

"Alligator™ Retrieval Device (ARD)," Chestnut Medical Technologies, Inc.

H. Henkes, et al., "A New Device for Endovascular Coil Retrieval from Intracranial Vessels: Alligator Retrieval Device." AJRN Am J. Neuroradiol Feb. 2006, 27:327-329.

Jay S. Yadav, M.D., et al., "Protected Carotid-Artery Stenting versusEndarterectomy in High-Risk Patients." The New England Journal of Medicine, vol. 351, No. 15, Oct. 7, 2004, 1493-1567.

"Opening Possibilities", Cordis CarotidSystem.

"Diagnosing Carotid Artery Disease: The Leading Cause of Stroke, Cordis Endovascular, Sample News Article #1: Diagnosis.".

"Now Available in Rapid Exchange," Cordis CarotidSystem RX, Technical Specifications and Product Codes.d.

"2006 Clinical Update for Physicians," Xact® Carotid Stant System, RX Acculink® Carotid Stent System.

Concentric Micro Catheters, Concentric Medical.

"For every situation, every advantage," Cordis CarotidSystem, Technical Specifications and Product Codes.

"Design of Medical Devices conference," University of Minnesota, Apr. 17-19, 2007.

"Customized for Carotid Arteries, The Barewire Revolution is Here," Embo Shield.

"Redefining Confidence," ev3 Carotid innovations.

Excelsior 1018 Microcatheter, Neurovascular Access, Boston Scientific.

Excelsior "For Peak Performance in GDC Delivery," Boston Scientific.

"Excelsior SL-10 Micorcatheter," Boston Scientific.

"Excelsior SL-10 Microcatheter," Neurovascular Access, Boston Scientific.

"FilterWire EX™ , Embolic Protection System," Boston Scientific.

"Venture Capital and Private Equity Investing in Medical Devices and Healthcare Technologies," 6th Annual Med-Tech, May 16-17, 2007.

"Instructions for Use, Marci® Retriever X51X6," Concentric Medical.

"Mirage™ .008" Hydrophilic Guidwlre.

"Neuroform[2] ™ Microdelivery Stent Systems, Neurovascular Reconstruction," Boston Scientific.

"Neuroform[2]™ Microdelivery Stent System, Technical Bulletin No. 1—Parent Vessel Protection," Boston Scientific.

"Neuroform[3]™ Microdelivery Stent System, Confidence Begins with Control," Boston Scientific.

"Pre-Shaped Microcatheters, Product Selection Guide," Boston Scientific.

"Renegade® 18 Microcatheter, Neurovascuiar Access," Boston Scientific.

(56) References Cited

OTHER PUBLICATIONS

"Synchro® Guidewires, Neurovascular Access," Boston Scientific.
"Tracker® Excel™—14 Microcatheter, Neurovascuiar Access," Boston Scientific.
"Tracker® Excel™—14 Microcatheter, Engineered for GDC® Coil Delivery," Boston Scientific.
"Transend® Guidewires, Neurovascular Access," Boston Scientific.
"Let's Dance," Watusi™ Guidewire.
US 6,348,062, 02/2002, Hopkins et al. (withdrawn)

\* cited by examiner

DISTAL EMBOLIC PROTECTION DEVICES WITH A VARIABLE THICKNESS MICROGUIDEWIRE AND METHODS FOR THEIR USE

FIELD OF INVENTION

This invention is related generally to the field of intravascular medical devices. Particularly a distal embolic protection device as well as methods for use of the device during neurovascular interventional procedures in the cerebral arterial blood vessels.

BACKGROUND OF INVENTION

Stroke is the leading cause of long term disability in the United States and the second leading cause of death worldwide with over 4.4 million deaths in a year (1999).[1] There are over 700,000 new strokes every year in the United States.[2] Around 85% of all strokes are acute ischemic strokes caused from a blockage in a blood vessel or a blood clot occluding a blood vessel.[2] In 1996, the FDA approved a thrombolytic drug to dissolve blood clots called recombinant tissue plasminogen activator (r-tpa).[3] Despite practice guidelines from multiple national organizations stating the intravenous r-tpa is the standard of care for patients with acute ischemic stroke within 3 hours from symptom onset,[3] only 3-4% of patients with acute ischemic stroke received this drug in the United States.[4] Unlike intravenous r-tpa, Intra-arterial infusion of thrombolytic agents can be used for up to 6 hours from acute ischemic stroke symptom onset and could benefit more people.[5] Currently, intra-arterial infusion of thrombolytic agents are administered to a blood clot and the blood clot breaks up into smaller blood clots and travel downstream and potentially close up smaller cerebral blood vessels. With advances in regional stroke networks, there are more and more stroke patients who are getting access to intra-arterial thrombolysis and therapies, and are as high as 21.6%.[4] However, there is no currently available distal embolic protection device that is dedicated to the cerebral blood vessels.

More than 8% of all acute ischemic strokes are from blockages in the cervical or neck carotid artery.[2] Studies have shown that performing percutaneous balloon angioplasty and stenting on these blockages result in emboli or debris being dislodged downstream and could cause further strokes and therefore there have been large clinical trials of angioplasty and stenting of the carotid artery in the neck with distal embolic protection devices being used.[6] In addition to blockages in the neck region of the carotid artery, more than 8% of all acute ischemic strokes are due to blockages in the cerebral arterial blood vessels called intracranial stenosis.[2] Recently there has been a new device approved for intracranial angioplasty and stenting.[7] Although the risks of small emboli or debris being dislodged during intracranial angioplasty and stenting is similar to the cervical carotid artery and the rest of the body, there are no distal embolic protection devices in the market dedicated for cerebral arterial blood vessels. In addition, the distal embolic protection devices currently available for the cervical carotid artery are too bulky for use in the tortuous and fragile cerebral arterial blood vessels.

Embolic protection devices have been developed for the cervical carotid artery prior to carotid angioplasty and stenting.[6] However, these devices do not have a small profile for use in the cerebral arterial blood vessels and will not be able to track and traverse the tortuous cerebral arterial blood vessels.

Barbut in U.S. Pat. No. 6,165,199 has described embolic protection devices that can be used for the cerebral arterial blood vessels. This is a proximal embolic protection device wherein the embolic protection device is before the clot or blockage comprising of a proximal balloon occlusion catheter to create flow arrest and an aspiration device to suction out the emboli or debris during the interventional procedure in the cervical and cerebral blood vessels. The drawbacks of a proximal protection device are that the flow arrest performed to decrease emboli or debris from traveling downstream can be detrimental in itself, since creating a flow arrest in an already ischemic blood vessel during the long neurovascular interventional procedures would in itself worsen the cerebral ischemia and worsen the strokes. Bose et al in U.S. Pat. No. 6,669,721 describe thin-film distal embolic protection devices that can be potentially used in the cerebral blood vessels. The device has one or two rings and a thin-film filter that is attached to the guidewire. The drawbacks of this device is that during neurovascular interventional procedures, there is constant exchange of microcatheters, balloon catheters, and stent catheters over the guidewire or microguidewire, and a distal embolic protection device that is rigidly fixed to the guidewire or microguidewire would cause trauma to the cerebral arterial blood vessel wall as there will not be any mobility of the wire independent of the distal embolic protection device. Hopkins et al in U.S. Pat. No. 6,544,279 B1 describe distal embolic protection devices that do have mobility over a guidewire or microguidewire, however these guidewires or microguidewires are of uniform thickness and the mobile attachment point in these devices extend through the entire length of the device. Current microguidewires used in neurovascular interventional procedures to perform intracranial angioplasty and stenting among other procedures use microguidewires in the thickness of 0.014 inch (0.356 mm).[7] Current microcatheters used for intracranial cerebral blood vessel catheterization for stroke as well as during intracranial angioplasty and stenting have an inner diameter of about 0.017 inch (0.432 mm). Having a distal embolic protection device mounted on a uniform thickness microguidewire of a thickness of 0.014 inch (0.356 mm) will not permit the distal embolic protection device in the collapsed form to have a thin enough or small enough profile to be compatible with existing microcatheters that are 0.017 inch (0.432 mm) in inner diameter. Having a distal embolic protection device mounted on a uniform thickness microguidewire with a mobile attachment point that extends through the entire length of the device will increase the overall thickness of the device in the collapsed configuration thereby limiting the trackability of the device and inhibiting access to the tortuous and narrow cerebral arterial blood vessels.

BRIEF SUMMARY OF INVENTION

The present invention provides a distal embolic protection device that can be used for neurovascular interventional procedures including, but not limited to, intra-arterial thrombolytic or clot dissolving drug infusion for acute ischemic stroke, as well as percutaneous transluminal intracranial balloon angioplasty and stenting procedures for patients at risk for stroke so that the small emboli or debris that are dislodged during these procedures can be retrieved safely. The distal embolic protection device of this invention has a thin and small profile such that they are compatible with existing standard microcatheters. The distal embolic protection device of this invention is not attached to a balloon or stent. The present invention also addresses the limitations of all the prior art on embolic protection devices discussed above as well as those that have been referenced.

An object of this invention is to have a distal embolic protection device that is dedicated to the cerebral arterial blood vessels and is suitable for use in cerebral arterial blood vessels of 1.5 mm to 4.5 mm in diameter. The definition of cerebral arterial blood vessels is described in the detailed description of FIGS. 1, 2 and 3.

Another object of this invention is to have an embolic protection device that does not have to cause flow arrest to provide embolic protection. Devices that cause flow arrest have a risk of worsening a stroke. Therefore the embolic protection device of this invention is distal rather than proximal to the blockage or blood clot and not proximal to the blockage or blood clot.

Another object of this invention is to have a distal embolic protection device that can pass through the tortuous cerebral arterial blood vessels with no or little trauma to the vessels. Current embolic protection devices are transported or moved through catheters using a small stearable microwire. Due to the bulky nature of current embolic protection devices, it is very difficult to navigate through even in straight blood vessels leave alone tortuous blood vessels.

Another object of this invention is to have a distal embolic protection device comprising a collapsible filtering device that has a small thin profile so that in the collapsed configuration of the filtering device, the thickness of the distal embolic protection device is no more than about 0.017 inch (0.432 mm), preferably no more than about 0.014 inch (0.356 mm), and can be delivered and retrieved via a standard microcatheter (inner diameter of 0.017 inch, 0.432 mm), a balloon catheter or stent catheter that are used in neurovascular interventional procedures. The filtering device is not attached to a balloon or stent.

Another object of this invention is a distal embolic protection device comprising a variable thickness microguidewire and a collapsible filtering device, wherein the filtering device is rotatably mounted on the distal segment of the variable thickness microguidewire. The variable thickness microguidewire comprises a thinner segment bordered on both ends by thicker segments. The thinner segment is no more than about 0.010 inches in thickness and preferably about 0.008 to 0.010 inch (0.203 to 0.254 mm). The thicker segments, which make up the majority of the microguidewire, are thicker than the thinner segment and preferably no more than 0.017 inch (0.432 mm) in thickness, more preferably no more than about 0.014 inch (0.356 mm). The variable thickness microguidewire may comprise a core microguidewire that extends through the entire length, or a portion of, of the microguidewire and a coating or covering or flexible hypotube or a combination thereof over the core microguidewire. The filtering device is mounted on the thinner segment, which is in the distal segment of the microguidewire to maintain a small thin profile so that trackability is maintained as well as compatibility with existing microcatheters, balloon catheters and stent catheters that are used in neurovascular interventional procedures. Preferably the small thin profile is no more than about 0.017 inch (0.432 mm) and more preferably no more than about 0.014 inch (0.356 mm).

Another object of this invention is a distal embolic protection device comprising a variable thickness microguidewire and a filtering device, wherein the microguidewire and filtering device have rotational and longitudinal movement relative to and independently of each other, such that the filtering device can remain stable within the blood vessel while there is motion on the microguidewire both in the rotational as well as longitudinal directions relative to the filtering device so that there is no, or very limited, trauma to the fragile cerebral arterial blood vessels.

The filtering device of the distal embolic protection device of this invention may comprise mobile attachment points on its proximal and distal ends wherein the mobile attachment points attach the filtering device to the microguidewire. The mobile attachment points are of such a size that that the thickness of the filtering device in the collapsed configuration is smaller than a cerebral arterial blood vessel and can pass through standard microcatheters that are used in neurovascular interventional procedures. Preferably the attachment points in conjunction with the filtering device in the collapsed configuration are no more than about 0.017 in (0.432 mm), and more preferably not more than about 0.014 inch (0.356 mm) in thickness. Preferably the attachment points are short and abut, but do not cover, the thicker segments of the microguidewire.

In an embodiment of this invention, the distal embolic protection device comprises a filtering device rotatably mounted on the thinner segment of the microguidewire, and further comprises cylindrical coils that wind around the thinner segment of the microguidewire and connect the proximal and distal ends of the filtering device to the proximal and distal stops of the thicker segments of the microguidewire. The attached cylindrical coils decrease the shear stress on the thinner segment of the microguidewire during the retrieval of the distal embolic protection device.

Another object of this invention the distal embolic protection device comprises a radio-opaque portion that enables the device to be visualized during fluoroscopic neurovascular interventional procedures. For example, the thicker segments of the microguidewire, or the distal end of the microguidewire, or the filtering device itself may comprise radio-opaque sections so that the operator during a medical procedure can distinguish the filtering device and its position relative to the thicker and thinner segments of the microguidewire.

The distal embolic protection devices of this invention are dedicated to use in cerebral arterial blood vessels and their use in the treatment of existing stroke patients and patients that are at risk for strokes. The methods of this invention include e.g., crossing a vascular blockage or blood clot with a standard microcatheter and microwire. Then removing the microwire and once the microwire is removed, the distal embolic protection device is advanced via the microcatheter to the desired location. As the distal embolic protection device is not involved in navigation, it is able to pass the tortuous curves of the cerebral blood vessels due to the novel delivery system. The microguidewire is also designed to be compatible with existing microcatheters, balloon catheters and stent catheters used in neurovascular interventions. In addition, the stops in the distal part of the microguidewire and the mobile attachment points on the filtering device allow for mobility of the microguidewire both in the rotatory and longitudinal directions relative to the filtering device, wherein the filtering device is stable in the cerebral blood vessel thereby minimizing vessel trauma or dissections. The variable thickness of the distal part of the microguidewire also allows for the smaller overall profile of the device and improves its compatibility with existing microcatheters, balloon catheters, and stent catheters. The small profile also allows for easy retrieval of the distal embolic protection device of this invention using existing microcatheters, balloon catheters or stent catheters making the procedure shorter and safer.

The methods of this invention for collecting thrombo-embolic material, debris or clots released during percutaneous neurovascular interventional procedures specifically performed in the cerebral arterial blood vessels, comprises inserting the distal embolic protection device of this invention into a cerebral arterial blood vessel having an area of stenosis or a clot, deploying the filtering device distal to the area of blockage or clot and allowing the filtering device to expand to fill the diameter of the cerebral arterial blood vessel. The methods of this invention may further comprise advancing a standard microcatheter over a standard microwire across the area of stenosis or clot, positioning the microcatheter distal to the stenosis or clot, withdrawing the microwire, and advancing the distal embolic protection device through the standard microcatheter. The thickness of the thicker segments of the variable thickness microguidewire is no more than about 0.017 inch (0.432 mm) and preferably no more than about 0.014 inch (0.356 mm) such that it is compatible for use with standard microcatheters, which have an inner lumen diameter of about 0.017 inch (0.432 mm). In addition, the methods of this invention may further comprise withdrawing the microcatheter, while keeping the microguidewire in position distal to the stenosis or clot, unsheathing the distal embolic protection device and expanding the filtering device to the inside size of the cerebral arterial blood vessel, ranging from 1.5 mm to 4.5 mm, and wherein the expanded shape of the filter membrane is a hemispherical, helical or conical shape and spans the cerebral arterial blood vessel. The method may also comprise maintaining the microguidewire in position, exchanging the standard microcatheter for (1) a balloon catheter to perform balloon angioplasty of the cerebral arterial blood vessels, or (2) a stent catheter to perform stenting of the cerebral arterial blood vessels, and collecting any debris or clots that are dislodged during the balloon angioplasty and or stenting in the cerebral arterial blood vessels in the filter membrane. The methods of this invention also comprise maintaining the microguidewire in position and administering clot dissolving drugs or thrombolytics to a patient in need thereof through a standard microcatheter, such that any debris or clots that are dislodged will be collected by the filter membrane. The methods of this invention may comprise additional steps, e.g., recovering the distal embolic protection device by advancing a standard microcatheter, balloon catheter, or stent catheter over the variable thickness microguidewire, and withdrawing the distal embolic protection device and the standard microcatheter, balloon catheter or stent catheter.

Various embodiments of the present invention are shown in the figures and described in detail below.

BRIEF DESCRIPTION OF INVENTION/FIGURES

DETAILED DESCRIPTION OF INVENTION/FIGURES

Figure 1:
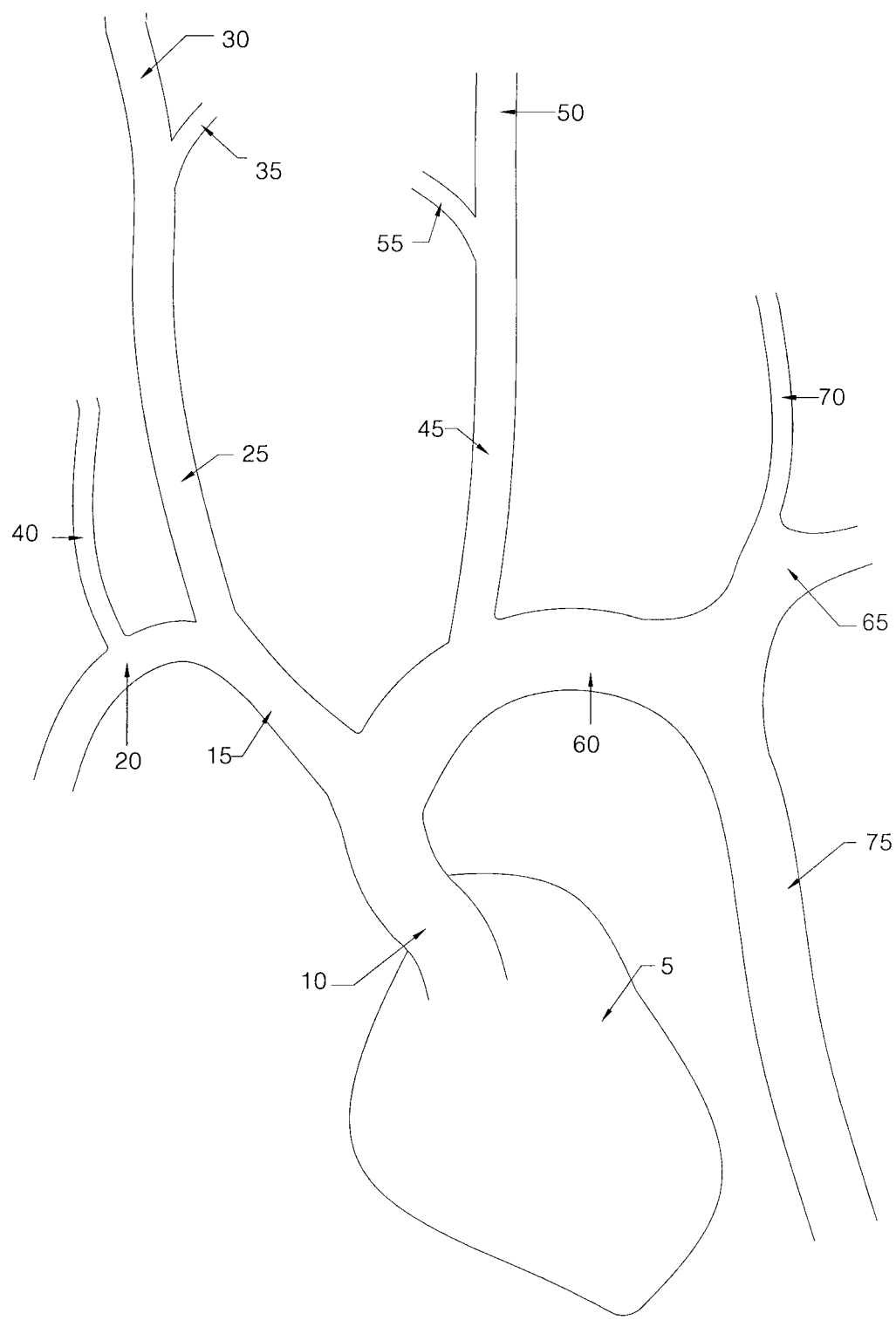
FIG. 1 is a schematic diagram illustrating the origin of the great vessels from the heart.

FIG. 1 is a schematic diagram that illustrates the heart, the aorta and the supra-aortic vessels. The left ventricle 5 is one of the chambers of the heart and pumps oxygenated blood to the rest of the body through the aorta 10. The innominate artery 15 is one of the great vessels originating from the aorta 10 and divides into two branches namely the right subclavian artery 20 and the right common carotid artery 25. The right common carotid artery 25 gives off the right internal carotid artery 30 that continues intracranially to supply the anterior circulation or the front of the brain (see FIG. 2 for further details), and the right external carotid artery 35 which continues to supply the scalp, face and neck. The right subclavian artery 20 gives off several branches including the right vertebral artery 40 which continues intracranially to supply the posterior circulation or the back of the brain (see FIG. 3 for further details). The next great vessel originating from the aorta 10 is the left common carotid artery 45. The left common carotid artery 45 divides into the left internal carotid artery 50, which continues intracranially to supply the anterior circulation or the front of the brain (see FIG. 2 for further details), and the left external carotid artery 55, which continues to supply the scalp, face and neck. This portion of the aorta 10 from which the left common carotid artery arises is also known as the aortic arch 60. The left subclavian artery 65 arises from the aortic arch 60 and gives off several branches including the left vertebral artery 70 which continues intracranially to supply the posterior circulation or the back of the brain (see FIG. 3 for further details). Subsequent to the origin of the left subclavian artery 65, the aortic arch curves inferiorly or downwards and is known as the descending aorta 75 which continues to supply the abdomen, spine and lower extremities.

Figure 2:
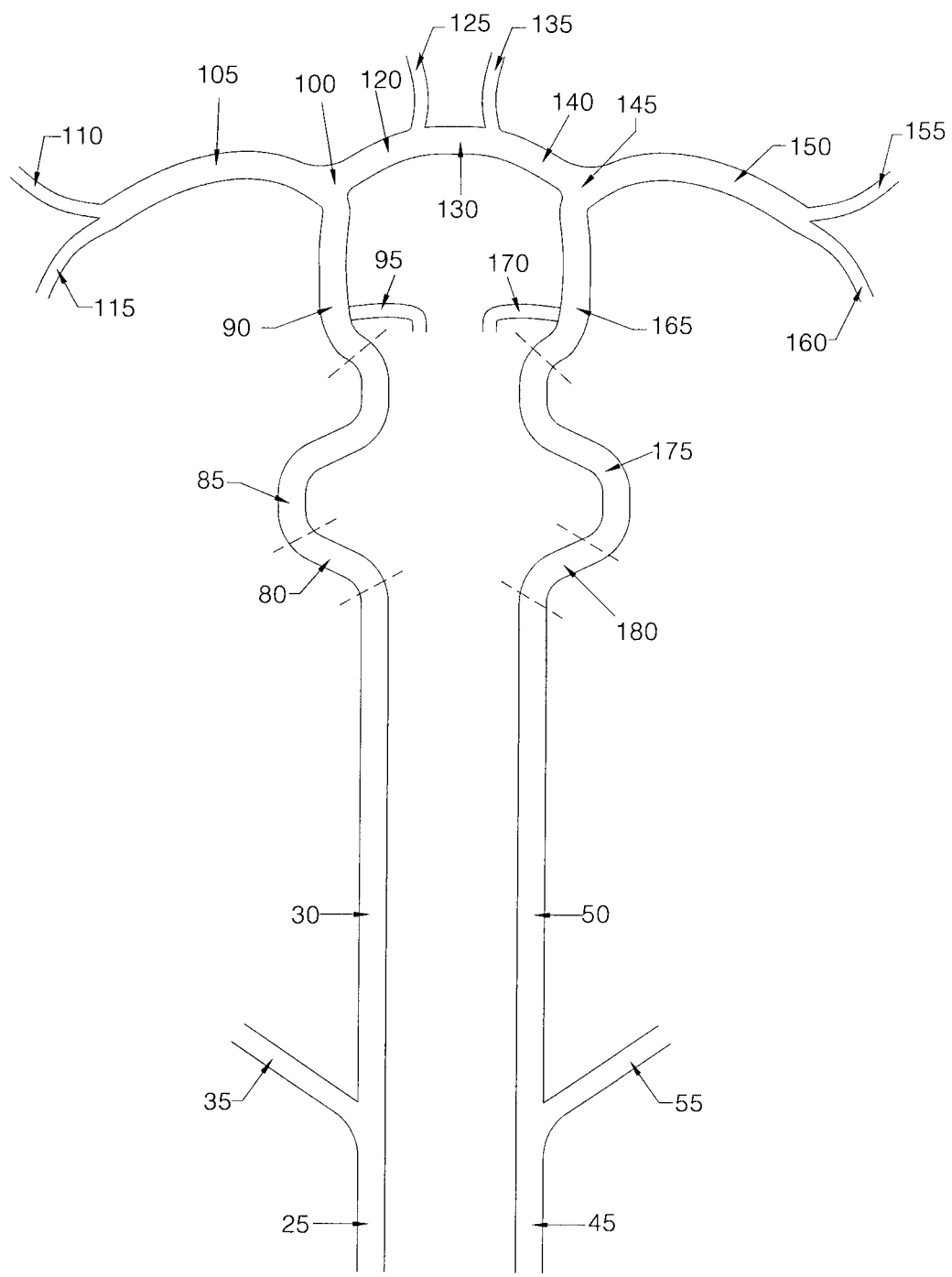
FIG. 2 is a schematic diagram illustrating the cervical and cerebral course of the internal carotid arteries and their branches.

FIG. 2 is a schematic diagram illustrating the cervical and intracranial course of the internal carotid arteries. The right common carotid artery 25 divides into the right external carotid artery 35 and the right cervical internal carotid artery 30 in the neck. The right internal carotid artery in the cervical or neck portion 30 enters the base of skull and continues as the petrous portion of the right internal carotid artery 80. The petrous portion of the right internal carotid artery 80 then continues as the tortuous cavernous portion of the right internal carotid artery 85. The right internal carotid artery then pierces the dura or covering layering of the brain to form the supraclinoid portion of the right internal carotid artery 90 and gives off the right posterior communicating artery 95 which helps form the circle of Willis or the collateral pathway to other blood vessels in the brain (see FIG. 4 for further details). The supraclinoid portion of the right internal carotid artery 90 then bifurcates 100 into the right middle cerebral artery 105 as well as the right anterior cerebral artery 120 at the right internal carotid artery bifurcation 100. The right middle cerebral artery divides into several branches and the main ones being the right middle cerebral artery superior division 110 and the right middle cerebral artery inferior division 115. The A1 segment of the right anterior cerebral artery 120 further continues as the A2 segment of the right anterior cerebral artery 125 and at the junction of the A1 and A2 segments gives off an important branch called the anterior communicating artery 130 that communicates with the blood vessels from the left side of the brain to also form the circle of Willis.

The left common carotid artery 45 divides into the left external carotid artery 55 and the left cervical internal carotid artery 50 in the neck. The left internal carotid artery in the cervical or neck portion 50 enters the base of skull and continues as the petrous portion of the left internal carotid artery 180. The petrous portion of the left internal carotid artery 180 then continues as the tortuous cavernous portion of the left internal carotid artery 175. The left internal carotid artery then pierces the dura or covering layering of the brain to form the supraclinoid portion of the left internal carotid artery 165 and gives off the left posterior communicating artery 170 which helps form the circle of Willis or the collateral pathway to other blood vessels in the brain. The supraclinoid portion of the left internal carotid artery 165 then bifurcates 145 into the left middle cerebral artery 150 as well as the left anterior cerebral artery 140 at the left internal carotid artery bifurcation 145. The left middle cerebral artery divides into several branches and the main ones being the left middle cerebral artery superior division 155 and the left middle cerebral artery inferior division 160. The A1 segment of the left anterior cerebral artery 140 further continues as the A2 segment of the left anterior cerebral artery 135 and at the junction of the A1 and A2 segments gives off an important branch called the anterior communicating artery 130 that communicates with the blood vessels from the right side of the brain to also form the circle of Willis.

In this invention, the internal carotid arteries from the petrous, cavernous and supraclinoid portions and their branches, along with the middle cerebral and anterior cerebral arteries and their branches are considered as cerebral arterial blood vessels (80 to 180).

Figure 3:
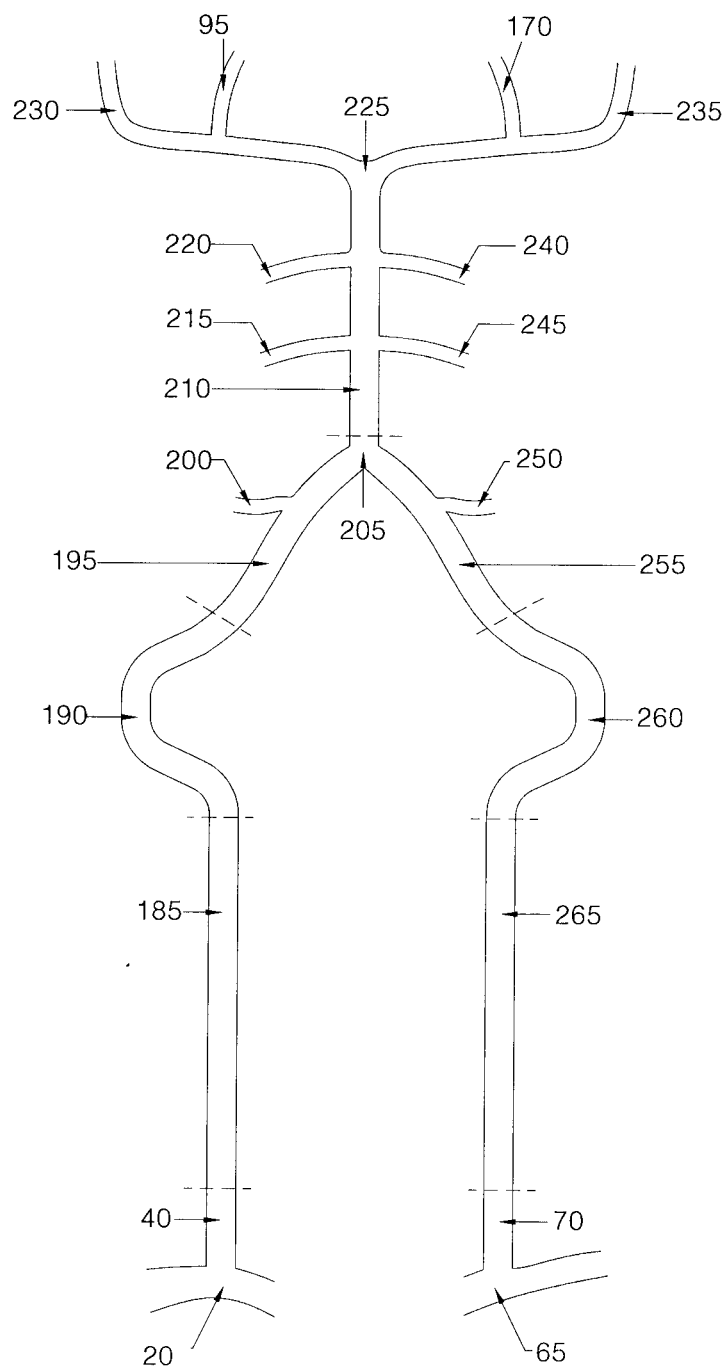
FIG. 3 is a schematic diagram illustrating the cervical and cerebral course of the vertebral arteries and their branches.

FIG. 3 is a schematic diagram illustrating the course of the bilateral vertebral arteries and their branches. The right vertebral artery 40 is a branch of the right subclavian artery 20. The first portion of the right vertebral artery in the cervical or neck portion is called the V1 segment of the right vertebral artery 40. The right vertebral artery continues in the neck as the V2 segment of the right vertebral artery 185 and travels close to the base of brain. It makes a tortuous curve and is called the V3 segment of the right vertebral artery 190 and finally pierces the dura or outer covering layer of the brain and forms the V4 segment of the right vertebral artery 195. The V4 segment of the right vertebral artery 195 gives off an important branch to the right cerebellum called the right posterior-inferior cerebellar artery 200 and then joins together with the V4 segment of the left vertebral artery 255 at the vertebro-basilar junction 205 to form the basilar artery 210. The basilar artery 210 gives off several branches including the bilateral anterior inferior cerebellar arteries 215 and 245, as well as, the bilateral superior cerebellar arteries 220 and 240, and then bifurcates at the basilar apex 225 into the bilateral posterior cerebral arteries 230 and 235. The right posterior communicating artery 95 communicates with the right posterior cerebral artery 230 (see FIG. 4 for further details). The left posterior communicating artery 170 communicates with the left posterior cerebral artery 235 (see FIG. 4 for further details). The left vertebral artery 70 is a branch of the left subclavian artery 65. The first portion of the left vertebral artery in the cervical or neck portion is called the V1 segment of the left vertebral artery 70. The left vertebral artery continues in the neck as the V2 segment of the left vertebral artery 265 and travels close to the base of brain. It makes a tortuous curve and is called the V3 segment of the left vertebral artery 260 and finally pierces the dura or outer covering layer of the brain and forms the V4 segment of the left vertebral artery 255. The V4 segment of the left vertebral artery 255 gives off an important branch to the left cerebellum called the left posterior-inferior cerebellar artery 250 and then joins together with the V4 segment of the right vertebral artery 195 at the vertebro-basilar junction 205 to form the basilar artery 210.

In this invention, the vertebral arteries from the V2, V3, and V4 segments and their branches, along with the basilar artery and the bilateral posterior cerebral arteries and their branches are also considered as cerebral arterial blood vessels (185 to 265).

Figure 4:
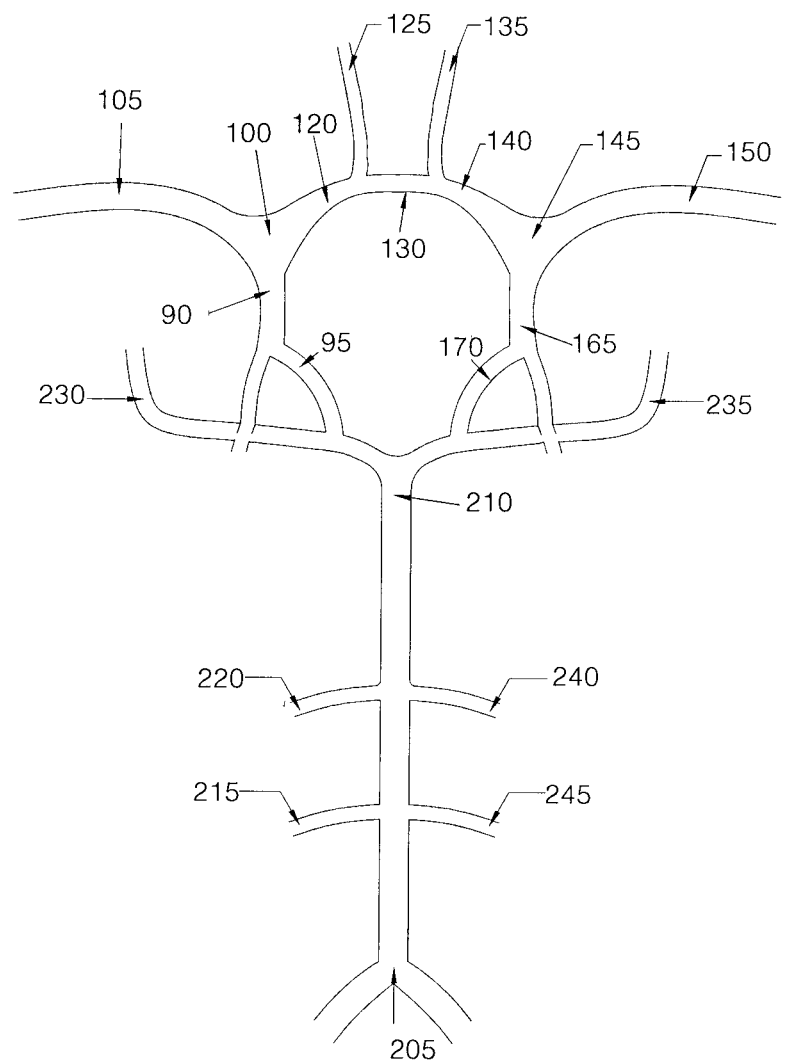
FIG. 4 is a schematic diagram illustrating the Circle of Willis and the main collateral blood vessel pathways in the brain.

FIG. 4 is a schematic diagram illustrating the main collateral pathways and communications between the cerebral arterial blood vessels including the internal carotid artery system (90 to 170) as well as the vertebro-basilar artery system (205 to 245), and this is known as the Circle of Willis. The supraclinoid portion of the right internal carotid artery 90 gives off the right posterior communicating artery 95 which anastomoses or communicates with the right posterior cerebral artery 230 and helps form the posterior part of the circle of Willis. The supraclinoid portion of the right internal carotid artery 90 then bifurcates 100 into the right middle cerebral artery 105 as well as the right anterior cerebral artery 120 at the right internal carotid artery bifurcation 100. The A1 segment of the right anterior cerebral artery 120 further continues as the A2 segment of the right anterior cerebral artery 125 and at the junction of the A1 and A2 segments gives off an important branch called the anterior communicating artery 130 that anastomoses or communicates with the junction of the A1 segment 140 and A2 segments 135 of the left anterior cerebral artery and helps form the anterior part of the circle of Willis. The supraclinoid portion of the left internal carotid artery 165 gives off the left posterior communicating artery 170, which anastomoses or communicates with the left posterior cerebral artery 235 and helps form the posterior part of the circle of Willis. The supraclinoid portion of the left internal carotid artery 165 then bifurcates 145 into the left middle cerebral artery 150 as well as the left anterior cerebral artery 140 at the left internal carotid artery bifurcation 145. The A1 segment of the left anterior cerebral artery 140 further continues as the A2 segment of the left anterior cerebral artery 135 and at the junction of the A1 and A2 segments gives off an important branch called the anterior communicating artery 130 that communicates with the junction of the A1 segment 120 and A2 segments 125 of the right anterior cerebral artery and helps form the anterior part of the circle of Willis. The anterior 130 and posterior communicating arteries 95 and 170 help with the anastomoses or communication of the internal carotid artery system (90 to 170) with the vertebro-basilar arterial system (205 to 245) and helps maintain an adequate collateral pathway for blood supply in the brain (see FIG. 2 for further details on the course of the internal carotid arteries and see FIG. 3 for further details on the course of the vertebral arteries). There are numerous anatomic variations to this and can play an important role at the time of a stroke.

Figure 5:
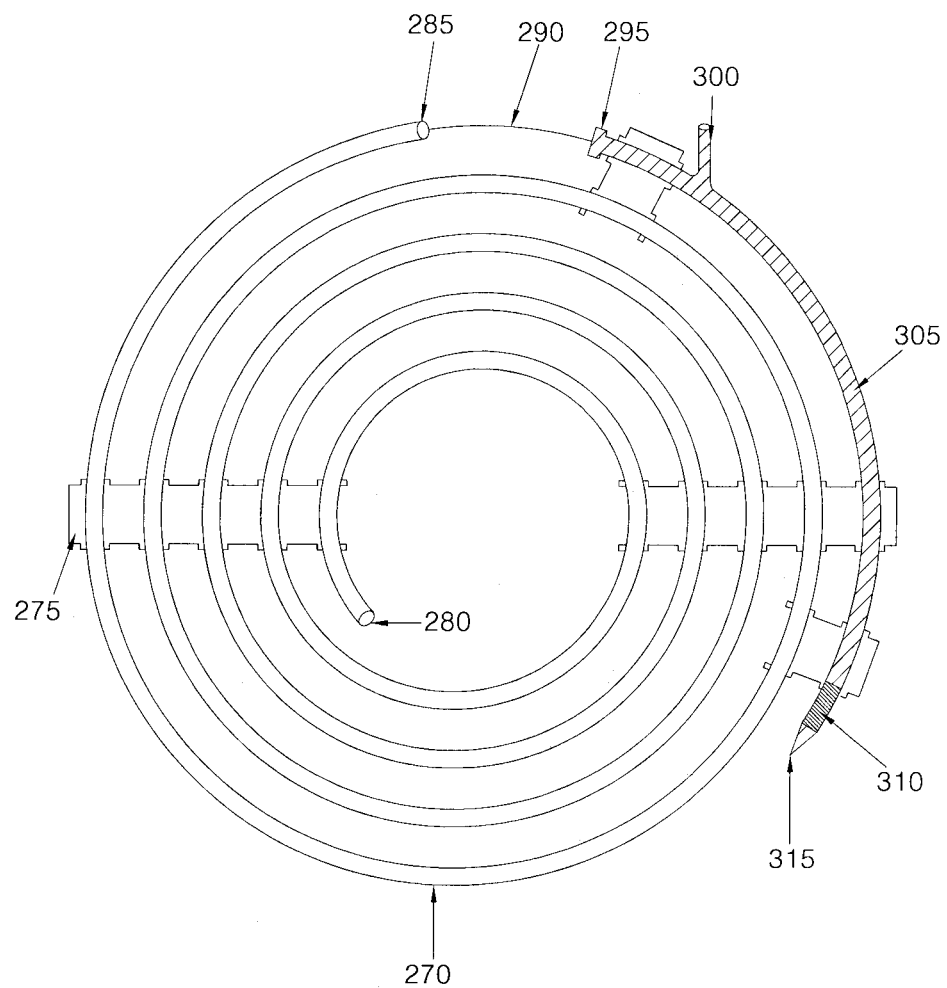
FIG. 5 illustrates the introducer system for delivery of the distal embolic protection device into the microcatheter.

FIG. 5 illustrates an introducer system to deliver the distal embolic protection device into the microcatheter. The microguidewire 290 that contains the distal embolic protection device is housed in a protective spiral polymer case 270 to avoid kinks or bends in the microguidewire. The spiral loops of the protective polymer case are kept together by clasps 275. The proximal end of the microguidewire is at the inner end of the spiral polymer case. The distal end of the microguidewire with the distal embolic protection device are kept in an introducer sheath 305 that is made out of a polymer (such as Teflon) and the portion of the introducer sheath 310 directly overlying the distal embolic protection device and protecting it is shown in this figure. The proximal end of the introducer sheath has a hemostatic valve 295 and a port for attaching a saline flush syringe 300 to be able to saline flush the introducer sheath as well as the distal embolic protection device of any air. The distal end of the introducer sheath 315 is the part that helps feed the distal embolic protection device into the microcatheter. When the distal protection device needs to be loaded into the microcatheter, the introducer sheath is removed from the clasps, of the spiral polymer case 275 and the microguidewire is slowly pulled off the distal port of the spiral polymer case 285.

Figure 6:
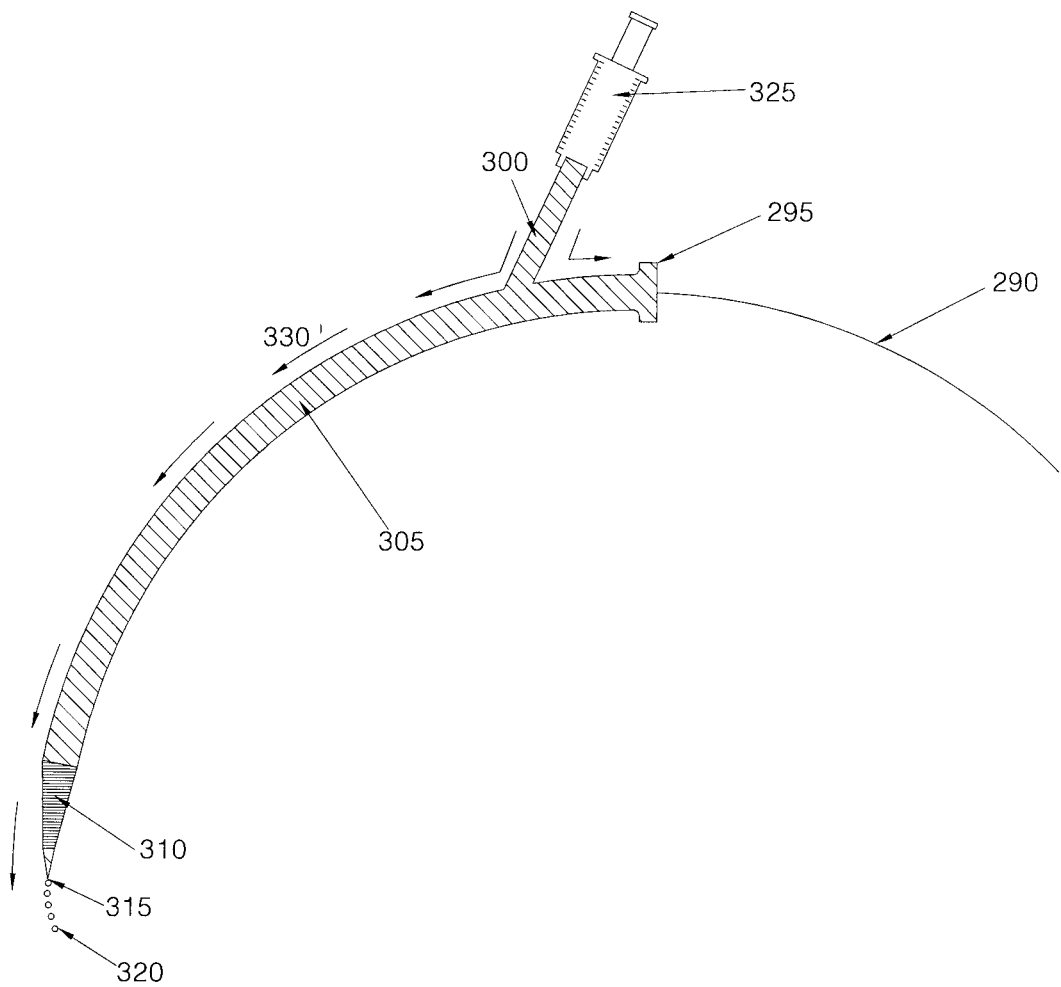
FIG. 6 illustrates the introducer sheath and its components.

FIG. 6 illustrates the introducer sheath 305 as well as the portion of the distal end of the introducer sheath 310 directly overlying the distal embolic protection device and protecting it. When the saline syringe 325 is connected to port 300 of the introducer sheath and is flushed, then the hemostatic valve is locked at the proximal end 295, and saline drops 320 will be noted to arise from the tip of the introducer sheath 315 because of saline moving in the direction 330 of the tip of the introducer sheath 315 suggesting that the introducer sheath 305 and the portion of the distal end of the introducer sheath 310 directly overlying the distal embolic protection device have been flushed of air.

Figure 7A:
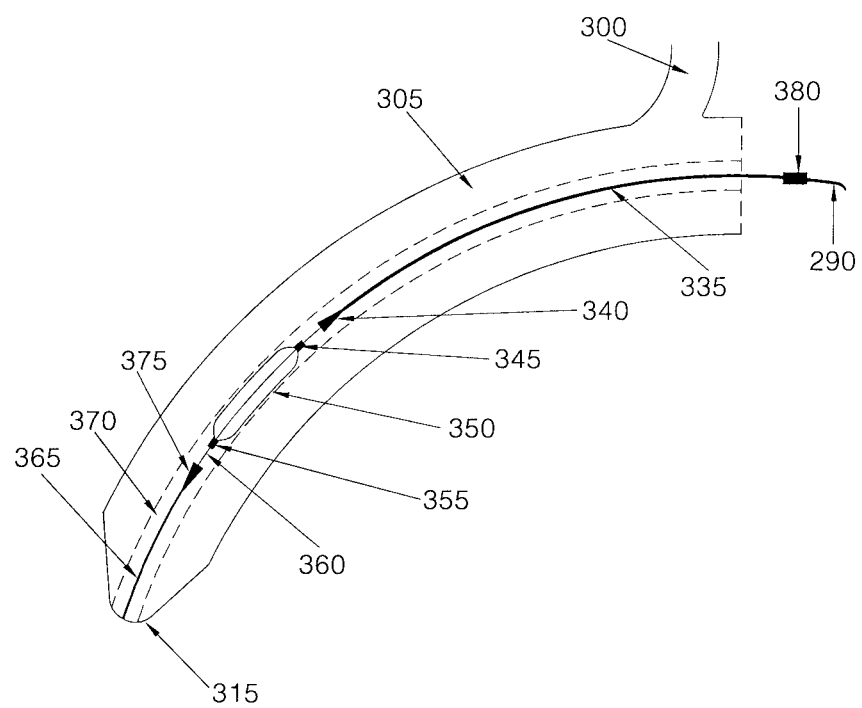
FIG. 7A illustrates a magnified cross sectional view of an introducer sheath with the distal embolic protection device comprising the filtering device and variable thickness microguidewire.
Figure 7B:
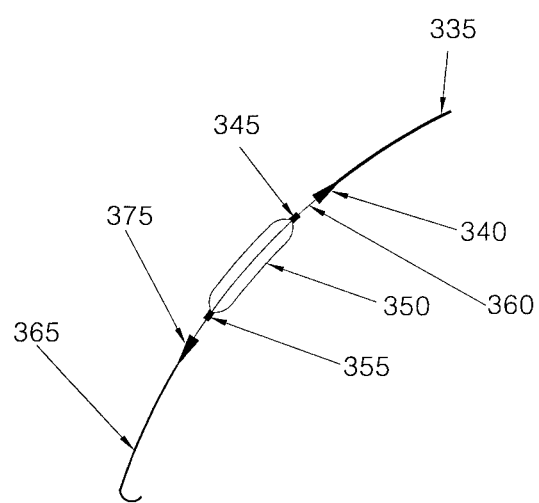
FIG. 7B illustrates a magnified view of the variable-thickness microguidewire with the filtering device mounted on it and shown in a collapsed configuration within the microcatheter.

FIG. 7A illustrates the distal embolic protection device comprising the filtering device in the collapsed configuration 350 that is back loaded into the introducer sheath 305 over the microguidewire. FIG. 7B illustrates a magnified view of the distal embolic protection device comprising the filtering device in a collapsed configuration mounted on the variable thickness micro-guidewire. The length of the microguidewire is sufficient for use in existing microcatheters during interventional neurovascular procedures and preferably ranges from 190 to 300 cm in length. The majority of the proximal 290 and distal 335 microguidewire are around 0.014 inch (0.356 mm) in thickness to be compatible with existing microcatheters, balloons and stents that are used in neurovascular interventions. Part of the distal segment of the microguidewire 335, e.g., 135 cm, is shown in the figure. The distal segment of the microguidewire has a thinner segment 360 that is about 0.010 inch (0.254 mm) or less in thickness and this is in the location where the filtering device is mounted. The filtering device is depicted in a collapsed configuration 350. The thinner segment 360 of the microguidewire where the filtering device is located is much thinner than the rest of the microguidewire 335 and is no more than about 0.010 inch (0.254 mm) and preferably measures about 0.008 to 0.010 inch (0.203 mm to 0.254 mm) in thickness. This is to maintain a small thin profile of the filtering device in the collapsed or non-expanded configuration within the inner lumen of the introducer sheath 370 so that the overall thickness of the distal embolic protection device, comprising the microguidewire and filtering device in the collapsed configuration are kept to a thickness less than or equal to 0.017 inch (0.432 mm) to be compatible with existing microcatheters, balloons, and stents. The thinner segment 360 of the microguidewire meets the thicker segment of the microguidewire at the proximal stop 340 and distal stop 375. The proximal 340 and distal stops 375 are no more than about 0.017 inch (0.432 mm) and preferably range from 0.014 inch to 0.017 of an inch (0.356 mm to 0.432 mm). The filtering device 350 has proximal 345 and distal 355 attachment points that allow the filtering device to be mobile over the microguidewire in the rotatory and longitudinal directions, relative to the microguidewire. The movement of the filtering device relative to the microguidewire is limited to within the thinner segment of the microguidewire 360 by the proximal 340 and distal stops 375. The microguidewire distal 365 to the distal stop 375 comprises several components that are further described in FIG. 9 and includes a shapeable tip 395, preferably curved, to enable torquability and to avoid wire perforation of a small vessel. The microguidewire may comprise a marker 380 at a predetermined location, e.g. at 135 cm from the distal tip of the microguidewire, to aid in determining when the distal embolic protection device is likely to emerge from the distal end of the microcatheter (normally 135 cm to 175 cm in length) and in determining the progress and location of the distal embolic protection device within the cerebral arterial blood vessel. Preferably the 135 cm marker is visually detectable by the operator so that fluoroscopy can be avoided till approximately 135 cm of the microguidewire has been advanced through the microcatheter.

Figure 8A:
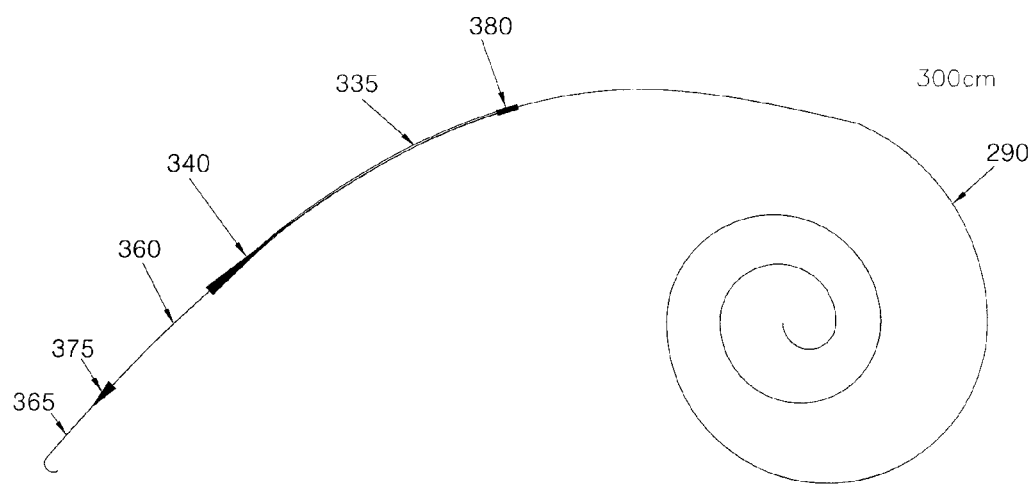
FIGS. 8A and 8B illustrate the microguidewires in two lengths 300 cm and 190 cm respectively.
Figure 8B:
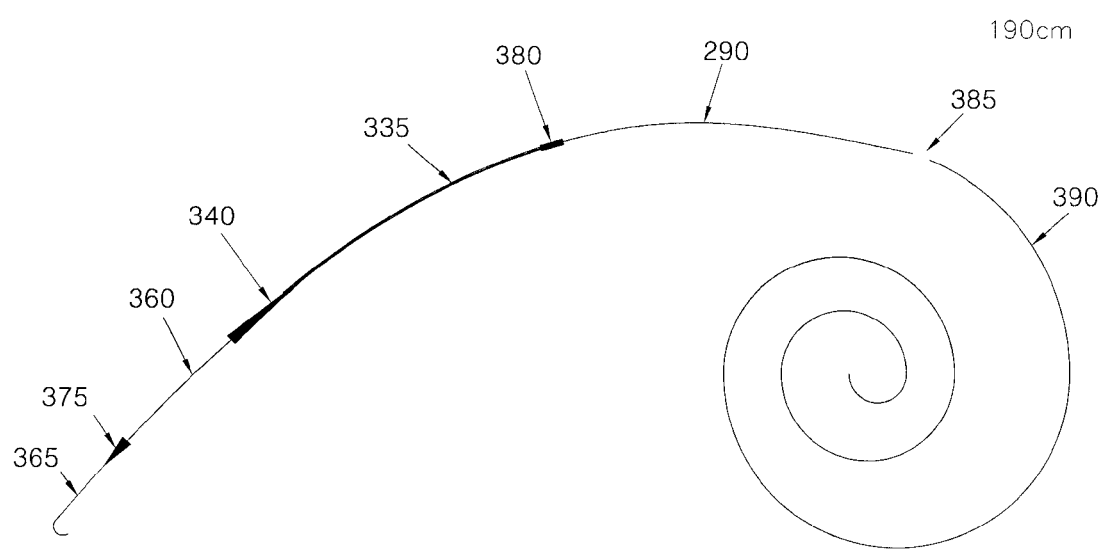

FIGS. 8A and 8B illustrate the components of the microguidewire at two lengths namely an exchange length 300 cm (FIG. 8A) and a non-exchange length microguidewire length 190 cm respectively (FIG. 8B). The microguidewire is of variable thickness at the distal end, having a thinner segment to accommodate a distal embolic protection device. The majority of the microguidewire 335, other than the thinner segment, is of thickness no more than about 0.014 inch (0.356 mm) and is compatible for use with existing microcatheters, balloons, and stents used in neurovascular interventions. A marking 380 on the microguidewire indicates the 135 cm length so that fluoroscopy can be avoided till approximately 135 cm of the microguidewire has been advanced through the microcatheter. The distal segment of the microguidewire, where the filtering device is present, comprises a thinner segment 360 having a thickness that is no more than about 0.010 inch (0.254 mm) to accommodate the non-expanded filtering device and still maintain an overall low thickness profile of the distal embolic protection device. The microguidewire has a proximal 340 and distal 375 stop that will allow the filtering device to be stationary in a small cerebral arterial blood vessel despite rotatory and longitudinal motion of the microguidewire over a small distance. The proximal and distal stops have a thickness of no more than about 0.017 inch (0.432 mm) and preferably from 0.014 to 0.017 inch (0.356-0.432 mm). Part of the distal segment of the microguidewire 335 e.g. distal 30 cm comprises several components that are further described in detail in FIGS. 9A to 9D. The distal end includes a distal tip 365 which may comprise radio-opaque shapeable material to provide some trackability and to retain a curved shape to avoid small vessel perforation. FIG. 8A shows an exchange length microguidewire 300 cm in length. FIG. 8B shows a non-exchange length microguidewire 190 cm in length. The non-exchange length guidewire has a capability at its proximal end 385 to have an extension microguidewire 390 attached if it needs to be converted into an exchange length microguidewire.

Figure 9A:
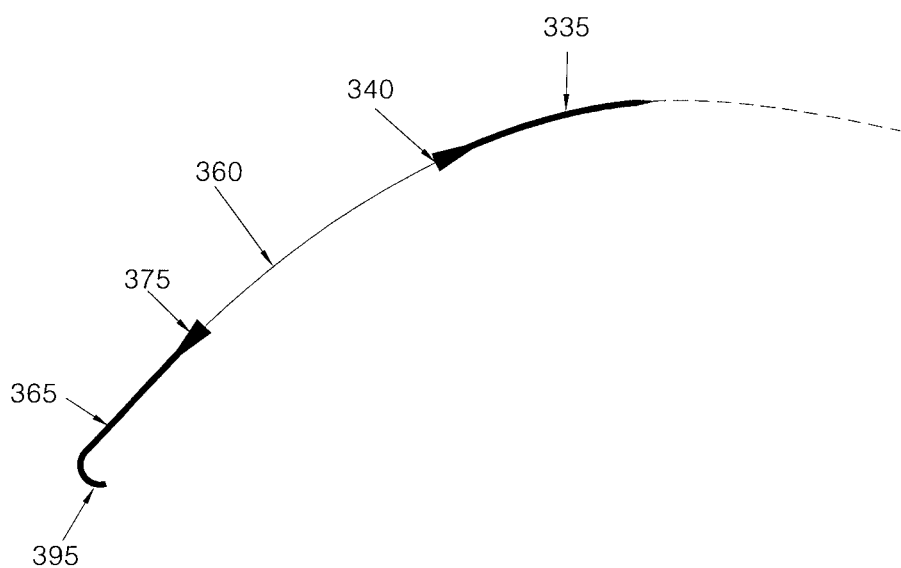
FIG. 9A is an illustration of the distal segment of the microguidewire (distal 30 cm).
Figure 9B:
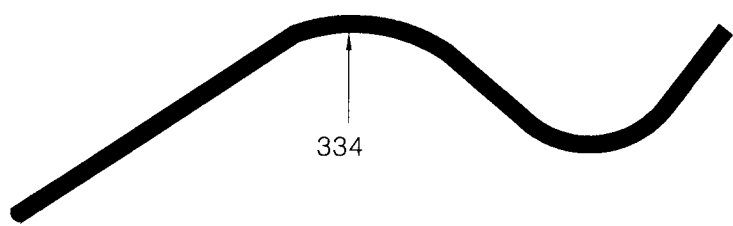
FIGS. 9B, 9C and 9D are magnified views of embodiments of the variable thickness microguidewire with different components of the distal segment of the microguidewire illustrated (distal 30 cm).
Figure 9C:
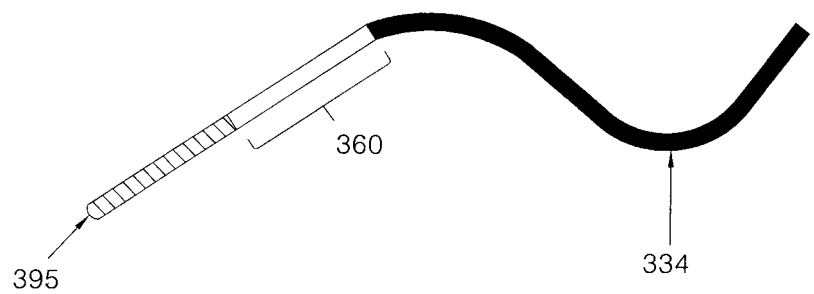
Figure 9D:
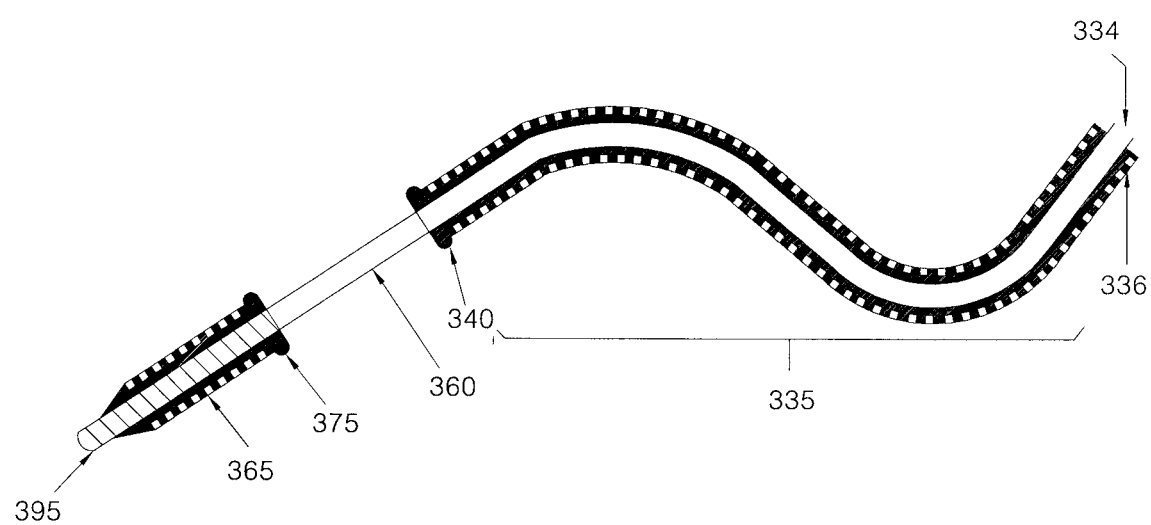

FIG. 9A is an illustration of an embodiment of the distal segment of the microguidewire e.g. distal 30 cm described in FIG. 8. FIGS. 9B, 9C and 9D are magnified views of the various components of the distal segment of the variable thickness microguidewire e.g. distal 30 cm. The microguidewire is of variable thickness at the distal segment to accommodate a filtering device at its distal end. The majority of the microguidewire 335 is no more than about 0.014 inch (0.356 mm) in thickness, and is compatible with existing microcatheters, balloons, and stents used in neurovascular interventions. The microguidewire 335 comprises various components including a core microguidewire 334 that runs the entire length of the microguidewire and provides support and trackability that is need for catheterization of the small cerebral arterial blood vessels. The core microguidewire comprises of a metal e.g. stainless steel or an alloy e.g. nickel-titanium. The core microguidewire 334 is no more than about 0.014 inch (0.356 mm) in majority of its length in the proximal segment and is tapered to no more than about 0.010 inch (0.254 mm) in the distal segment of the microguidewire e.g distal 30 cm. The distal segment of the microguidewire e.g. distal 30 cm comprises a core microguidewire 334 depicted in FIG. 9B-D that is no more than about 0.010 inch (0.254 mm) in thickness forming the thinner segment of the microguidewire 360 of FIG. 9C-D, and comprises thicker segments proximal to the proximal stop 340 as well as distal to the distal stop 375, where the core may be coated or covered by another layer or layers, e.g., a coil made up of a radio-opaque material or metal or alloy such as platinum as shown in FIG. 9C forming the shapeable tip of the microguidewire 395, or a flexible hypotube 336 of FIG. 9D covering the core microguidewire 334 or a combination of both as shown in FIG. 9D. The coating, or covering, may provide more support as well as trackability that is need for catheterization of the small cerebral arterial blood vessels. The coated core microguidewire is no more than about 0.014 inch (0.356 mm) in thickness in the majority of its length. The various components of this distal segment of the microguidewire are illustrated in more detail in FIGS. 9B to 9D. The thinner segment of the microguidewire 360 is no more than about 0.010 inch (0.254 mm) to accommodate the filtering device in its non-expanded state and still maintain an overall low thickness profile of the distal embolic protection device. In this thinner segment of the microguidewire where the filtering device is mounted 360, the components of the microguidewire are predominantly just the core microguidewire 334 as previously described. The distal end of the microguidewire 365 comprises several components that include a core microguidewire 334 as previously described, and a shapeable tip comprising a radio opaque material, metal or alloy, e.g., platinum, that is shapeable to provide some trackability and to retain a curved shape to avoid small vessel perforation. In addition the shapeable tip of the distal end of the microguidewire 365 may also include a coating or covering layer, such as a flexible hypotube 336, covering the core microguidewire 334 to give it more support and strength and is no more than about 0.014 inch (0.356 mm) in the majority of its length. The microguidewire has proximal 340 and distal 375 stops that allow the filtering device to be stationary in a small cerebral blood vessel despite rotatory and longitudinal motion of the microguidewire relative to the filtering device between the proximal and distal stops. The thickness of the stops is no more than about 0.017 inch (0.432 mm) and preferably from 0.014 to 0.017 inch (0.356-0.432 mm).

Various components of the variable thickness microguidewire may be made up of materials that are biocompatible or surface treated to produce biocompatibility. Suitable materials include e.g., stainless steel, platinum, titanium and its alloys including nickel-titanium, etc. Suitable materials also include a combination of metals and alloys such that the core of the microguidewire 334 forming the thinner segment 360 could be made from metals or alloys such as stainless steel or nickel-titanium etc. In order to provide a shapeable tip that has some trackability, and that has the capacity to retain a curved shape to avoid small vessel perforation, as well as be visible during neurovascular interventional procedures, the distal end of the core microguidewire 334 is preferably covered by a coating of a radio-opaque material or metal or alloy, e.g., platinum. To provide more support to the core microguidewire to be able to advance the microguidewire along with the filtering device through a microcatheter, the core microguidewire 334 may have a coating or covering layer, e.g., a flexible hypotube, and made of metals or alloys, e.g., nickel, titanium, platinum, tungsten etc. In the areas where the microguidewire needs to be visible namely the parts of the distal segment of the microguidewire 335 e.g. distal 30 cm and the distal tip of the microguidewire 365 including the two stops 340 and 375, the coating or covering layer over the core microguidewire, or the flexible hypotube, or the core microguidewire itself, comprise or are coated with radio-opaque materials, metals or alloys, including but not limited to platinum, tantalum, gold, palladium, tungsten, tin, silver, titanium, nickel, zirconium, rhenium, bismuth, molybdenum, or combinations of the above etc to enable visibility during neurovascular interventional procedures.

Figure 10:
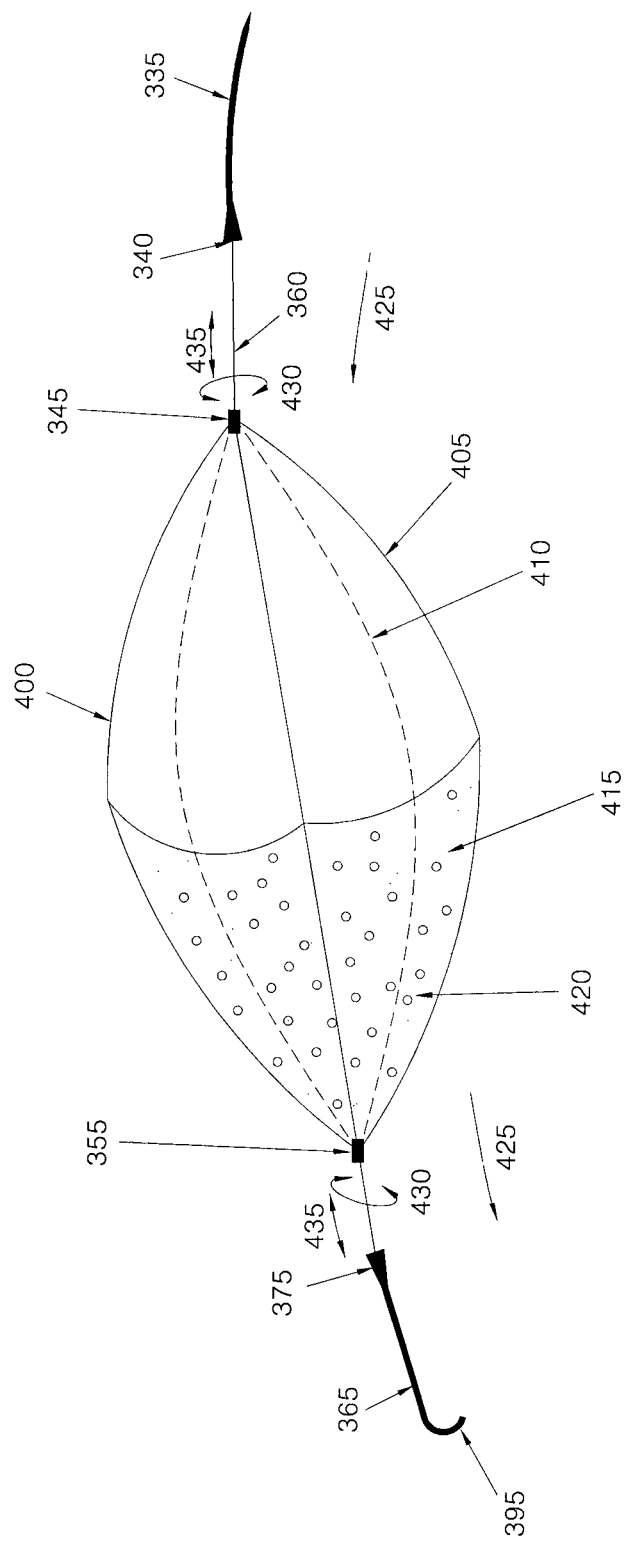
FIG. 10 is an illustration of one of the embodiments of the distal embolic protection device.

FIG. 10 is an illustration of one of the embodiments of the distal embolic protection device comprising the filtering device and the microguidewire. The filtering device has a proximal 345 and distal 355 attachment points that are also the sliding or mobile components of the filtering device. These mobile attachment points have a capacity to allow the microguidewire to rotate 430 as well as move back and forth in the longitudinal direction 435 between the two stops in the microguidewire (340, 375) while keeping the filtering device stationary in a small cerebral blood vessel and thereby decrease friction and trauma on the cerebral blood vessel walls.

The filtering device of the distal embolic protection device of this invention may comprise a filter membrane and an expansion assembly capable of assuming an expanded configuration and a collapsed configuration. Preferably the expansion assembly comprises a plurality of struts (400, 405, 410) that connect the proximal attachment point 345 to the distal attachment point 355. The filter membrane may be attached to the struts and the distal attachment point, and in the expanded configuration the filter membrane has a hemispherical shape covering the struts.

The struts comprise a biocompatible material or materials that are surface treated for biocompatibility. The materials are preferably self-expanding. Suitable materials include but are not limited to stainless steel, titanium and its alloys, cobalt-chromium alloy, carbon fiber and its composites, and various biomedical polymers, e.g., polyurethane, polyethylene, polyester, polypropylene, poly tetra fluoro-ethylene, polyamides, polycarbonate or polyethylene-terephthalate. A shape memory or super-elastic material such as nickel-titanium alloy is also suitable. The number of struts will depend on the size of expansion needed for the diameter of the cerebral blood vessel. The distal embolic protection device will be suitable for use in cerebral blood vessels from vessel diameters of 1.5 mm to 4.5 mm.

In addition to the two stops in the microguidewire 340 and 375, as well as the two mobile attachment points in the filtering device 345 and 355, various portions of the distal embolic protection device including parts of the struts 400 to 410, or parts of the filter membrane 415 may be radio-opaque. Radio-opaque materials are understood as materials that are visible on a fluoroscopy screen during neurovascular interventional procedures. This allows the operator to determine the location of the device during neurovascular interventions. Radio-opaque materials include, e.g., metals or alloys including but are not limited to platinum, tantalum, gold, palladium, tungsten, tin, silver, titanium, nickel, zirconium, rhenium, bismuth, molybdenum, or combinations of the above etc. The struts may comprise metals or alloys that are radio-opaque, e.g., platinum or the others listed above. Alternatively the struts may comprise shape-elastic alloys such as nickel-titanium, which are not significantly radio-opaque but small portions of radio-opaque metals or alloys, e.g., tantalum, can be attached to non-radio-opaque struts by suturing the filter membrane to the struts with tantalum wires or other suitable radio-opaque material.

The filtering device also comprises a filter membrane 415 for collecting emboli or debris that might be released during the neurovascular intervention. The filter membrane may comprise a biomedical polymer, e.g., polyurethane (BioSpan™ made by Polymer Technology Group and Chronoflex™ made by CardioTech International), polyethylene (Rexell™ made by Huntsman), polypropylene (Inspire™ made by Dow), polyester (Hytril™ made by Dupont), poly tetra fluoro-ethylene (Teflon™ made by Dupont), polyamides (Durethan™ made by Bayer), polycarbonate (Corethane™ made by Corvita Corp), or polyethylene-terephthalate (Dacron™ made by Dupont). The filter membrane may further comprise a radio-opaque material, e.g., particles of tantalum, particles of gold, other radio-opaque agents, e.g., barium sulfate, tungsten powder, bismuth subcarbonate, bismuth oxychloride, iodine containing agents such as iohexol (Omnipaque™ made by Amersham Health). The filter membrane comprises pores 420 that are of the dimensions small enough to trap emboli or debris but large enough to allow the free passage of blood and its components such as blood cells preferably the pores are of 50 microns to 150 microns. The arrows 425 indicate the direction of blood flow within the blood vessel.

The microguidewire is thinner between the two radio-opaque stops 340 and 375 and in this thin segment 360, the microguidewire thickness is no more than about 0.010 inch (0.254 mm). This is to allow for the thickness of the filtering device comprising the struts such that in its non-expanded state the distal embolic protection device overall is no more than about 0.017 inch (0.432 mm). This is to enable the distal embolic protection device to be delivered through standard microcatheters that are commercially available (such as Echelon™ microcatheter, ev3 Inc; Excelsior™ microcatheter, Boston Scientific Corp; Prowler™ microcatheter, Cordis Neurovascular etc) that have an internal diameter of around 0.017 inch (0.432 mm).

Figure 11:
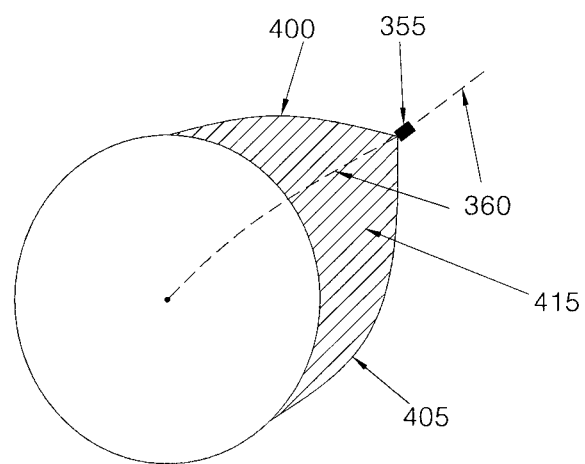
FIG. 11 is a schematic diagram illustrating the cross-sectional view of the distal embolic protection device described in FIG. 10.

FIG. 11 is a schematic diagram illustrating the cross-sectional view of the distal embolic protection device described in FIG. 10. Some of the struts 400 and 405 are shown in an expanded configuration, wherein the filter membrane 415 is depicted with a hemispherical shape covering the struts. The microguidewire 360 passing through the center of the filtering device as well as the distal attachment point 355 of the filtering device are also shown.

Figure 12:
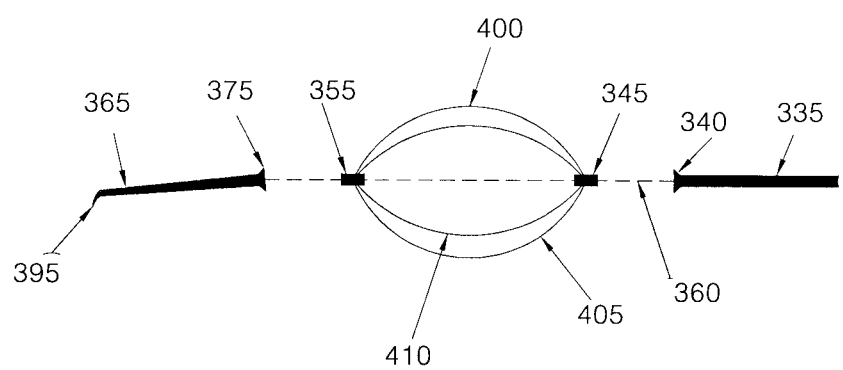
FIG. 12 illustrates one of the embodiments of a distal embolic protection device in the expanded configuration showing the radio-opaque components under fluoroscopy.

FIG. 12 is an illustration showing the distal embolic protection device described in FIG. 10 in an expanded configuration showing the radio-opaque components under fluoroscopy. The distal segment of the microguidewire 335 e.g. distal 30 cm is radio-opaque along with the proximal stop 340 and are made of radio-opaque metals or alloys, e.g., platinum, as mentioned in description of FIGS. 8A, 8B and 10. The microguidewire in the thinner segment 360 is not radio-opaque and is made up of a metal or alloy, e.g., nickel-titanium or stainless steel. The distal stop 375 as well as the distal end of the microguidewire 365 including the shapeable tip 395 are also made of a radio-opaque metal or alloy such as platinum as described in detail in FIGS. 8A, 8B, and 10. Portions of the struts 400 to 410 of the distal embolic protection device described in FIG. 10 are also made of a radio-opaque metal or alloy, e.g., platinum, or have a covering with a radio-opaque material, e.g., tantalum as described in FIG. 10 in detail. This enables the operator performing the neurovascular interventional procedure to clearly visualize the deployed distal embolic protection device as well as the position of the microguidewire.

Figure 13:
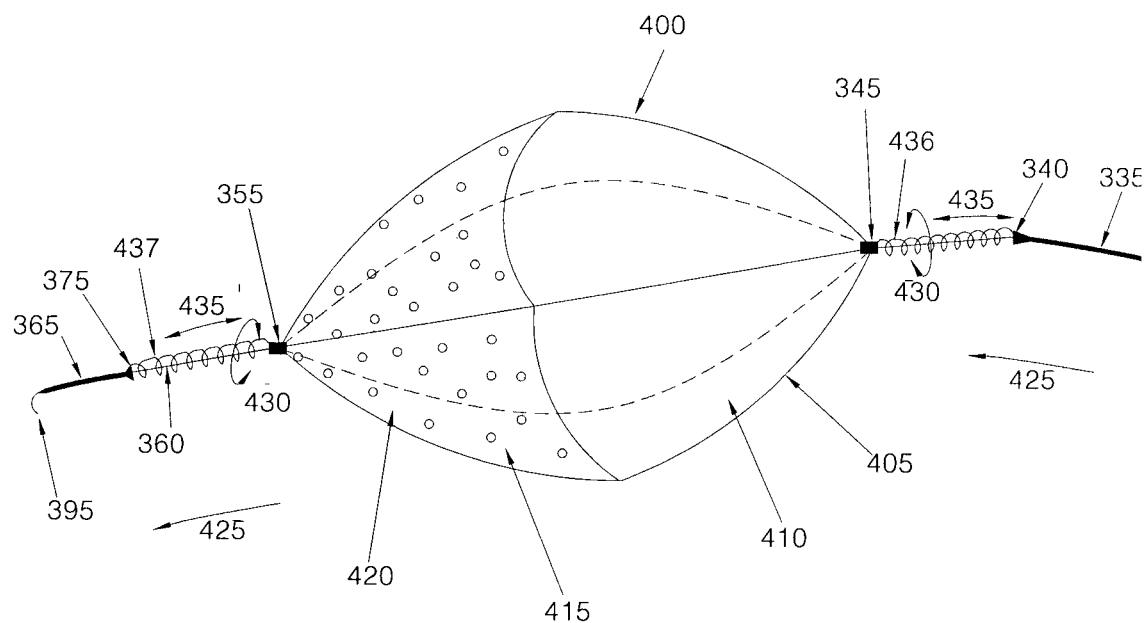
FIG. 13 illustrates another embodiment of a distal embolic protection device over the variable thickness microguidewire.

FIG. 13 is an illustration of another embodiment of a distal embolic protection device of this invention comprising a filtering device rotatably mounted on a variable-thickness microguidewire. The filtering device has proximal 345 and distal 355 attachment regions that are also the sliding or mobile components of the distal embolic protection device. These mobile attachment points have a capacity to allow the microguidewire to rotate 430 as well as move back and forth in the longitudinal direction 435 between the two stops in the microguidewire (340, 375) while keeping the distal embolic protection device stationary in a small cerebral blood vessel and thereby help decrease friction and trauma on the cerebral blood vessel walls. The distal embolic protection device in this embodiment comprises an expansion assembly comprising a plurality of struts (400, 405, 410) that connect the proximal attachment point 345 to the distal attachment point 355 and are capable of assuming an expanded configuration and a collapsed configuration The expanded configuration of the plurality of struts and the filter membrane having a hemspherical shape is depicted. The distal embolic protection device further comprises two cylindrical coils 436 and 437. Cylindrical coil 436 connects the proximal stop 340 to the proximal attachment point 345 of the filtering device. Cylindrical coil 437 connects the distal attachment point 355 of the filtering device to the distal stop 375 of the microguidewire. The cylindrical coils allow for rotatory 430 as well as longitudinal movement 435 of the filtering device relative to the microguidewire in the thinner segment of the microguidewire 360. The cylindrical coils decrease the shear stress on the thinner segment of the microguidewire 360 when the distal embolic protection device is recovered with a microcatheter, balloon catheter or stent catheter. The coils provide added support to the thinner segment of the microguidewire 360 and reduce fracture or stretching of the microguidewire at the region of the proximal stop 340 or distal stop 375. The cylindrical coils may be made of a biocompatible material, or a material that is surface treated to be biocompatible and may comprise radio-opaque metals or alloys, e.g., platinum, as described in detail in FIG. 10.

Figure 14A:
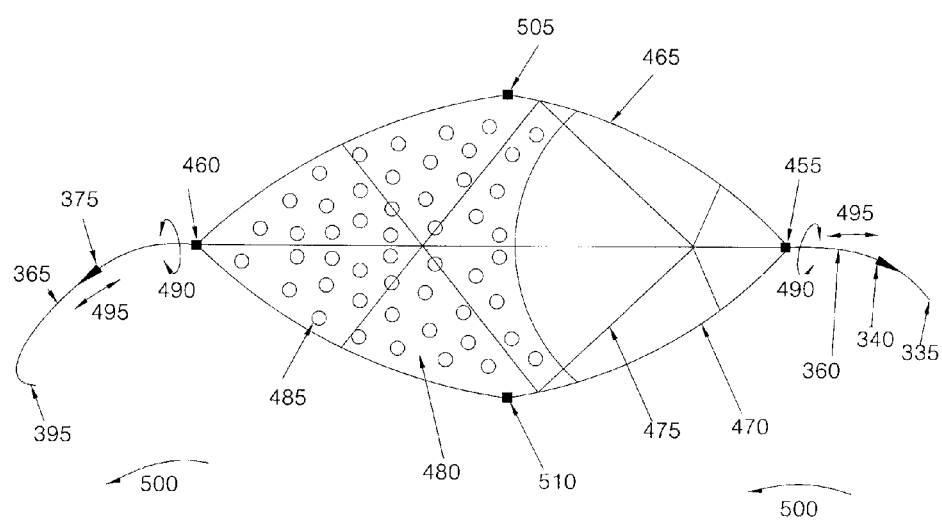
FIG. 14A is an illustration of another embodiment of the distal embolic protection device.

FIG. 14A is an illustration of another of the embodiments of the filtering device attached to the microguidewire. The filtering device comprises proximal 455 and distal 460 attachment points that are also the sliding or mobile components of the distal embolic protection device. These mobile attachment points have a capacity to allow the microguidewire to rotate 490 as well as move longitudinal direction 495 between the two proximal and distal stops of the microguidewire (340, 375) while the filtering device remains stationary in the small cerebral blood vessel and thereby help to decrease friction and trauma on the cerebral blood vessel walls. The distal embolic protection device in this embodiment comprises a filter membrane attached to the distal end of the filtering device and an expansion assembly comprising a plurality of struts 465, 470, 475 that connect the proximal attachment point 455 of the filtering device to the distal attachment point of the filtering device 460. The plurality of struts in the expanded configuration and the filter membrane having a helical or conical shape and covering the struts is also depicted.

The struts, preferably made of a biocompatible material or a material that is surface treated to be biocompatible and preferably made of a self-expanding material, are detailed in the embodiment described in FIG. 10. Suitable materials include but are not limited to stainless steel, titanium and its alloys, cobalt-chromium alloy, carbon fiber and its composites, and various polymers. A shape memory or super-elastic material such as nickel-titanium alloy is also suitable. The number of struts will depend on the size of expansion needed for the diameter of the cerebral blood vessel. The distal embolic protection device will be suitable for use in cerebral blood vessels from vessel diameters 1.5 mm to 4.5 mm.

In addition to the two stops in the microguidewire 340 and 375, as well as the two mobile attachment points in the filtering device 455 and 460, various portions of the distal embolic protection devices of this invention including parts of the struts 505 and 510, or parts of the filter membrane 480 may be radio-opaque. Radio-opaque materials are understood to be materials that are visible on a fluoroscopy screen during neurovascular interventional procedures. This allows the operator to determine the location of the device during neurovascular interventions. Radio-opaque materials include metals or alloys including but are not limited to platinum, tantalum, gold, palladium, tungsten, tin, silver, titanium, nickel, zirconium, rhenium, bismuth, molybdenum, or combinations of the above. The struts can be made of metals or alloys that are radio-opaque, e.g., platinum or the others listed above. Alternatively the struts are made of shape-elastic alloys such as nickel-titanium, which are not significantly radio-opaque, and may further comprise small portions of radio-opaque metals or alloys such as tantalum, that can be attached to the non-radio-opaque struts by suturing the filter membrane to the struts with a radio-opaque material, e.g. tantalum wires etc.

The filtering device comprises a filter membrane 480 to capture emboli or debris that might be released during the neurovascular intervention. The filter membrane is preferably a biomedical polymer, e.g., polyurethane (BioSpan™ made by Polymer Technology Group and Chronoflex™ made by CardioTech International), polyethylene (Rexell™ made by Huntsman), polypropylene (Inspire™ made by Dow), polyester (Hytril™ made by Dupont), poly tetra fluoro-ethylene (Teflon™ made by Dupont), polyamides (Durethan™ made by Bayer), polycarbonate (Corethane™ made by Corvita Corp), or polyethylene-terephthalate (Dacron™ made by Dupont). The filter membrane may further comprise a radio-opaque material, e.g., particles of tantalum, particles of gold, other radio-opaque agents such as barium sulfate, tungsten powder, bismuth subcarbonate, bismuth oxychloride, iodine containing agents such as Omnipaque™. The filter has pores 485 that are small enough to trap emboli or debris but large enough to allow the free passage of blood and its components such as blood cells, preferably the pores are 50 microns to 150 microns in diameter. The arrows 500 indicate the direction of blood flow within the cerebral blood vessel.

The microguidewire is thinner between the two radio-opaque stops 340 and 375 and in this thinner segment 360, the microguidewire thickness is no more than about 0.010 inch (0.254 mm). This is to accommodate the filtering device such that in its non-expanded configuration the thickness of the filtering device is less than or equal to 0.017 inch (0.432 mm). This is to enable the distal embolic protection device to be delivered through standard microcatheters that are commercially available (such as Echelon™ microcatheter, ev3 Inc; Excelsior™ microcatheter, Boston Scientific Corp; Prowler™ microcatheter, Cordis Neurovascular etc) that have an internal diameter of about 0.017 inch (0.432 mm).

Figure 14B:
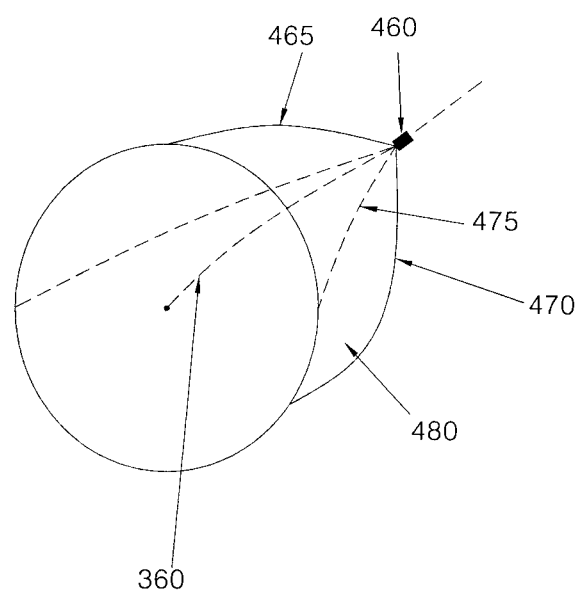
FIG. 14B is a schematic diagram illustrating the cross-sectional view of the distal embolic protection device described in FIG. 14A.

FIG. 14B is a schematic diagram illustrating the cross-sectional view of the distal embolic protection device described in FIG. 14A. The struts 465 to 475 are depicted in an expanded configuration, providing the filtering device with a helical or conical shape. The filter membrane 480 is depicted as covering the struts 465, 470, 475. The microguidewire 360 passing through the center of the filtering device as well as the distal attachment point 460 of the filtering device are shown.

Figure 15A:
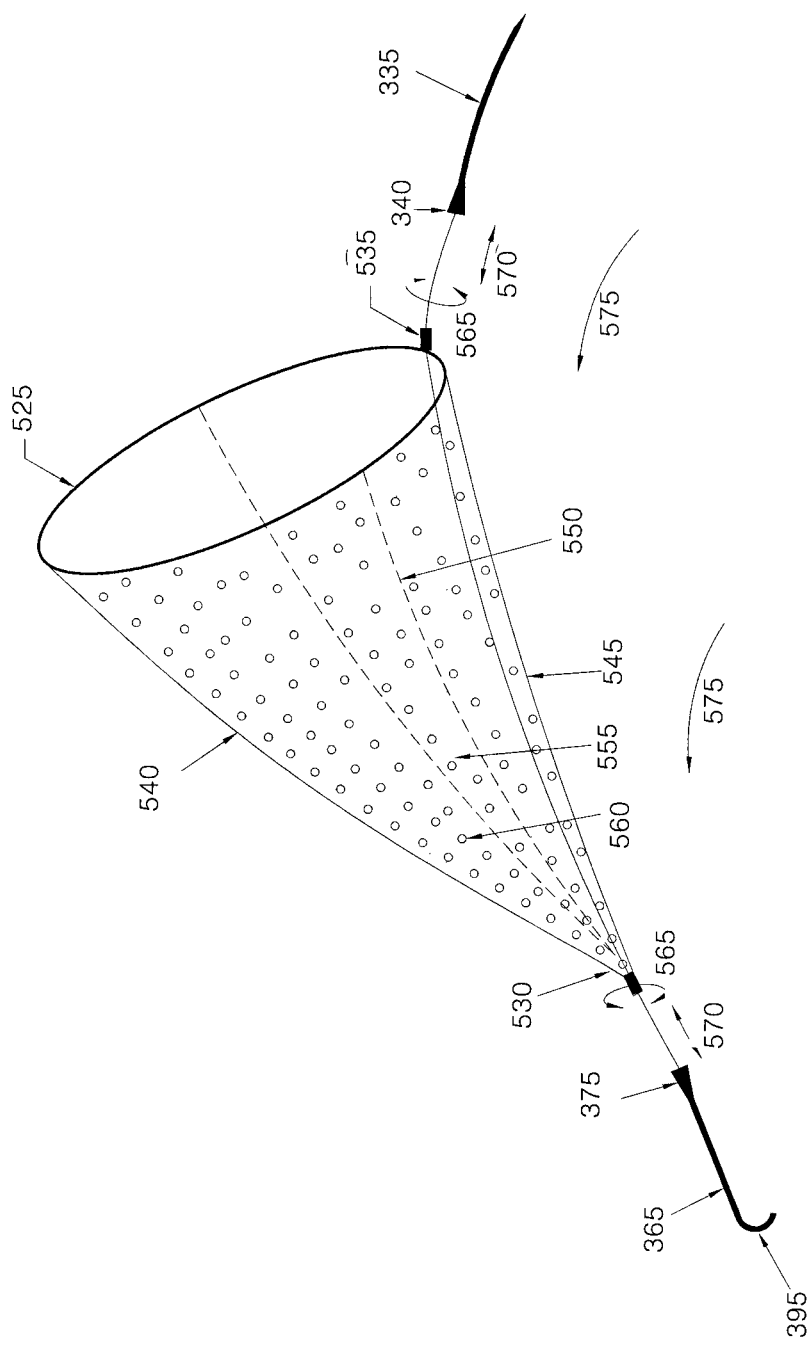
FIG. 15A is an illustration of another embodiment of the distal embolic protection device.

FIG. 15A is an illustration of another embodiment of the distal embolic protection device. The filtering device has proximal 535 and distal 530 attachment points that are also the sliding or mobile components of the filtering device. These mobile attachment points have a capacity to allow the microguidewire to rotate 565 as well as move back and forth in the longitudinal direction 570 relative to the filtering device between the two stops in the microguidewire (340, 375) while keeping the filtering device stationary in a small cerebral blood vessel and thereby decrease friction and trauma on the cerebral blood vessel walls. The filtering device in this embodiment comprises a filter membrane 555 and a ring 525. The filter membrane is attached to the ring and the ring is connected to the proximal attachment point 535. The ring in turn comprises a plurality of struts 540, 545, 550 that connect the ring 525 to the distal attachment point 530. The ring and if present the plurality of struts when expanded can provide the filtering device with a conical shape.

The ring, and if present the plurality of struts, are made of biocompatible materials or materials that are surface treated such that they are biocompatible. The materials are preferably self-expanding as described in FIG. 10. Suitable materials include but are not limited to stainless steel, titanium and its alloys, cobalt-chromium alloy, carbon fiber and its composites, and various polymers. A shape memory or super-elastic material such as nickel-titanium alloy is also suitable. The number of struts will depend on the size of expansion needed for the diameter of the cerebral blood vessel to be treated. The distal embolic protection devices of this invention are suitable for use in cerebral blood vessels from vessel diameters 1.5 mm to 4.5 mm.

In addition to the two stops in the microguidewire 340 and 375, as well as the two mobile attachment points in the device 535 and 530, various portions of the distal embolic protection device including the ring 525, or parts of the filter membrane 555 may further comprise a radio-opaque material. Radio-opaque materials are understood as materials that are visible on a fluoroscopy screen during neurovascular interventional procedures. This allows the operator to determine the location of the device during neurovascular interventions. Radio-opaque materials can include metals or alloys, including but not limited to platinum, tantalum, gold, palladium, tungsten, tin, silver, titanium, nickel, zirconium, rhenium, bismuth, molybdenum, or combinations of the above etc. The struts can be made up of metals or alloys that are radio-opaque such as platinum or the others listed above. Alternatively the struts may be made of shape-elastic alloys such as nickel-titanium, which are not significantly radio-opaque, but may be made radio-opaque by attaching small portions of radio-opaque metals or alloys, e.g., tantalum, to the non-radio-opaque struts by suturing the filter membrane to the struts with a radio-opaque material, e.g., tantalum wires etc.

The filtering device comprises a filter membrane 555 that extends from the ring 525 to the distal attachment point 530 and acts as a filter for emboli or debris that might be released during the neurovascular intervention. The filter membrane may cover the struts. Materials for this filter include but are not limited to biomedical polymers such as, e.g., polyurethane (BioSpan™ made by Polymer Technology Group and Chronoflex™ made by CardioTech International, polyethylene (Rexell™ made by Huntsman), polypropylene (Inspire™ made by Dow), polyester (Hytril™ made by Dupont), poly tetra fluoro-ethylene (Teflon™ made by Dupont), polyamides (Durethan™ made by Bayer), polycarbonate (Corethane™ made by Corvita Corp), or polyethylene-terephthalate (Dacron™ made by Dupont). The filter has pores 560 that are small enough to trap emboli or debris but large enough to allow the free passage of blood and its components such as blood cells. Preferably the pores are 50 microns to 150 microns. The arrows 575 indicate the direction of blood flow with the cerebral blood vessel. The filter membrane may further comprise radio-opaque materials, e.g., as particles of tantalum, particles of gold, other radio-opaque agents, e.g., barium sulfate, tungsten powder, bismuth subcarbonate, bismuth oxychloride, iodine containing agents such as Omnipaque™.

The microguidewire is thinner between the two radio-opaque stops 340 and 375 and in this thinner segment 360, the microguidewire thickness is no more than about 0.010 inch (0.254 mm). This is to allow for the thickness of the distal embolic protection device, the ring and the struts if present such that in the non-expanded state the ring of the distal embolic protection device is no more than about 0.017 inch (0.432 mm). This is to enable the distal embolic protection device to be delivered through standard microcatheters that are commercially available (such as Echelon™ microcatheter, ev3 Inc; Excelsior™ microcatheter, Boston Scientific Corp; Prowler™ microcatheter, Cordis Neurovascular etc) that have an internal diameter of about 0.017 inch (0.432 mm).

Figure 15B:
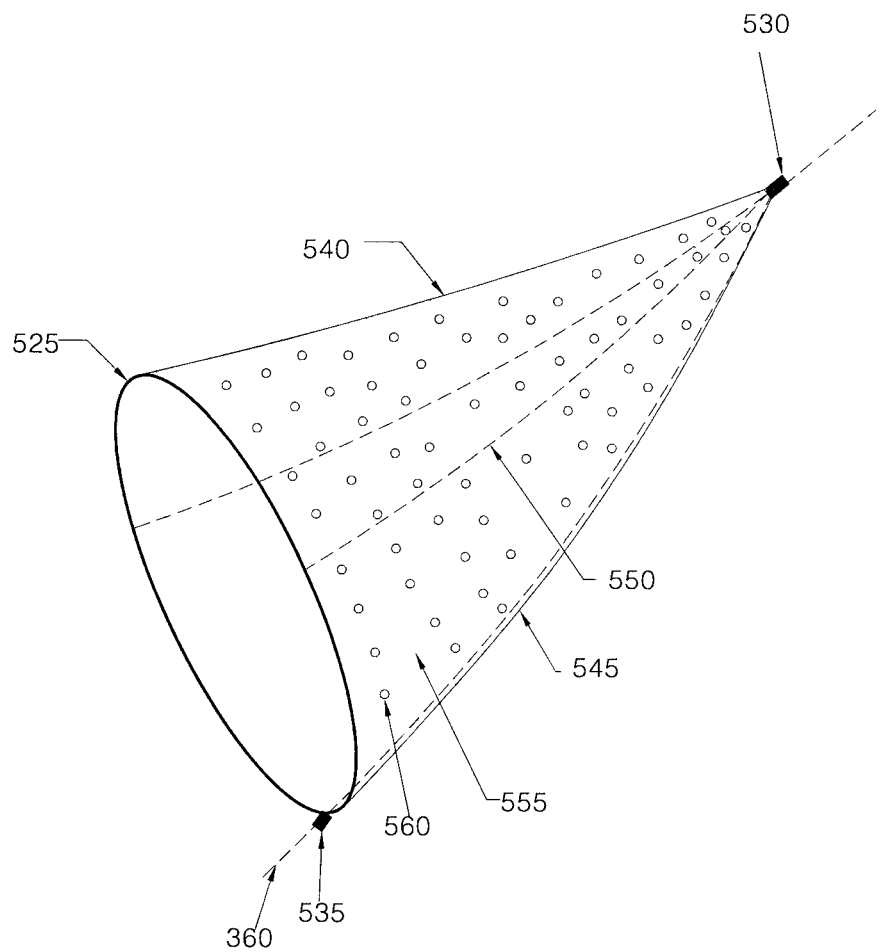
FIG. 15B is a schematic diagram illustrating the cross-sectional view of the distal embolic protection device described in FIG. 15A.

FIG. 15B is a schematic diagram illustrating the cross-sectional view of the distal embolic protection device described in FIG. 15A. The radio-opaque ring is shown 525 and is attached to a filter membrane 555 connecting the ring to the distal attachment point 530. The filter membrane has micro-pores 560. In one of the embodiments of this device, there is also a plurality of struts 540 to 550 connecting the ring 525 to the distal attachment point. The microguidewire 360 passing through the side of the filtering device as well as the proximal 535 and distal attachment points 530 of the filtering device are shown.

Figure 16:
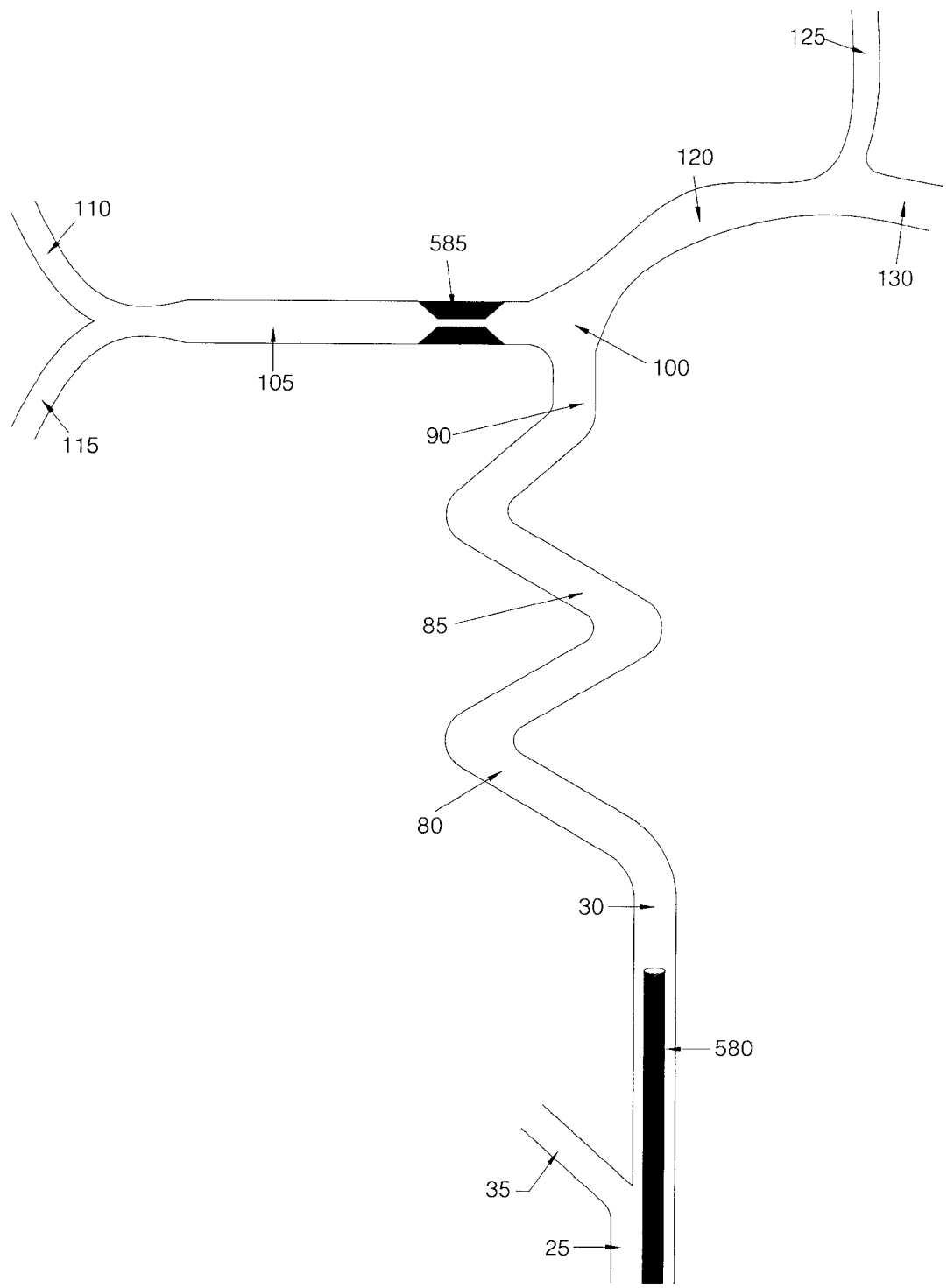
FIG. 16 is a schematic diagram illustrating a significant blockage or stenosis 585 in the right middle cerebral artery 105.

FIG. 16 is a schematic diagram illustrating a significant blockage or stenosis 585 in the right middle cerebral artery 105 that is causing mini-strokes and is refractory to medical therapy. A guide catheter (6 French or larger) 580 has been advanced into the right internal carotid artery 30 so that intracranial balloon angioplasty and stenting can be performed.

Figure 17:
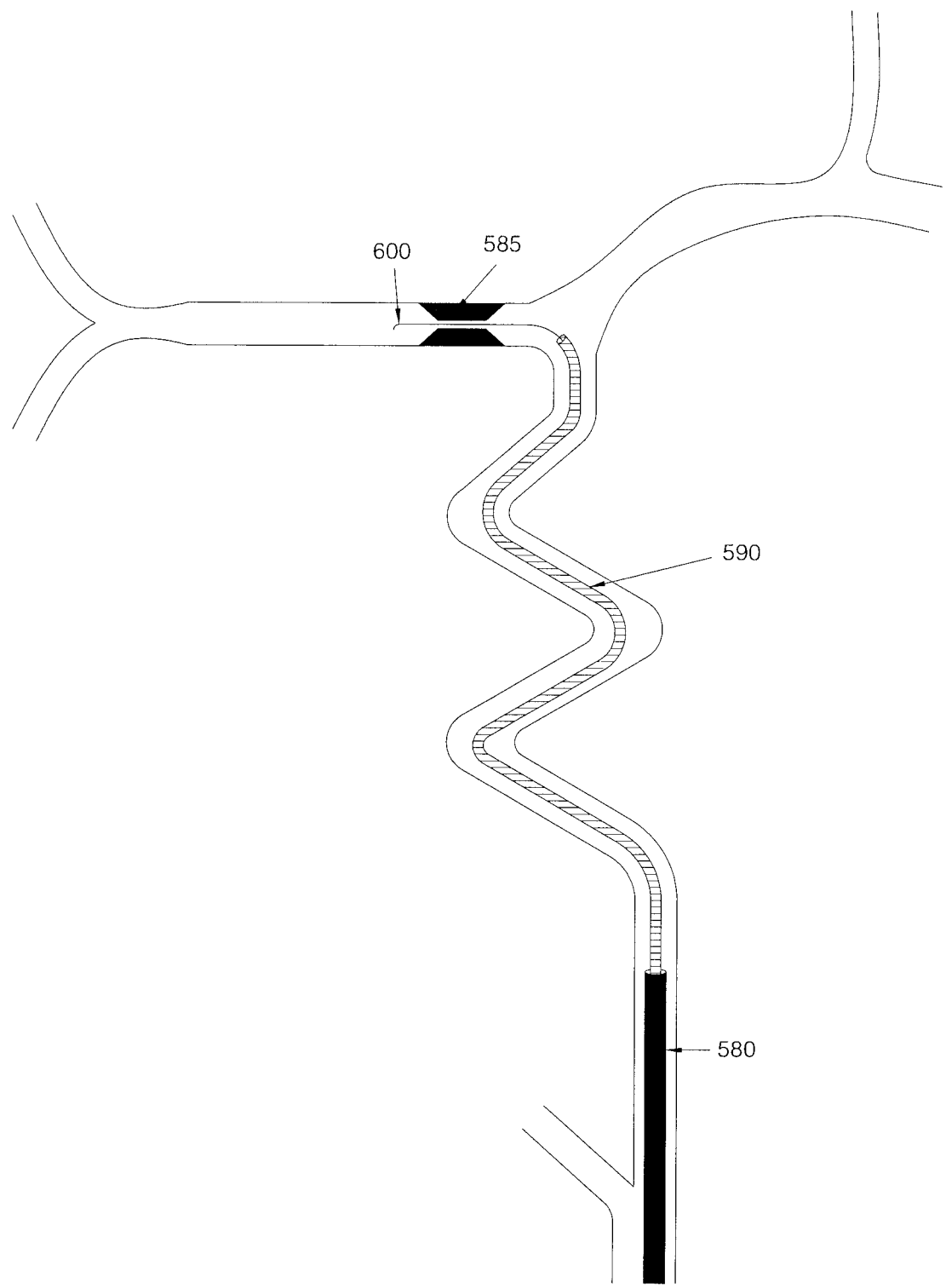
FIG. 17 is a schematic diagram illustrating a microcatheter being advanced into the right middle cerebral artery over a microwire.

FIG. 17 is a schematic diagram illustrating that through the guide catheter in the right internal carotid artery, a microcatheter 590 is being advanced in the right internal carotid artery into the right middle cerebral artery over a microwire 600. The microwire is carefully advanced across the blockage in the right middle cerebral artery 585. The microcatheter is then advanced over the microwire.

Figure 18:
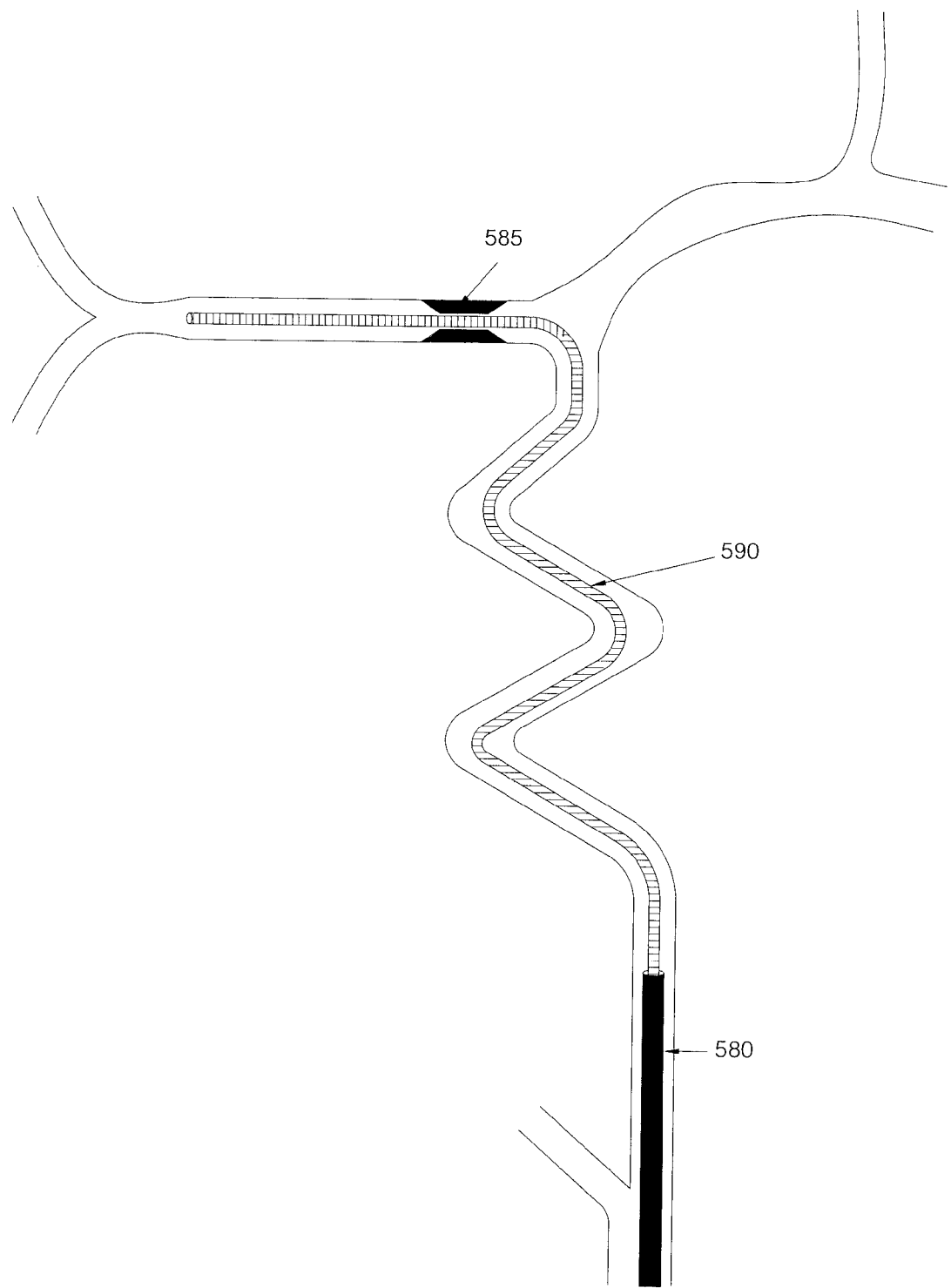
FIG. 18 is a schematic diagram illustrating the microcatheter has been carefully advanced across the blockage in the right middle cerebral artery over a microwire.

FIG. 18 is a schematic diagram illustrating that the microcatheter 590 has been carefully advanced across the blockage in the right middle cerebral artery 585 over a microwire. The microwire has been removed once the microcatheter is distal to the blockage 585 in the right middle cerebral artery. Prior to exchanging the microcatheter for a balloon catheter, a distal embolic protection device is decided to be advanced to the right middle cerebral artery through the microcatheter.

Figure 19:
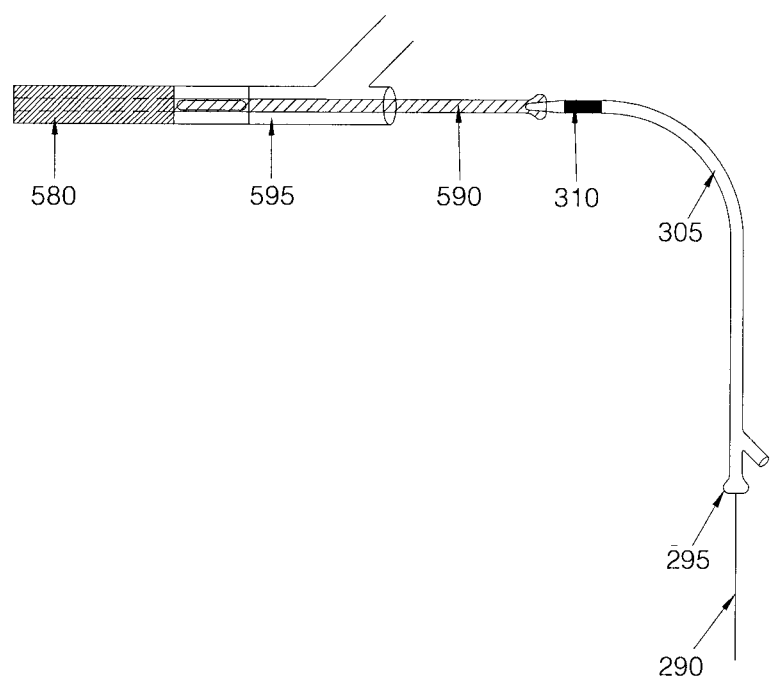
FIG. 19 is a schematic diagram illustrating the introducer sheath with the non-expanded distal embolic protection device and microguidewire are being advanced through the microcatheter.

FIG. 19 is a schematic diagram illustrating the introducer sheath 305 with the non-expanded distal embolic protection device 310 comprising microguidewire 290 are being advanced through the microcatheter 590. The hemostatic valve 295 at the proximal end of the introducer sheath is released so that the microguidewire 290 can be advanced. Once the distal embolic protection device 310 has entered the microcatheter 590 and guide catheter 580, the introducer sheath 305 can be removed. The guide catheter 580 is connected to a rotating hemostatic valve 595 to prevent backbleeding. The microcatheter 590 passes through the rotating hemostatic valve 595 and then into the guide catheter 580.

Figure 20:
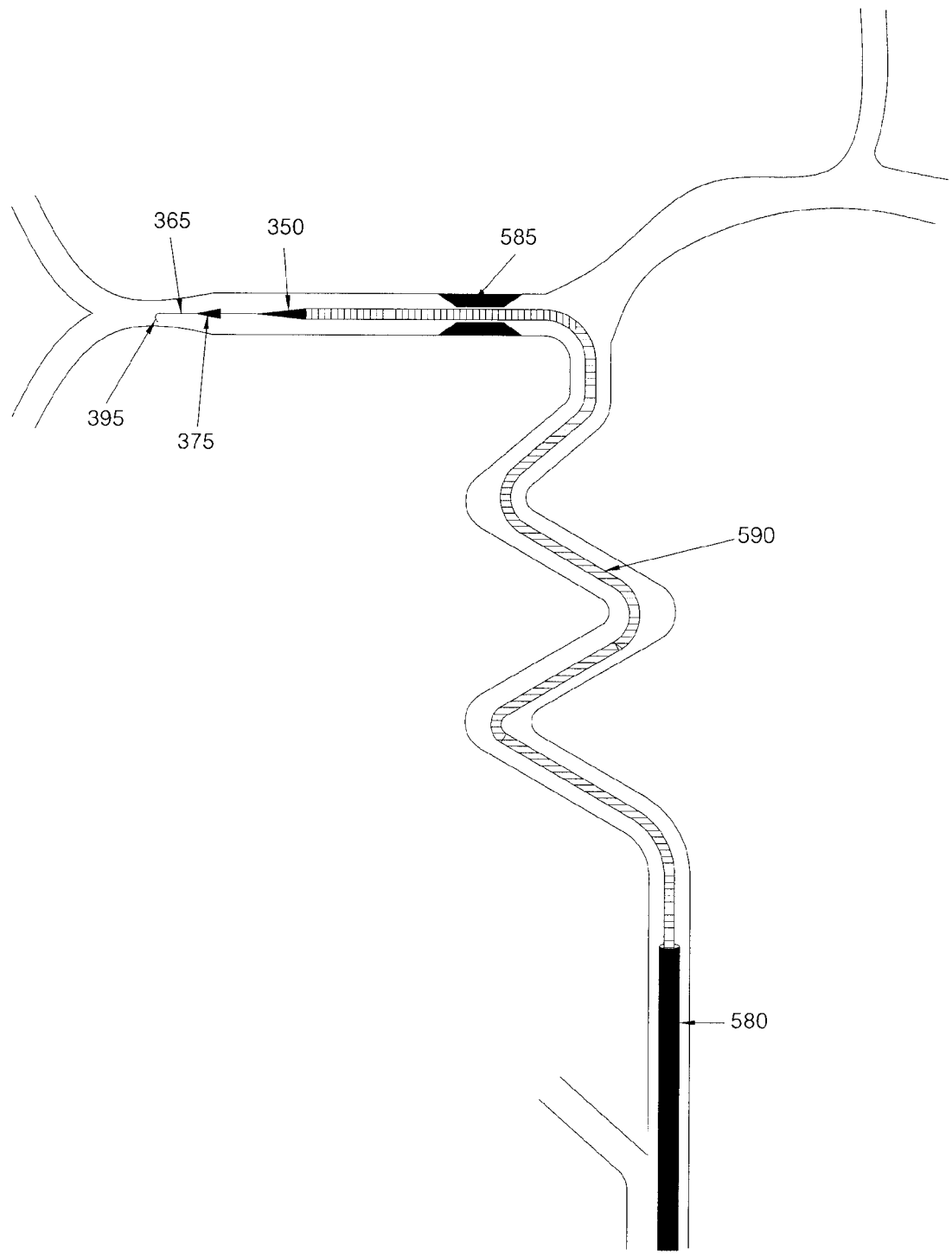
FIG. 20 is a schematic diagram illustrating the distal embolic protection device in the appropriate location distal to the blockage and the microcatheter being withdrawn to deploy the device.

FIG. 20 is a schematic diagram illustrating the distal embolic protection device 350 in the non-expanded state in the appropriate location distal to the blockage 585 in the right middle cerebral artery. With the microguidewire 365 in position and fixed, the microcatheter 590 is being withdrawn to deploy the filtering device. The tip of the microguidewire 395 is shaped to avoid perforating a small vessel. The distal stop 375 in the microguidewire acts as the radio-opaque marker.

Figure 21:
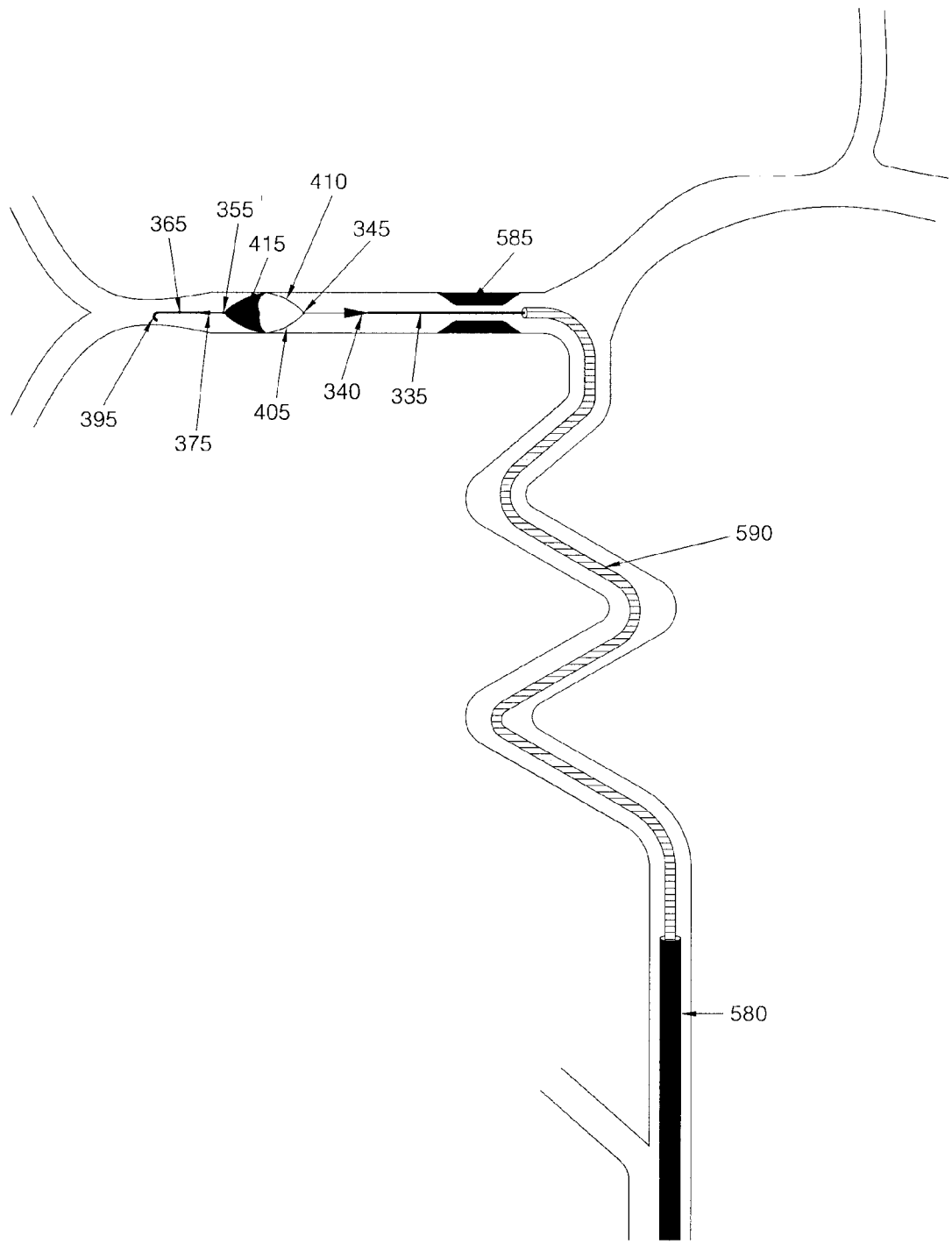
FIG. 21 is a schematic diagram illustrating the distal embolic protection device fully deployed.

FIG. 21 is a schematic diagram illustrating the distal embolic protection device fully deployed in the right middle cerebral artery distal to the blockage 585. The radio-opaque distal part of the microguidewire 365 along with the shapeable tip 395 are noted. The radio-opaque stops of the microguidewire 340 and 375 are noted. The filtering device with the plurality of struts 405 and 410 between the two attachment points 345 and 355 are noted. The filter membrane 415 is noted. With the microguidewire fixed in position, the microcatheter 590 is being exchanged for a balloon catheter so that intracranial balloon angioplasty can be performed.

Figure 22:
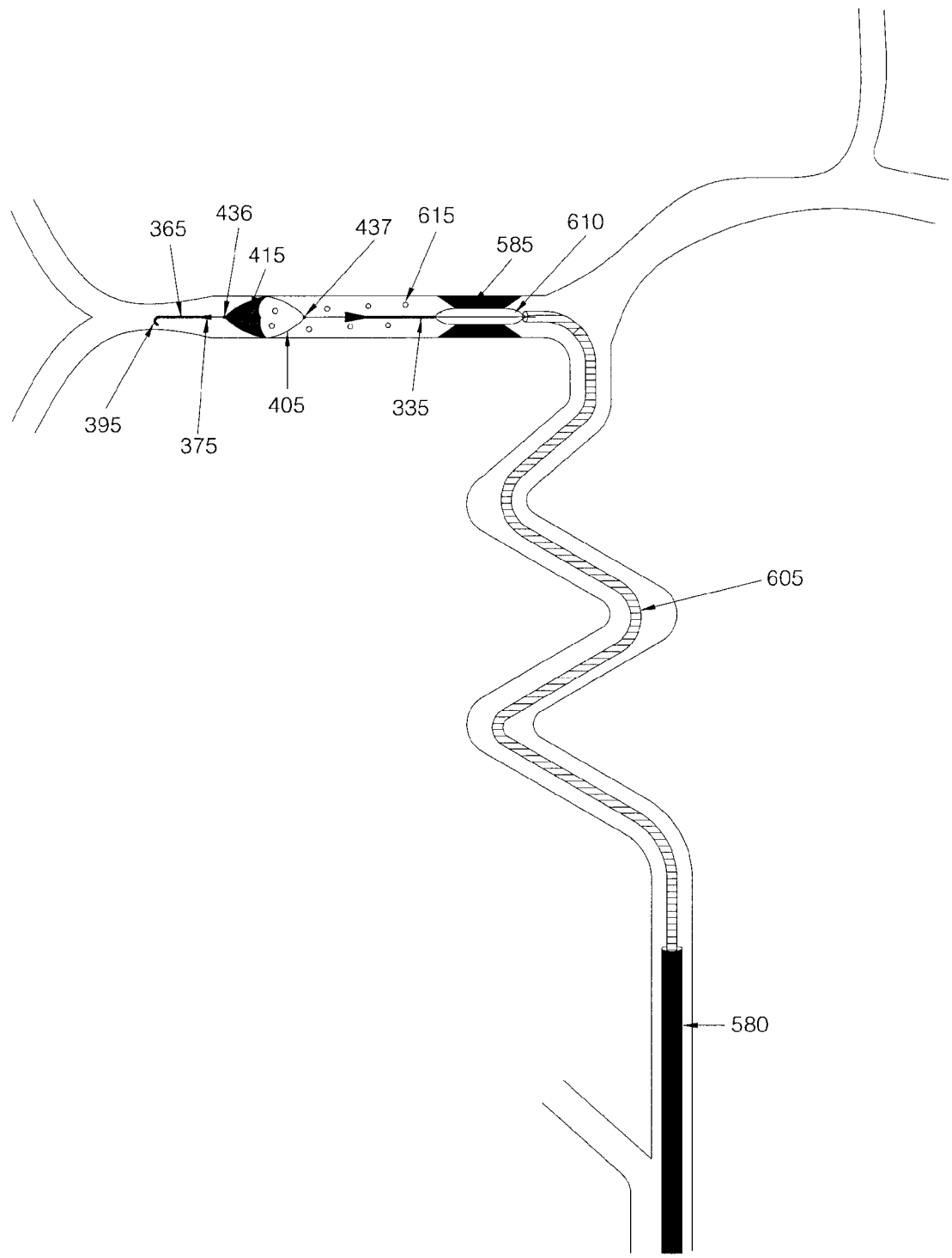
FIG. 22 is a schematic diagram illustrating intracranial angioplasty being performed using the distal embolic protection device.

FIG. 22 is a schematic diagram illustrating the filtering device is in place distal to the blockage 585 in the right middle cerebral artery. With the microguidewire in position, the microcatheter is exchanged for a balloon catheter 605. The mobile attachment points 345 and 355 of the filtering device allow for the filtering device to be stationary even if there is minimal movement of the microguidewire 335 during the microcatheter exchange. When the balloon 610 is across the blockage 585 in the right middle cerebral artery, intracranial balloon angioplasty is performed. During intracranial balloon angioplasty, emboli or debris are released 615 and are collected in the distal embolic protection device by the filter 415.

Figure 23:
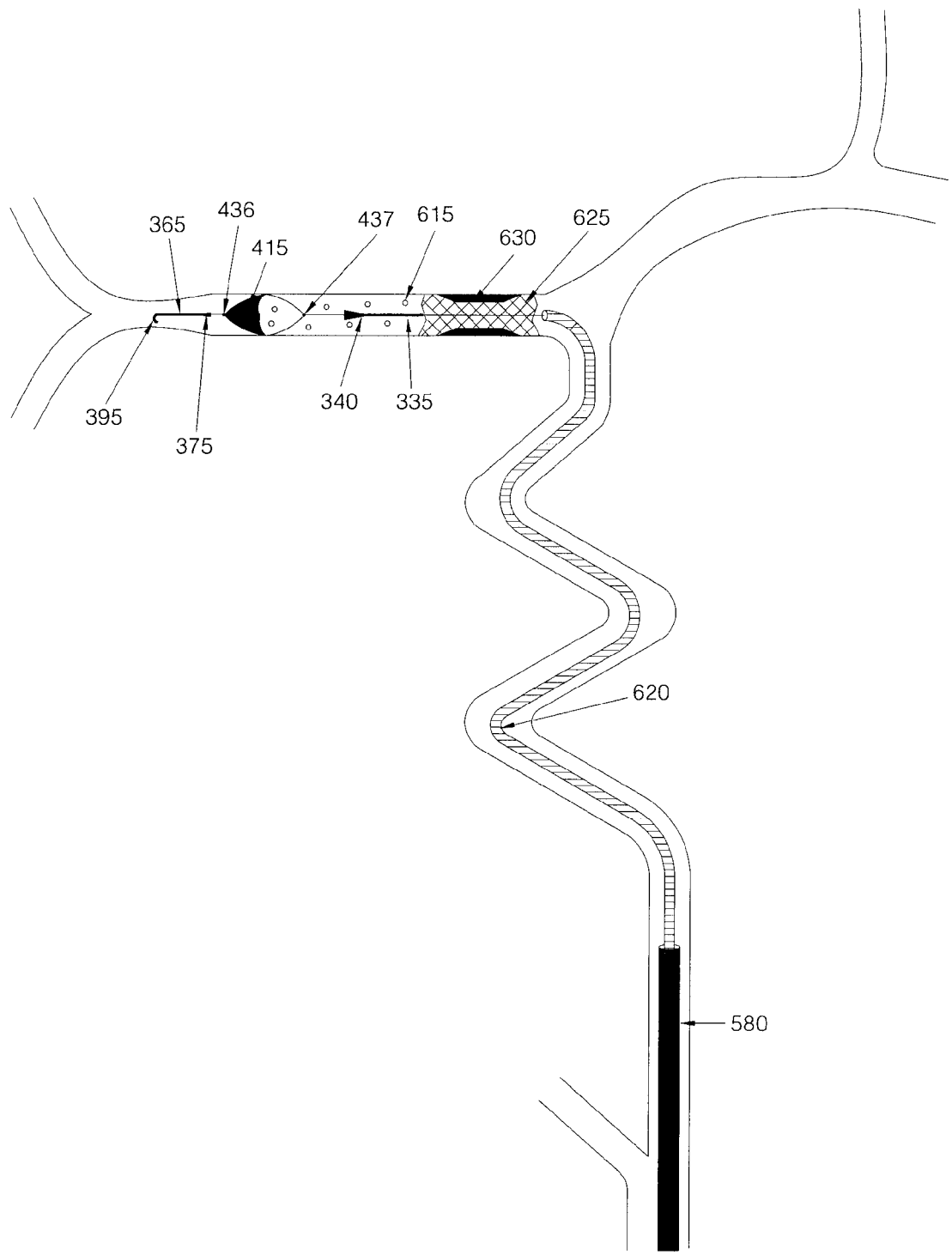
FIG. 23 is a schematic diagram illustrating intracranial stenting being performed using the distal embolic protection device.

FIG. 23 is a schematic diagram illustrating that after intracranial angioplasty, the balloon 610 shown in FIG. 22 is deflated and the balloon catheter 605 is exchanged for an intracranial stent catheter 620 over the microguidewire. When the stent is in position across the area of blockage 630 in the right middle cerebral artery where balloon angioplasty was performed, the stent is deployed. During intracranial stenting, small emboli or debris are released 615 and are collected in the filter 415 of the distal embolic protection device. After stenting is performed, the distal embolic protection device can be retrieved using the stent catheter 620 by advancing it over the microguidewire till the radio-opaque markers in struts of the distal embolic protection device suggest that the filter has closed so that the device can be safely removed.

Figure 24:
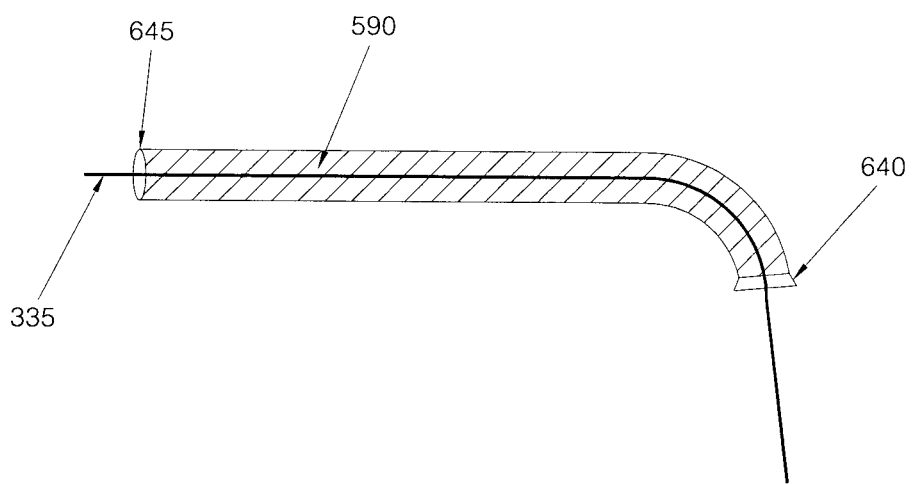
FIG. 24 is a schematic diagram of a standard microcatheter used to recover the distal embolic protection device.

FIG. 24 is a schematic diagram illustrating a standard microcatheter, which can be alternatively used to retrieve the distal embolic protection device. In this case, the stent catheter 620 shown in FIG. 23 is exchanged for a standard catheter 590 over the microguidewire 335. The standard microcatheter has a proximal 640 and distal end 645. Standard microcatheters that are commercially available (such as Echelon™ microcatheter, ev3 Inc; Excelsior™ microcatheter, Boston Scientific Corp; Prowler™ microcatheter, Cordis Neurovascular etc) can be used and their inner lumen diameter range from 0.017 to 0.021 inch (0.432 mm to 0.533 mm) and are usually 135 to 175 cm in length.

Figure 25:
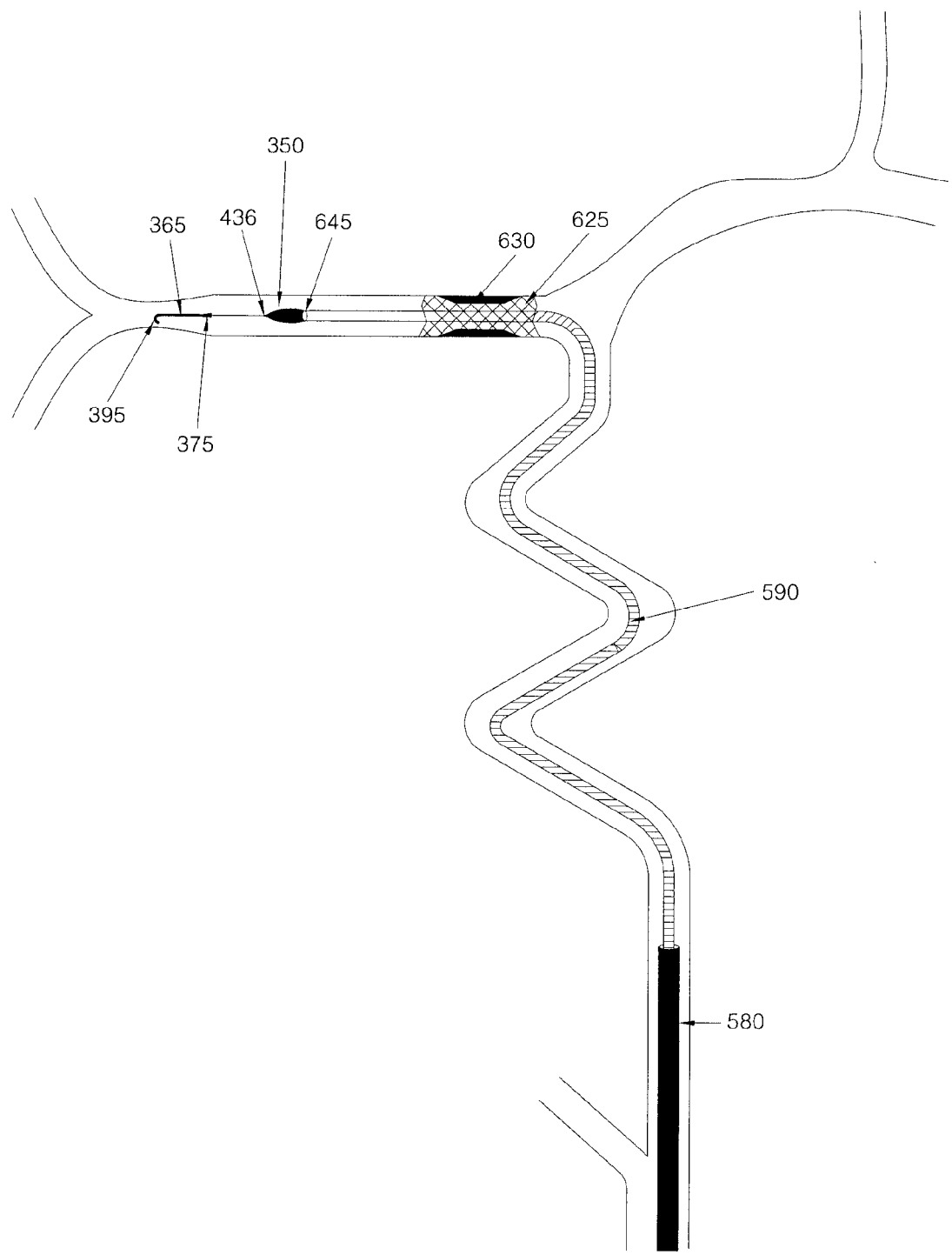
FIG. 25 is a schematic diagram illustrating the stent catheter or the tip of the standard microcatheter being advanced over the microguidewire to retrieve the distal embolic protection device.

FIG. 25 is a schematic diagram illustrating the tip of the standard microcatheter 645 being advanced over the microguidewire such that the filtering device 350 closes to the collapsed configuration to prevent spillage of the emboli or debris collected during the procedure. The stent is noted to be in good position 625 across the angioplastied area 630.

Figure 26:
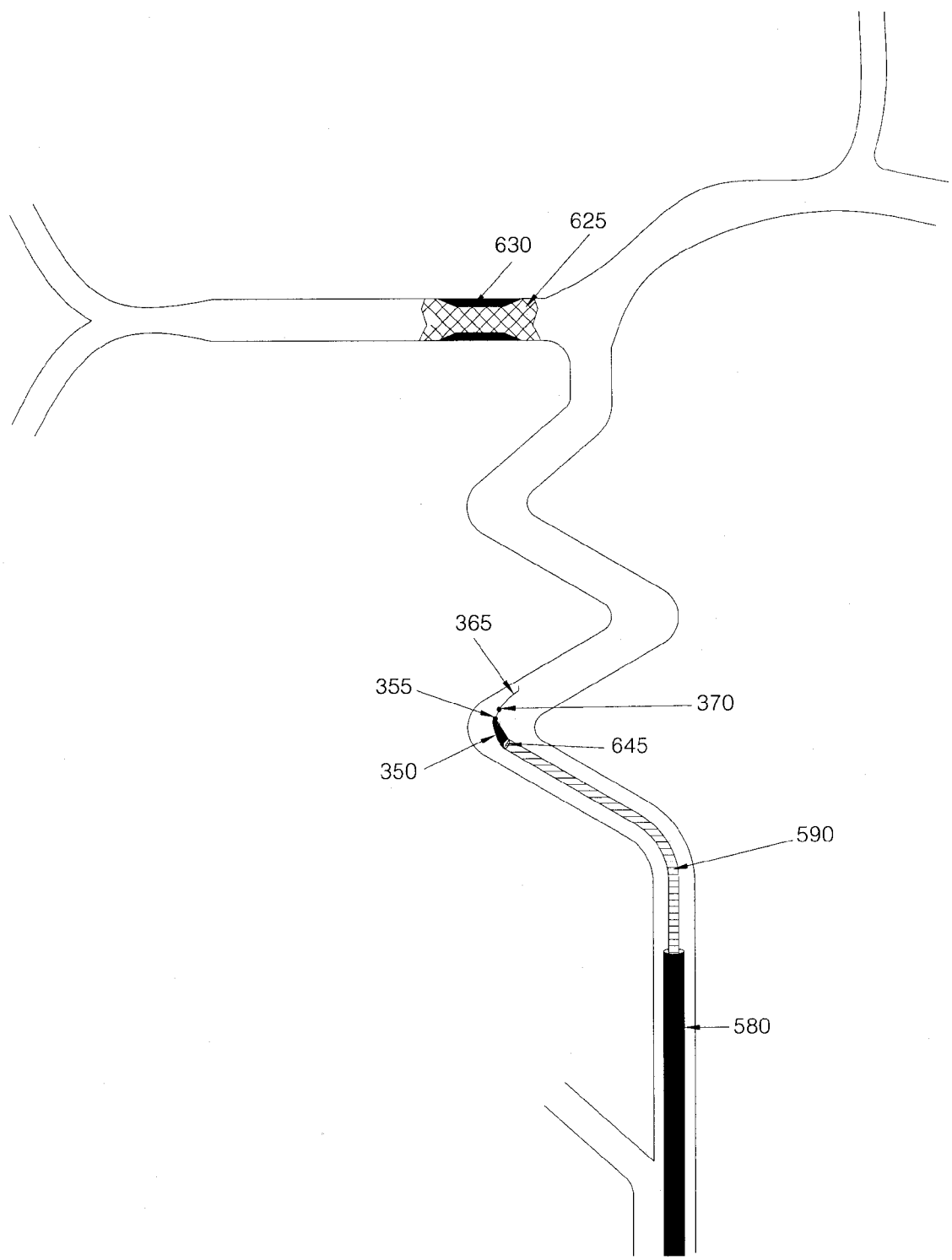
FIG. 26 is a schematic diagram illustrating the distal embolic protection device being safely retrieved by either the stent catheter or a standard microcatheter.

FIG. 26 is a schematic diagram illustrating the filtering device 350 in the closed non-expanded state being carefully withdrawn into the guide catheter 580. The microcatheter tip 645 is closely approximated to the struts of the filtering device to prevent spillage of the contents of the distal embolic protection device namely emboli or debris. The stent is noted to be in good position 625 across the angioplastied area 630.

Figure 27:
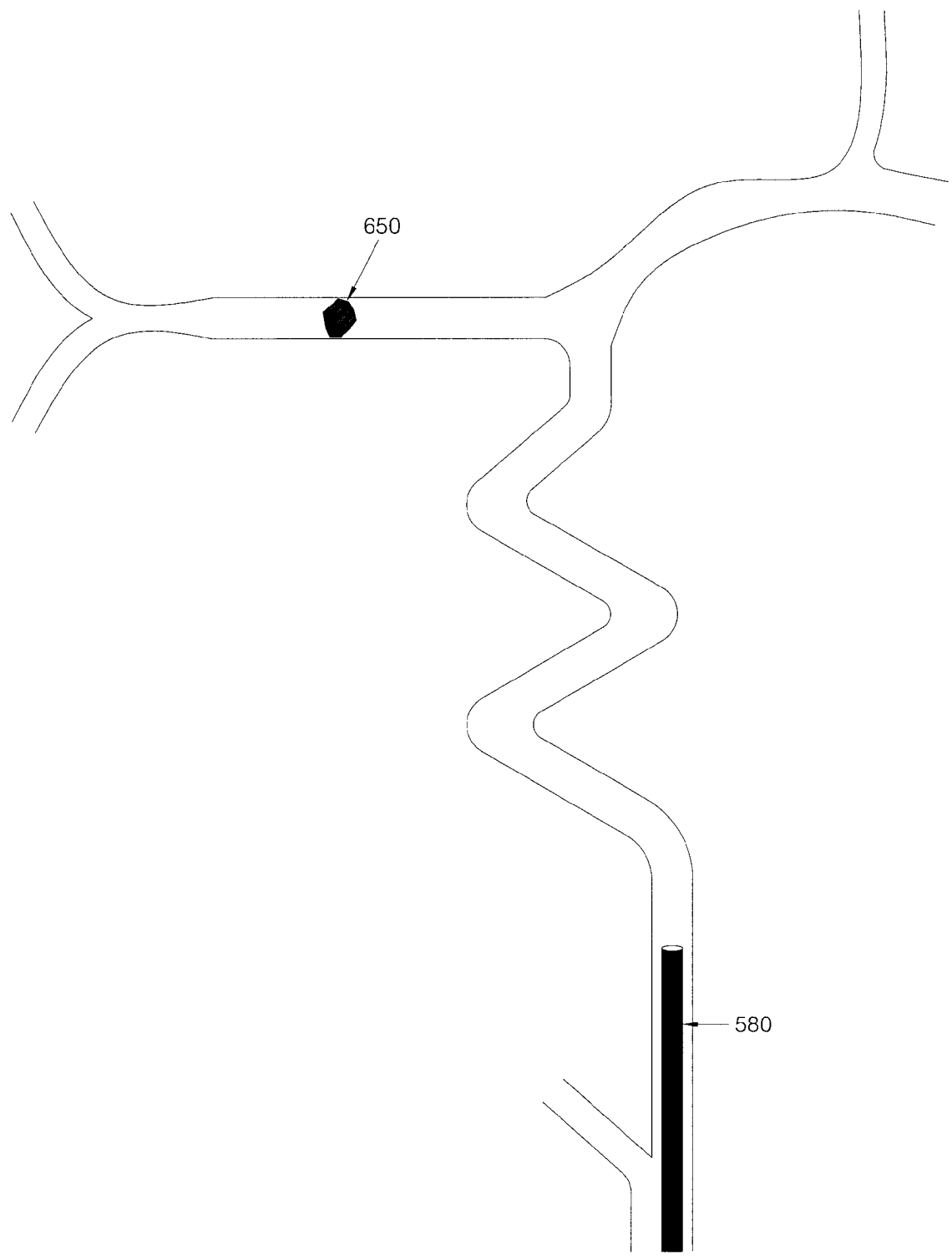
FIG. 27 is a schematic diagram illustrating another use for this distal embolic protection device namely during intra-arterial thrombolysis for thrombus or blood clot causing acute ischemic stroke.

FIG. 27 is a schematic diagram illustrating another use for this distal embolic protection device. This figure illustrates a thrombus or blood clot 650 in the right middle cerebral artery and is occluding this right middle cerebral artery and causing an acute ischemic stroke. The patient presents after 3 hours from symptom onset and is a candidate for immediate neurovascular interventional therapy with intra-arterial thrombolytic infusion. A guide catheter 580 (6 French or greater) is advanced into the right internal carotid artery.

Figure 28:
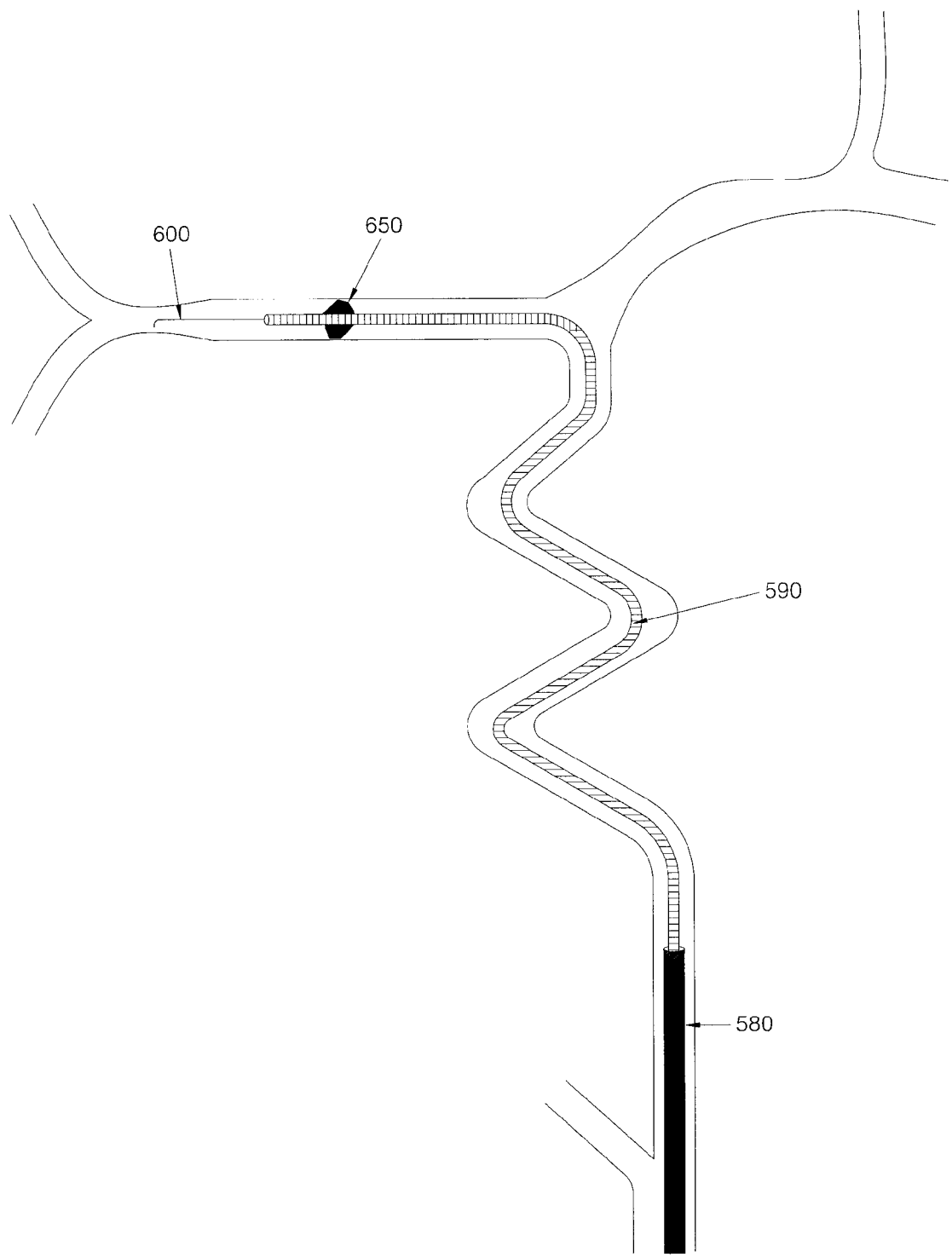
FIG. 28 is a schematic diagram illustrating a standard microcatheter being advanced across the thrombus or blood clot in the right middle cerebral artery over a microwire.

FIG. 28 is a schematic diagram illustrating a standard microcatheter 590 being advanced across the thrombus or blood clot 650 in the right middle cerebral artery over a microwire 600. Once the microcatheter is across the thrombus or blood clot, the microwire will be removed and a microcatheter angiogram may be performed to identify if the cerebral blood vessels distal to the thrombus or blood clot are patent.

Figure 29:
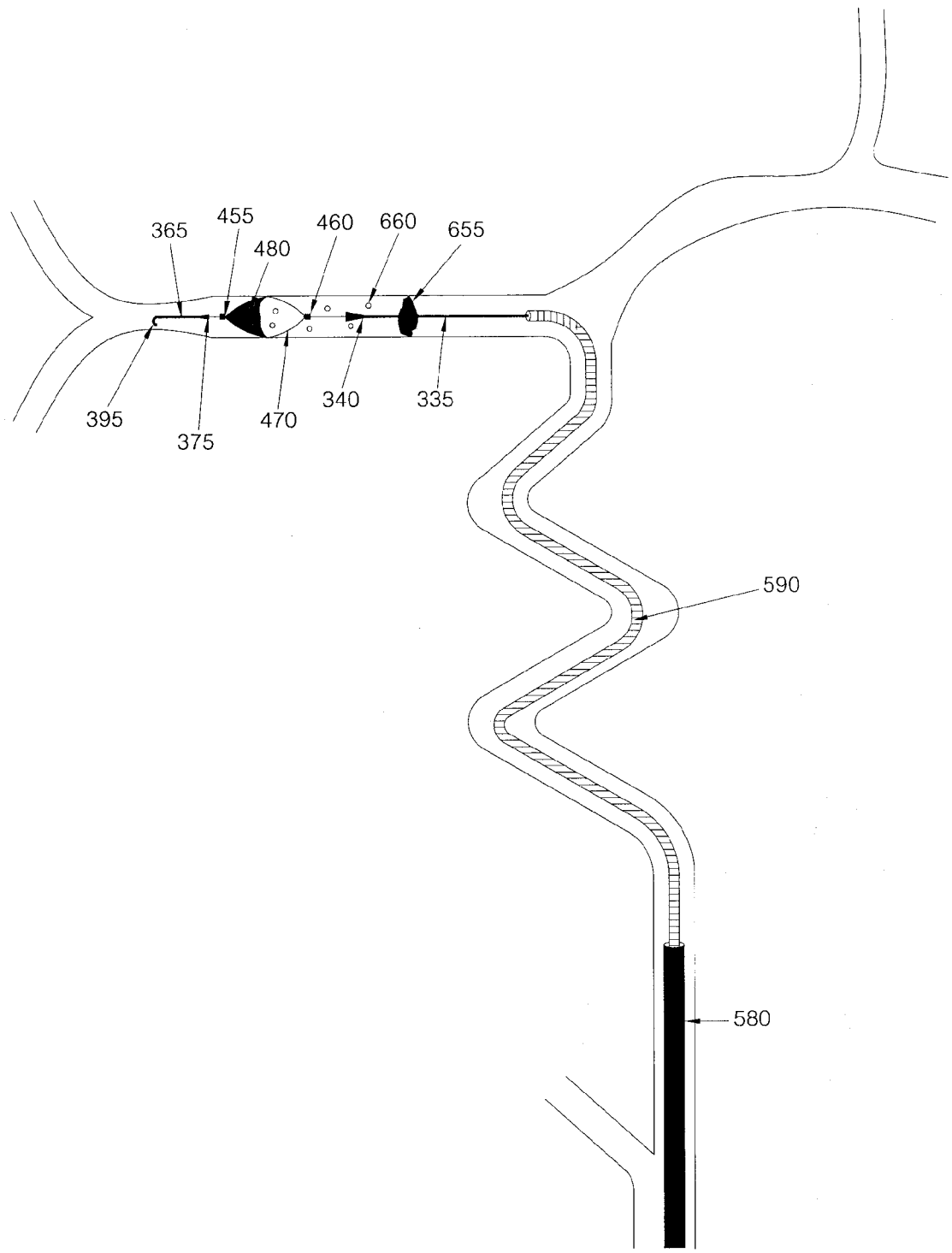
FIG. 29 is a schematic diagram illustrating a distal embolic protection device being deployed distal to the thrombus or blood clot causing the stroke and then the microcatheter is withdrawn back and intra-arterial thrombolysis is initiated.

FIG. 29 is a schematic diagram illustrating a distal embolic protection device is advanced through the microcatheter 590 into a position distal to the thrombus or blood clot 650 and then the microcatheter is withdrawn to the proximal part of the right middle cerebral artery to deploy the distal embolic protection device. The radio-opaque stops 340 and 375 in the microguidewire, as well as, the radio-opaque attachment points 455 and 460 of the distal embolic protection device are well visualized. Also the distal radio-opaque microguidewire segment 365 and the shapeable tip 395 are well visualized. Intra-arterial thrombolytic infusion is initiated through the microcatheter with the microguidewire in position 335. The thrombus or blood clot is broken down 655 into smaller emboli or debris 660, which are collected in the filter membrane 480 of the distal protection device. The struts 470 of the distal embolic protection device are in the expanded position to maintain the shape of the filter membrane.

Figure 30:
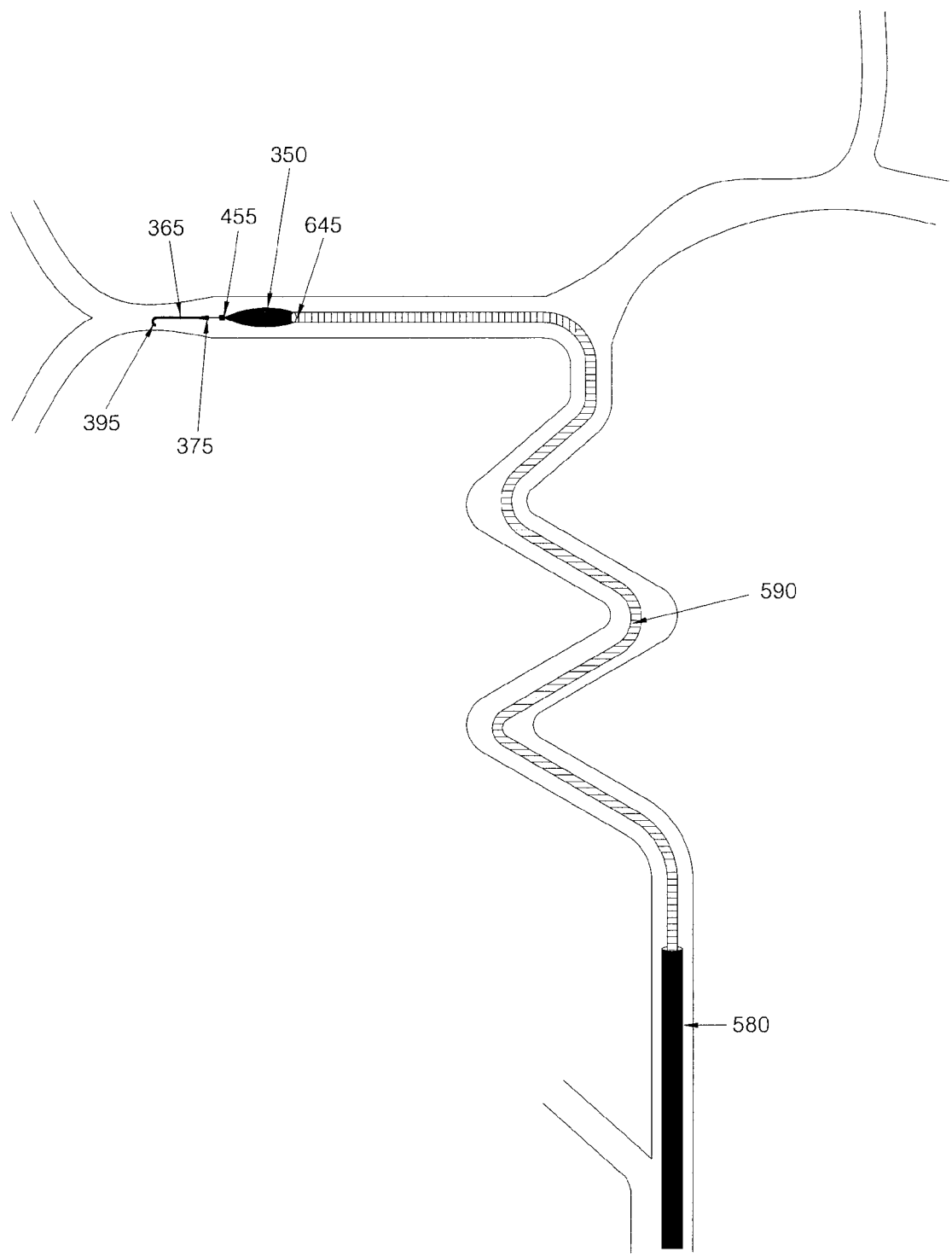
FIG. 30 is a schematic diagram illustrating the retrieval of the distal embolic protection device with the standard microcatheter.

FIG. 30 is a schematic diagram illustrating after intra-arterial thrombolysis, the microcatheter 590 is advanced over the microguidewire such that the filtering device 350 closes to the collapsed configuration to prevent spillage of the emboli or debris collected during the procedure. The filtering device 350 in the closed non-expanded state is then carefully withdrawn into the guide catheter 580. All through the process, the microcatheter tip 645 is closely approximated to the struts of the distal embolic protection device to prevent spillage of the contents of the distal embolic protection device namely emboli or debris.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

CITED REFERENCES

1. Sarti C, Rastenyte D, Cepaitis Z, Tuomilehto J. International trends in mortality from stroke, 1968 to 1994. Stroke. 2000; 31:1588-1601.
2. Wolf P A, D'Agostino R B. Epidemiology of Stroke. In: Barnett H J M, Mohr J P, Stein B M, Yatsu F, eds. Stroke: Pathophysiology, Diagnosis, and Management. 3rd ed. New York, N.Y.: Churchill Livingstone; 1998:6-7
3. Adams H P, Jr., Adams R J, Brott T, del Zoppo G J, Furlan A, Goldstein L B, Grubb R L, Higashida R, Kidwell C, Kwiatkowski T G, Marler J R, Hademenos G J. Guidelines for the early management of patients with ischemic stroke: A scientific statement from the Stroke Council of the American Stroke Association. Stroke. 2003; 34:1056-1083.
4. Rymer M M, Thrutchley D E. Organizing regional networks to increase acute stroke intervention. Neurol Res. 2005; 27:S9-16.
5. Furlan A, Higashida R, Wechsler L, Gent M, Rowley H, Kase C, Pessin M, Ahuja A, Callahan F, Clark W M, Silver F, Rivera F. Intra-arterial prourokinase for acute ischemic stroke. The PROACT II study: a randomized controlled trial. Prolyse in Acute Cerebral Thromboembolism. Jama. 1999; 282:2003-2011.
6. Yadav J S. Carotid stenting in high-risk patients: design and rationale of the SAPPHIRE trial. Cleve Clin J Med. 2004; 71 Suppl 1:S45-46.
7. Bose A, Hartmann M, Henkes H, Liu H M, Teng M M, Szikora I, Berlis A, Reul J, Yu S C, Forsting M, Lui M, Lim W, Sit S P. A novel, self-expanding, nitinol stent in medically refractory intracranial atherosclerotic stenoses: the Wingspan study. Stroke. 2007; 38:1531-1537. Epub 2007 March 1529.

What is claimed is:

1. A distal embolic protection device for filtering thromboembolic material, debris or clots released during percutaneous neurovascular interventional procedures specifically performed in cerebral arterial blood vessels of a human, not attached to a balloon or a stent, and comprising:
a variable thickness microguidewire comprising a thinner segment bordered by thicker segments,
wherein said thinner segment is about 0.008 to 0.010 inch in thickness and has a length,
wherein the thicker segments are no more than about 0.017 inch in thickness,
a filtering device movable between an expanded configuration and a collapsed configuration, the filtering device configured to be deployed beyond an area of blockage or clot in a cerebral arterial blood vessel, the filtering device configured to be tracked uncovered through a microcatheter having an inner diameter of 0.017 inches from a proximal end of the microcatheter to a distal end of the microcatheter, the filtering device comprising:
an expansion assembly,
a filter membrane, and
two mobile attachment points, one of the mobile attachment points on each end of the filtering device, the mobile attachment points each having a length that covers a portion of the length of the thinner segment of the microguidewire, the lengths of the mobile attachment points together being less than the length of the thinner segment of the microguidewire,
a first coil between one of the mobile attachment points and one of the thicker segments;
a second coil between the other of the mobile attachment points and the other of the thicker segments;
wherein the thinner segment of the microguidewire where the filtering device is mounted comprises a core microguidewire, and
wherein each of the thicker segments of the microguidewire comprises the core microguidewire coated by a flexible hypotube,
wherein the filtering device is rotatably mounted on the thinner segment of the variable thickness microguidewire between the thicker segments via the mobile attachment points, the filtering device rotationally and longitudinally displaceable relative to and independently of the microguidewire,
wherein the thickness of the distal embolic protection device in the collapsed configuration measures no more than about 0.017 inch,
wherein the length of the thinner segment of the variable thickness microguidewire is longer than a length of the filtering device in the collapsed configuration,
wherein the filtering device is configured to float along the length of the thinner segment of the variable thickness microguidewire.

2. The distal embolic protection device of claim 1, wherein:
the expansion assembly comprises:
a plurality of struts,
a single ring, or
both a plurality of struts and a single ring,
wherein said plurality of struts or said ring or said both plurality of struts and single ring comprise a biocompatible material, said biocompatible material comprising platinum, stainless steel, or nickel-titanium, and
the filtering device is no more than about 0.017 inch in thickness in the collapsed configuration, and in the expanded configuration the filtering device has diameter of from about 1.5 mm to 4.5 mm, and
the filter membrane has a hemispherical or conical shape.

3. The distal embolic protection device of claim 1, wherein:
the thicker segments of the microguidewire are no more than about 0.014 inch in thickness, and
the microguidewire has a length ranging from about 190 cm to about 300 cm.

4. The distal embolic protection device of claim 1, wherein:
the core microguidewire comprises a metal or alloy, said metal being stainless steel and said alloy being nickel-titanium, and
the flexible hypotube comprises platinum, tantalum, gold, palladium, tungsten, tin, silver, titanium, nickel, zirconium, rhenium, bismuth, molybdenum or a combination thereof.

5. The distal embolic protection device of claim 1, wherein:
the microguidewire comprises a proximal stop and a distal stop where the thinner segment of the microguidewire meets the thicker segments of the microguidewire, wherein the thickness of the stops is about 0.014 inch to about 0.017 inch, and
the two mobile attachment points of the filtering device comprises:
a distal mobile attachment point, and
a proximal mobile attachment point,
wherein each of the two mobile attachment points is between the proximal and distal stops, such that there is rotatory as well as longitudinal mobility of the microguidewire through, and independently of, the filtering device between the proximal and distal stops.

6. The distal embolic protection device of claim 1, wherein: the filter membrane comprises a biopolymer having pores large enough to allow blood cells to pass through the filter but small enough to capture debris and clots that are released during percutaneous neurovascular interventional procedures in the cerebral arterial blood vessels.

7. The distal embolic protection device of claim 6, wherein the pore openings are about 50-150 microns in diameter.

8. The distal embolic protection device of claim 1, wherein: the distal portion of the filtering device is covered by the filter membrane, and wherein the filter membrane comprises:
   a biomedical polymer selected from the group consisting of polyethylene, polyester, polypropylene, poly tetra fluoro-ethylene, polyamides, polycarbonate and polyethylene-terephthalate, or
   a membrane comprising:
      a biomedical polymer, and
      radio-opaque particles or agents,
         wherein the membrane is visible during fluoroscopic neurovascular interventional procedures.

9. The distal embolic protection device of claim 8, wherein the radio-opaque particles in the membrane comprise tantalum or gold and the radio-opaque agents comprise barium sulfate, tungsten powder, bismuth subcarbonate, bismuth oxychloride, or iodine containing compounds.

10. The distal embolic protection device of claim 1, wherein: the expansion assembly comprises:
   a plurality of struts,
   a single ring, or
   a plurality of struts and a single ring.

11. The distal embolic protection device of claim 10, wherein the expansion assembly comprises:
   a biocompatible metal or alloy, or
   a radio-opaque material.

12. The distal embolic protection device of claim 11, wherein the biocompatible metal or alloy comprises stainless steel, platinum or nickel-titanium and the radio-opaque material comprises tantalum, platinum, tungsten or gold.

13. The distal embolic protection device of claim 1, wherein the microguidewire comprises:
   a shapeable tip coated with a hypotube, and
   proximal and distal stops,
      wherein the shapeable tip of the microguidewire coated with the hypotube, the two mobile attachment points, and the proximal and distal stops are covered by a radio-opaque material, metal or alloy.

14. The distal embolic protection device of claim 13, wherein the metal or alloy comprises stainless steel or nickel-titanium, and the radio-opaque material comprises tantalum, platinum, tungsten or gold.

15. A distal embolic protection device for filtering thrombo-embolic material, debris or clots released during percutaneous neurovascular interventional procedures specifically performed in cerebral arterial blood vessels, not attached to a balloon or a stent, and comprising:
   a variable thickness microguidewire comprising:
      a thinner segment having a thickness of about 0.008 to 0.010 inch,
      a first thicker segment distal to the thinner segment, the first thicker segment coated with a distal hypotube,
      a second thicker segment proximal to the thinner segment, the second thicker segment coated with a proximal hypotube, and
      a shapeable distal tip,
   a filtering device movable between an expanded configuration and a collapsed configuration, the filtering device configured to be deployed beyond an area of blockage or clot in a cerebral arterial blood vessel, the filtering device configured to be tracked uncovered through a microcatheter having an inner diameter of 0.017 inches from a proximal end of the microcatheter to a distal end of the microcatheter, the filtering device comprising:
      an expansion assembly,
      a filter membrane,
      a distal mobile attachment point on a distal end of the filtering device, and
      a proximal mobile attachment point on a proximal end of the filtering device,
         wherein the expansion assembly is attached to both the proximal and distal mobile attachment points, and
         wherein the filter membrane is attached to at least the distal mobile attachment point,
         wherein the filtering device is rotatably mounted on the thinner segment of the variable thickness microguidewire between the first thicker segment and the second thicker segment via the proximal and distal mobile attachment points, the filtering device rotationally and longitudinally displaceable relative to and independently of the microguidewire,
         wherein the thickness of the distal embolic protection device in the collapsed configuration measures no more than about 0.017 inch,
         wherein the variable thickness microguidewire is configured to float along the thinner segment of the variable thickness microguidewire, and
         wherein the shapeable tip of the microguidewire, the expansion assembly and the filter membrane all comprise a radio-opaque material, metal or alloy.

16. The distal embolic protection device of claim 15, wherein a distal-most 30 cm or less of the microguidewire is coated by a flexible hypotube, and wherein the proximal and distal mobile attachment points are covered by a radio-opaque material, metal or alloy.

17. A distal embolic protection device, not attached to a balloon or a stent, for filtering thrombo-embolic material, debris or clots released during percutaneous neurovascular interventional procedures specifically performed in cerebral arterial blood vessels of a human, and comprising:
   a core microguidewire having a diameter of about 0.008 to 0.010 inch,
   a filtering device movable between an expanded configuration and a collapsed configuration, the filtering device configured to be deployed beyond an area of blockage or clot in a cerebral arterial blood vessel, the filtering device configured to be tracked through a microcatheter having an inner diameter of 0.017 inches uncovered, the filtering device comprising:
      an expansion assembly,
      a filter membrane, and
      a proximal mobile attachment point on a proximal end of the filtering device, and
      a distal mobile attachment point on a distal end of the filtering device,
   wherein a first portion of the microguidewire is coated with a proximal flexible hypotube and a second portion of the microguidewire is coated with a distal flexible hypotube, the first portion longitudinally spaced from the second portion, the coated portions being no more than about 0.017 inch thick, and
   wherein the filtering device is rotatably mounted on the microguidewire between the hypotubes via the mobile attachment points, such that the filtering device may be rotationally and longitudinally displaced relative to and independently of the microguidewire and hypotubes,
wherein the thickness of the distal embolic protection device in the collapsed configuration measures no more than about 0.017 inch,
wherein a length of the microguidewire not covered by the hypotubes is longer than a length of the filtering device in the collapsed configuration.

18. The distal embolic protection device of claim 17, wherein the metal or alloy comprises platinum, tantalum, gold, palladium, tungsten, tin, silver, titanium, nickel, zirconium, rhenium, bismuth, molybdenum, or combinations thereof.

19. The distal embolic protection device of claim 1, wherein the expansion assembly comprises a plurality of struts.

20. The distal embolic protection device of claim 1, wherein the expansion assembly comprises a ring.

21. The distal embolic protection device of claim 1, wherein the expansion assembly comprises a plurality of struts coupled to a ring.

22. The distal embolic protection device of claim 1, wherein the filter membrane has a hemispherical or conical shape.

23. The distal embolic protection device of claim 1, wherein the thicker segments of the microguidewire are no more than about 0.014 inch in thickness.

24. The distal embolic protection device of claim 1, wherein the microguidewire has a length ranging from about 190 cm to about 300 cm.

25. The distal embolic protection device of claim 1, wherein the filter membrane comprises:
a biomedical polymer, and
radio-opaque particles or agents.

26. The distal embolic protection device of claim 1, wherein the microguidewire comprises a shapeable tip.

27. The distal embolic protection device of claim 15, wherein the filter membrane comprises a biomedical polymer and radio-opaque particles.

28. The distal embolic protection device of claim 15, further comprising:
a first coil between the proximal mobile attachment points and the first thicker segment; and
a second coil between the distal mobile attachment points and the second thicker segment.

29. The distal embolic protection device of claim 17, wherein the filter membrane comprises a biomedical polymer and radio-opaque particles.

30. The distal embolic protection device of claim 17, further comprising:
a first coil between the proximal mobile attachment points and the proximal flexible hypotube; and
a second coil between the distal mobile attachment points and the distal flexible hypotube.

31. A distal embolic protection device comprising:
a core wire having a diameter of about 0.008 to 0.010 inch, at least a portion of the core wire comprising a thinner segment;
a proximal hypotube coating around the core wire and proximal to the thinner segment;
a distal hypotube coating around the core wire and distal to the thinner segment, wherein at least one of the proximal coating and the distal coating comprises a coil;
a filtering device around the thinner segment and between the proximal hypotube coating and the distal hypotube coating, the filtering device rotatably and longitudinally movable relative to the thinner segment, the filtering device transformable between a collapsed configuration and an expanded configuration, the filtering device having a thickness of no more than about 0.017 inches in the collapsed configuration, the filtering device comprising:
a proximal attachment point, a distal attachment point,
a plurality of struts between the proximal attachment point and the distal attachment point, and
a porous filter membrane coupled to the plurality of struts.

32. The distal embolic protection device of claim 31, wherein at least each of the proximal hypotube coating, the distal hypotube coating, and the plurality of struts comprises radio-opaque material.

33. The distal embolic protection device of claim 32, wherein at least each of the proximal attachment point and the distal attachment point comprises radio-opaque material.

34. The distal embolic protection device of claim 31, wherein the filter membrane comprises a biomedical polymer and radio-opaque particles.

35. The distal embolic protection device of claim 31, further comprising:
a proximal coil between the proximal attachment point and the proximal coating; and
a distal coil between the distal attachment point and the distal coating.

36. The distal embolic protection device of claim 31, wherein the filter membrane is hemispherical.

37. The distal embolic protection device of claim 31, wherein the filter membrane is conical.

38. The distal embolic protection device of claim 31, wherein each of the plurality of struts is in a plane parallel with the core wire.

39. The distal embolic protection device of claim 31, wherein each of the plurality of struts is helical about the core wire.

40. The distal embolic protection device of claim 31, further comprising a ring, wherein the plurality of struts extend from the distal attachment point to the ring and wherein the ring is coupled to the proximal attachment point.

41. The distal embolic protection device of claim 31, wherein each of the proximal hypotube coating and the distal hypotube coating is no more than about 0.017 inch thick.

* * * * *